(12) United States Patent
Morrissey et al.

(10) Patent No.: US 7,622,437 B2
(45) Date of Patent: Nov. 24, 2009

(54) TISSUE FACTOR COMPOSITIONS AND METHODS

(75) Inventors: James H. Morrissey, Champaign, IL (US); Vincent S. Pureza, Champaign, IL (US); Stephen G. Sligar, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 238 days.

(21) Appl. No.: 11/259,950

(22) Filed: Oct. 27, 2005

(65) Prior Publication Data

US 2006/0088524 A1   Apr. 27, 2006

Related U.S. Application Data

(63) Continuation-in-part of application No. 11/033,489, filed on Jan. 11, 2005, which is a continuation-in-part of application No. 10/465,789, filed on Jun. 18, 2003, now Pat. No. 7,083,958, which is a continuation-in-part of application No. 09/990,087, filed on Nov. 20, 2001, now Pat. No. 7,048,949.

(60) Provisional application No. 60/622,737, filed on Oct. 27, 2004, provisional application No. 60/536,281, filed on Jan. 13, 2004, provisional application No. 60/252,233, filed on Nov. 20, 2000.

(51) Int. Cl.
*A61K 38/00* (2006.01)
*C07K 14/00* (2006.01)

(52) U.S. Cl. .......................................... 514/2; 530/300

(58) Field of Classification Search ........................ None
See application file for complete search history.

(56) References Cited

U.S. PATENT DOCUMENTS

| | | | |
|---|---|---|---|
| 5,374,617 A * | 12/1994 | Morrissey et al. ............... | 514/8 |
| 5,883,078 A * | 3/1999 | Seelich et al. .................. | 514/12 |
| 6,132,729 A | 10/2000 | Thorpe et al. | |
| 6,172,262 B1 | 1/2001 | McQuade et al. | |
| 6,248,353 B1 | 6/2001 | Singh | |
| 7,048,949 B2 | 5/2006 | Sligar et al. | |
| 7,083,958 B2 | 8/2006 | Sligar et al. | |
| 2004/0053384 A1 | 3/2004 | Sligar et al. | |
| 2005/0152984 A1 | 7/2005 | Sligar et al. | |
| 2005/0182243 A1 | 8/2005 | Sligar et al. | |
| 2006/0211092 A1 | 9/2006 | Sligar et al. | |
| 2006/0211093 A1 | 9/2006 | Sligar et al. | |

FOREIGN PATENT DOCUMENTS

| | | |
|---|---|---|
| WO | WO 93/17031 | 9/1993 |
| WO | WO 00/75187 | 12/2000 |
| WO | WO 01/02551 | 1/2001 |
| WO | WO 02/40501 | 5/2002 |

OTHER PUBLICATIONS

Norledge, B. et al., "The Tissue Factor/Factor VIIa/Factor Xa Complex: A Model Built by Docking and Site-Directed Mutagenesis", Proteins: Structure, Function, and Genetics 53: 640-648 (2003).*
Hathcock, J. et al., "Phospholipid Regulates the Activation of Factor X by Tissue Factor/Factor VIIa (TF/VIIa) via Substrate and Product Interactions", Biochemistry 44: 8187-8197 (2005).*
Alam et al. (2005) "Hemorrhage Control in the Battlefield: Role of New Hemostatic Agents," *Mil. Med.* 170:63-69.
Altenburg et al. (2007) "Apolipoprotein E Precursor [*Homo sapiens*]," NCBI Accession No. NP_000032.
Amarante et al. (1999) "Hemoglobin, Beta [*Bos Taurus*]," NCBI Accession No. NP_776342.
Armstrong et al. (1990) "The Active Site of Membrane-Bound Meizothrombin. A Fluorescence Determination of Its Distance from the Phospholipid Surface and Its Conformational Sensitivity to Calcium and Factor Va," *J. Biol. Chem.* 265:6210-6218.
Atkinson et al. (1986) "Recombinant Lipoproteins: Implications for Structure and Assembly of Native Lipoproteins," *Ann. Rev. Biophys. Chem.* 15:403-456.
Bach et al. (1986) "Factor VII Binding to Tissue Factor in Reconstituted Phospholipid Vesicles: Induction of Cooperativity by Phosphatidylserine," *Biochemistry* 25:4007-4020.
Bakker et al. (1982) "Phospholipid Substitution of the Purple Membrane," *Methods Enzymol.* 88:26-30.
Barnes et al. (1999) "A Review of Central 5-HT Receptors and Their Function," *Neuropharmacol.* 38(8):1083-1152.
Bayburt et al. (May 2002) "Single-Molecule Height Measurements on Microsomal Cytochrome P450 in Nanometer-Scale Phospholipid Bilayer Disks," *Proc. Nat. Acad. Sci. USA* 99:6725-6730.
Bayburt et al. (Nov. 2003) "Self-Assembly of Single Integral Membrane Proteins into Soluble Nanoscale Phospholipid Bilayers," *Protein Science* 12:2476-2481.
Bayburt et al. (Jul. 18, 2002) "Self-Assembly of Discoidal Phospholipid Bilayer Nanoparticles with Membrane Scaffold Proteins," *Nano Lett.* 2(8):853-856.
Bayburt et al. (1998) "Reconstitution and Imaging of a Membrane Protein in a Nanometer-Size Phospholipid Bilayer," *J. Struct. Biol.* 123:37-44.
Bayburt et al. (Jun. 2000) "Single Molecule Height Measurements on a Membrane Protein in Nanometer-Scale Phospholipid Bilayer Disks," *Langmuir* 16(14):5993-5997.
Bayley et al. (2001) "Delipidation, Renaturation, and Reconstitution of Bacberiorhodopsin," *Methods Enzymol.* 88:74-81.
Bergeron et al. (1995) "Apolipoprotein A-I Conformation in Reconstituted Discoidal Lipoproteins Varying in Phospholipid and Cholesterol Content," *J. Biol. Chem.* 270:27429-27438.

(Continued)

*Primary Examiner*—Anand U Desai
(74) *Attorney, Agent, or Firm*—Greenlee, Winner and Sullivan, P.C.

(57) ABSTRACT

Tissue Factor (natural or recombinant truncated) can be incorporated into stable, soluble nanoscale particles so that activity is maintained. These particles can be used as a reagent in prothrombin clotting time assays or they can be used in therapeutic compositions for use in humans or animals. Therapeutic settings can include supplementation in the case of a genetic deficiency, uncontrolled bleeding, surgical incisions or seepage, thrombocytopenia, soft tissue trauma or other trauma, to effect tumor regression or to inhibit tumor growth.

8 Claims, 10 Drawing Sheets

OTHER PUBLICATIONS

Bergeron et al. (1997) "Characterization of Human Apolipoprotein A-I Expressed in *Escherichia coli*," *Biochim. Biophys. Acta* 1344:139-152.

Billy et al. (1995) "Prothombin Contributes to the Assembly of the Factor Va-Factor Xa Complex at Phosphatidylserine-Containing Phospholipid Membranes," *J. Biol. Chem.* 270:26883-26889.

Boguski et al. (1986) "On Computer-Assisted Analysis of Biological Sequences: Proline Punctuation, Consensus Sequences, and Apolipoprotein Repeats," *J. Lipid Res.* 27:1011-1034.

Borhani, et al. (1997) "Crystal Structure of Truncated Human Apolipoprotein A-I Suggests a Lipid-Bound Conformation," *Proc. Nat. Acad. Sci. USA* 94:12291-12296.

Bolanos-Garcia et al. (2003) "On the Structure and Function of Apolipoproteins: More than a Family of Lipid-Binding Proteins," *Prop. Biophys. Mol. Biol.* 83:47-68.

Brekken et al. (2001) "Vascular Endothelial Growth Factor and Vascular Targeting of Solid Tumors," *Anticancer Res.* 21:4221-4230.

Brouillette et al. (1984) "Structural Studies of Apolipoprotein A-I/ Phosphatidylcholine Recombinants by High-Filed Proton NMR, Nondenaturing Gradient Gel Electrophoresis, and Electron Microscopy," *Biochemistry* 23:359-397.

Brouillette et al. (2001) "Structural Models of Human Apolipoprotein A-I: A Critical Analysis and Review," *Biochim. Biophys. Acta* 1531:4-46.

Bruhn et al. (1991) "An Approach to the Functional Analysis of Lecithin-Cholesterol Acryltransferase. Activation by Recombinant Normal and Mutagenized Apolipoprotein AI," *Biological Chem. Hoppee-Seyler* 372(3):225-234.

Burgess et al. (Nov. 2, 1999) "Deletion of the C-Terminal Domain of Apolipoprotein A-I Impairs Cell Surface Binding and Lipid Efflux in Macrophage," *Biochemistry* 38(44):14524-14533.

Cao et al. (Feb. 10, 2003) "Bispecific Antibody Conjugates in Therapeutics," *Adv. Drug Del. Rev.* 55(2):171-197.

Carlson et al. (Mar. 2000) "Nanopatterning Phospholipid Bilayers," *Langmuir* 16(8):3927-3931.

Carlson et al. (Sep. 1997) "Imaging and Manipulation of High-Density Lipoproteins," *Biophys. J.* 73:1184-1189.

Carr et al. (1998) "Recombinant Factor VIIa: Clinical Applications for an Intravenous Hemostatic Agent With Broab-Spectrum Potential," *Expert Rev. Cardiovasc. Ther.* 2:661-674.

Carter (2001) "Improving the Efficacy of Antibody-Based Cancer Therapies," *Nat. Rev. Cancer* 1:118-129.

Chen et al. (2002) "Amino Acids in SRS1 and SRS6 are Critical for Furanocoumarin Metabolism by CYP6B1v1, a Cytochrome P450 Monooxygenase," *Insect Mol. Biol.* 11:175-186.

Chou et al. (Jan. 15, 1974) "Conformational Parameters for Amino Acids in Helical, β-Sheet, and Random Coil Regions Calculated from Proteins," *Biochemistry* 13(2):211-222.

Chou et al. (1978) "Empirical Predictions of Protein Conformation," *Ann. Rev. Biochem.* 47:251-278.

Civjan et al. (2003) "Direct Solubilization of Heterologously Expressed Membrane Proteins by Incorporation into Nanoscale Lipid Bilayers," *BioTechniques* 35:556-563.

Dalton et al. (Sep. 15, 1993) "Structural and Functional Domains of Apolipoprotein A-I Within High Density Lipoproteins," *J. Biol. Chem.* 268(26):19274-19283.

De Donato et al. (2003) "Myoglobin [*Bos Taurus*]," NCBI Accession No. NP_776306.

Dencher et al. (1982) "Preparation and Properties of Monomeric Bacteriorhodosin," *Methods Enzymol.* 88:5-10.

Denisov et al. (Mar. 2004) "Directed Self-Assembly of Monodisperse Phospholipid Bilayer Nanodiscs with Controlled Size," *J. Am. Chem. Soc.* 126(11):3477-3487.

Drake, D.S. et al. (1989) "Selective Cellular Expression of Tissue Factor in Human Tissues. Implications for Disorders of Hemostasis and Thrombosis," *Am. J. Pathol.* 134:1087-1097.

Duan et al. (Apr. 15, 2004) "Co-Incorporation of Heterologously-Expressed *Arabidopsis* Cytochrome P450 and P450 Reductase into Soluble Nanoscale Lipid Bilayers," *Arch. Biochem. Biophys.* 424(2):141-153.

Dubois et al. (Jun. 2001) "Self-Assembly or Regular Hollow Lcosahedra in Salt-Free Catanionic Solutions," *Nature* 411:672-675.

Durbin et al. (Dec. 1999) "Lipid-Free Apolipoproteins A-I and A-II Promote Remodeling of Reconstituted High Density Lipoproteins and Alter Their Reactivity with Lecithin: Cholesterol Acyltransferase," *J. Lipid Res.* 40(12):2293-2302.

Fair (Oct. 1983) "Quantitation of Factor VII in the Plasma of Normal and Warfarin-Treated Individuals by Radioimmunoassay," *Blood* 62(4):784-791.

Falls et al. (2000) "Role of Phosphatidylethanolamine in Assembly and Function of the Factor IXa-Factor VIIIa Complex on Membrane Surfaces," *Biochemistry* 39:13216-13222.

Fasman, G.D. (1987) "The Road from Poly(α-Amino Acids) to the Prediction of Protein Conformation," *Biopolymers* 26(Supp.):S59-S79.

Fidge et al. (Feb. 1999) "High Density Lipoprotein Receptors, Binding Proteins, and Ligands," *J. Lipid Res.* 40(2):187-201.

Fielding et al. (1991) "Dynamics of Lipoprotein Transport in the Circulatory System," In; *Biochemistry of Lipids, Lipoproteins, and Membranes*, Vance et al. Eds., Elsevier Press, Amsterdam, CH. 15, pp. 427-459.

Fiore et al. (Jan. 7, 1994) "The Biochemical Basis for the Apparent Defect of Soluble Mutant Tissue Factor in Enhancing the Proteolytic Activities of Factor VIIa," *J. Biol. Chem.* 269(1):143-149.

Forte et al. (1971) "Electron Microscopic Study on Reassembly of Plasma High Density Apoprotein with Various Lipids," *Biochim. Biophys. Acta* 248:381-386.

Frank et al. (1998) "Importance of Central α-Helixes of Human Apolipoprotein A-I in The Maturation of High Density Lipoproteins," *Biochemistry* 37(39):13902-13909.

Frank et al. (1997) "Deletion of Central α-Helices in Human Apolipoprotein A-I Effect on Phospholipid Association," *Biochemistry* 36:1798-1806.

Friis et al. (Feb. 1999) "An Approach to Long-Range Electron Transfer Mechanisms in Mettalloproteins: in situ Scanning Tunneling, Microscopy with Submolecular Resolution," *Proc. Nat. Acad. Sci. USA* 96:1379-1384.

Frischknecht et al. (2007) "Beta Globin [*Homo sapien*]," NCBI Accession No. NP_000509.

Gilbert et al. (1995) "Phosphatidylethanolamine Induces High Affinity Binding Sites for Factor VIII on Membranes Containing Phosphatidyl-L-Serine," *J. Biol. Chem.* 270:18500-18505.

Gillotte et al. (1996) "Apolipoprotein A-I Structural Modification and the Functionality of Reconstituted High Density Lipoprotein Particles in Cellular Cholesterol Efflux," *J. Biol. Chem.* 271(39):23792-23798.

Gillotte et al. (Jan. 1999) "Apolipoprotein-Mediated Plasma Membrane Microsolubilization. Role of Lipid Affinity and Membrane Penetration in the Efflux of Cellular Cholesterol and Phospholipid,"*J. Biol. Chem.* 274(4):2021-2028.

Glomset et al. (1968) "The Plasma Lecithin: Cholesterol Acyltransferase Reaction," *J. Lipid Res.* 9:155-167.

Gottstein et al. (2001) "Generation and Characterization of Recombinant Vascular Targeting Agents from Hybridome Cell Lines," *Bio Techniques* 30(1):190-194.

Heyn et al. (1982) "Reconstitution of Monomeric Bacteriorhodopsin into Phospholipid Vesicles," *Methods Enzymol.* 88:31-35.

Holvoet et al. (1995) "Phospholipid Binding and Lecithin-Cholesterol Acyltransferase Activation Properties of Apolipoprotein A-I Mutants," *Biochemistry* 34:13334-13342.

Hu et al. (Aug. 15, 2003) "Comparison of Three Different Targeted Tissue Factor Fusion Proteins fro Inducing Tumor Vessel Thrombosis," *Cancer Res.* 63:5046-5053.

Huang et al. (1997) "Tumor Infarction in Mice by Antibody-Directed Targeting of Tissue Factor to Tumor Vasculature," *Science* 275:547-550.

Hussein et al. (2007) "Alpha 1 Globin [*Homo sapien*]," NCBI Accession No. NP_000549.

Imaoka et al. (1992) "Role of Phospholipids in Reconstituted Cytochrome P450 3A Form and Mechanism of Their Activation of Catalytic Activity," *Biochemistry* 31:6063-6069.

Jamsai et al. (2006) "Hemoglobin Beta Adult Major Chain [*Mus musculus*]," NCBI Accession No. NP_032246.

Ji et al. (1998) "G Protein-Coupled Receptors," 273:17299-17302.
Jin et al. (1995) "Surface Plasmon Resonance Biosensor Studies of Human Wild-Type and Mutant Lecithin Cholesterol Acyltransferase Interactions with Lipoproteins," *Biochemistry* 38(47)15659-15665.
Jonas, A. (1986) "Reconstitution of High Density Lipoproteins," *Methods Enzymol.* 128:553-582.
Jonas, A. (1991) "Lecithin-Cholesterol Acyltransferase in the Metabolism of High-Density Lipoproteins," *Biochim. Biophys. Acta* 1084:205-220.
Jonas et al. (1989) "Defined Apolipoprotein A-I Conformation in Reconstituted High Density Lipoprotein Disks," *J. Biol. Chem.* 264(9):4818-4824.
Koning et al. (2002) "Endothelial Cells at Inflammatory Sites as Targets for Therapeutic Intervention," *Endothelium* 9:161-171.
Koppaka et al. (May 1999) "The Structure of Human Lipoprotein A-I," *J. Biol. Chem.* 274(21):14541-14544.
Korenbrot, J.I. (1982) "The Assembly of Bacteriorhodopsin-Containing Planar Membranes by the Sequential Transfer of Air-Water Interface Films," *Methods Enzymol.* 88:45-55.
Laccotripe et al. (1997) "The Carboxyl-Terminal Hydrophobic Residues of Apolipoprotein A-I Affects its Rate of Phospholipid Binding and Its Association with High Density Lipoprotein," *J. Biol. Chem.* 272(28):17511-17522.
Liadaki et al. (Jul. 2000) "Binding of High Density Lipoprotein (HDL) and Discoidal Reconstituted HDL to the HDL Receptor Scavenger Receptor Class B Type I. Effect of Lipid Association and apoA-I Mutations on Receptor Binding," *J. Biol. Chem.* 275(28):21262-21271.
Liu et al. (Jul. 2004) "A Hybrid Fibronectin Motif Protein as an Integrin Targeting Selective Tumor Vascular Thrombogen," *Mol. Cancer. Ther.* 3(7):793-801.
Liu et al. (Oct. 1, 2002) "Prostate-Specific Membrane Antigen Directed Selective Thrombotic Infarction of Tumors," *Cancer Res.* 62:5470-5475.
Mammen et al. (2006) "Myoglobin [*Mus musculus*]," NCBI Accession No. NP_038621.
Marcel et al. (1998) "Definition of Apolipoprotein A-I Domains Involved in Reverse Cholesterol Transport," *International Congress Series* 1155(Atherosclerosis XI) 1149-1153.
Marheineke et al. (1998) "Lipid Composition of *Spodoptera frugiperda* (Sf9) and *Trichoplusia ni* (Tn) Insect Cells Used for Baculovirus Infection," *FEBS Lett.* 441:49-52.
McGregor, C.L. (Feb. 2003) "Lipopeptide Detergents Designed for the Structural Study of Membrane Proteins," *Nat. Biotechnol.* 21:171-176.
McManus et al. (Feb. 2000) "Distinct Central Amphipathic α-Helices in Apolipoprotein A-I Contribute to the in Vivo Maturation of High Density Lipoprotein by Either Activation Lechithin-Cholesterol Acyltransferase or Binding Lipids," *J. Biol. Chem.* 275(7):5043-5051.
Midathada et al. (2004) "Recombinant Factor VIIa in the Treatment of Bleeding," *Am. J. Clin. Pathol.* 121:124-137.
Miller et al. (1996) "X-Ray Diffraction Analysis of Cytochrome P450 2B4 Reconstituted into Liposomes," *Biochemistry* 35:1466-1474.
Mimms et al. (1981) "Phospholipid Vesicle Formation and Transmembrane Protein Incorporation Using Octyl Glucoside," *Biochemistry* 20:833-840.
Minnich et al. (1992) "Site-Directed Mutagenesis and Structure-Function Analysis of the Human Apolipoprotein A-I. Relation Between Lecithin-Cholesterol Acyltransferase Activation and Lipid Binding," *J. Biol. Chem.* 267(23):16553-16560.
Morrissey, J.H. (2001) "Tissue Factor and Factor VII Initiation of Coagulation," In; *Hemostasis and Thrombosis: Basic Principles and Clinical Practice*, 4th ed., Colman et al. Eds., Lippincott Williams and Wilkins, Philadelphia, pp. 89-101.
Mukhopadhyay et al. (Mar. 31, 2000) "A Scanning Tunneling Microscopy Study of *Clostridium pasteurianum* rubredoxin," *J. Inorq. Biochem.* 78:2337-2346.
Mulder et al. (1996) "Association of Endothelial Tissue Factor and Thrombomodulin with Caveolae," *Blood* 88:1306-1313.
NCBI Accession No. P69905 (2007) "Hemoglobin Subunit Alpha (Hemoglobin Alpha Chain) (Alpha-Globin),".

Neuenschwander et al. (1995) "Phosphatidylethanolamine Augments Factor VIIa-Tissue Factor Activity: Enhancement of Sensitivity to Phosphatidylserine," *Biochemistry* 34:13988-13993.
Neuenschwander et al. (Jul. 15, 1992) "Deletion of the Membrane Anchoring Region of Tissue Factor Abolishes Autoactivation of Factor VII but Not Cofactor Function," *J. Biol. Chem.* 267(20):14477-14482.
Neuenschwander et al. (Mar. 18, 1994) "Roles of the Membrane-Interactive Regions of Factor VIIa and Tissue Factor," *J. Biol. Chem.* 269(11):8007-8013.
Neuffer et al. (2004) "Hemostatic Dressings for the First Responder: A Review," *Mil. Med.* 169:716-720.
Nilsson et al. (Jan. 15, 2001) "Targeted Delivery of Tissue Factor to the ED-B Domain of Fibronectin, a Marker of Angiogenesis, Mediates the Infarction of Solid Tumors in Mice," *Cancer Res.* 61:711-716.
Okumura et al. (2004) "Hemoglobin Beat Chain Complex [*Rattus norvegicus*]," NCBI Acession No. NP_150237.
Paborsky et al. (1989) "Purification of Recombinant human Tissue Factor," *Biochemistry* 28:8072-8077.
Paborsky et al. (Nov. 15, 1991) "Lipid Association, but Not the Transmembrane Domain, Is Required for Tissue Factor Activity," *J. Biol. Chem.* 266(32):21911-21916.
Phillips et al. (1997) "Predicting the Structure of Apolipoprotein A-I in Reconstituted High-Density Lipoprotein Disks," *Biophys. J.* 73:2337-2346.
Poon, M. (2001) "Use of Recombinant Factor VIIa in Hereditary Bleeding Disorders," *Curr. Opin. Hematol.* 8:312-318.
Pusateri et al. (2003) "Effect of Chitosan-Based Hemostatic Dressing on Blood Loss and Survival in a Model of Severe Venous Hemorrhage and Hepatic Injury in Swine," *J. Trauma* 54: 177-182.
Pusateri et al. (Sep. 2003) "Advanced Hemostatic Dressing Development Program: Animal Model Selection Criteria and Results of a Study of Nine Hemostatic Dressings in a Model of Severe Large Venous Hemorrhage and Hepatic Injury in Swine," *J. Trauma* 55:518-526.
Ran et al. (Oct. 15, 1998) "Infarction of Solid Hodgkin's Tumors in Mice by Antibody-Directed Targeting of Tissue Factor to Tumor Vasculature," *Cancer Res.* 58:4646-4653.
Rayner et al. (2005) "Myoglobin [*Homo sapiens*]," NCBI Accession No. NP_005359.
Reardon et al. (Oct. 2001) "In Vivo Studies of HDL Assembly and Metabolism Using Adenovirus-Mediated Transfer of ApoA-I Mutants in ApoA-I-Deficient Mice," *Biochemistry* 40(45):13670-13680.
Rezaie et al. (1992) "Expression and Purification of a Soluble Tissue Factor Protein with an Epitope for an Unusual Calcium-Dependent Antibody," *Protein Expr. Purif.* 3:453-460.
Rippmann et al. (2000) "Fusion of the Tissue Factor Extracellular Domain to a Tumor Stroma Specific Single-Chain Fragment Variable Antibody Results in an Antigen-Specific Coagulation-Promoting Molecule," *Biochem. J.* 349:805-812.
Robinson et al. (1998) "Changes in Solvation During DNA Binding and Cleavage are Critical to Altered Specificity of the *EcoRI* Endonuclease," *Proc. Nat. Acad. Sci. USA* 95:2186-2191.
Robinson et al. (May 1998) "Optimizing the Stability of Single-Chain Proteins by Linker Length and Composition Mutagenesis," *Proc. Nat. Acad. Sci. USA* 95(11):5929-5934.
Rogers et al. (1997) Truncation of the Amino Terminus of Human Apolipoprotein A-I Substantially Alters Only the Lipid-Free Conformation, *Biochemistry* 36(2):288-300.
Rogers et al. (1998) "Structural analysis of Apolipoprotein A-I: Effects of Amino-And Carboxyl-Terminal Deletions on the Lipid-Free Structure," *Biochemistry* 37:945-955.
Rogers et al. (1998) "The Lipid-Free Structure of Apolipoprotein A-I: Effects of Amino-Terminal Deletions," *Biochemistry* 37(34):11714-11725.
Rosseneu et al. (1992) "Contribution of Helix-Helix Interactions to the Stability of Apolipoprotein-Lipid Complexes," *International Congress Series* 1001(High Density Lipoproteins Atheroscler. III):105-114.
Ruoslahti (Nov. 15, 2002) "Drug Targeting to Specific Vascular Sites," *Drug Discov. Today* 7(22):1138-1143.

Salamon, Z. (1997) "Coupled Plasmon—Waveguide Resonators: A New Spectroscopic Tool for Probing Proteolipid Film Structure and Properties," *Biophys. J.* 73:2791-2797.

Savelli et al. (2000) "Enzyme Activity and Stability Control by Amphiphilic Self-Organizing Systems in Aqueous Solutions," *Curr. Opin. Colloid and Interface Sci.* 5:111-117.

Schafmeister et al. (1993) "Structure at 2.5 Å of a Designed Peptide that Maintains Solubility of Membrane Proteins," *Science* 262:734-738.

Schonauer et al. (2004) "The Use of Local Agents: Bone Wax, Gelatin, Collagen, Oxidized Cellulose," *Eur. Spine. J.* 13 Supp.1:S89-S96.

Schexneider, K.I. (2004) "Fibrin Sealants in Surgical or Traumatic Hemorrhage," *Curr. Opin. Hematol.* 11:323-326.

Scott et al. (Dec. 2001) "The N-Terminal Globular Domain and the First Class A Amphipathic Helix of Apolipoprotein A-I are Important for Lecithin: Cholesterol Acyltransferase Activation and the Maturation of High Density Lipoprotein in Vivo," *J. Biol. Chem.* 276(52):48716-48724.

Segrest et al. (Nov. 5, 1999) "A Detailed Molecular Belt Model for Apolipoprotein A-I in Discoidal High Density Lipoprotein," 274(45):31755-31758.

Shaw et al. (Jan. 2004) "Phospholipid Phase Transitions in Homogeneous Nanometer Scale Bilayer Discs," *FEBS Lett.* 556:260-264.

Shaw et al. (Mar. 2, 2007) "The Local Phospholipid Environment Modulates the Activation of Blood Clotting," *J. Biol. Chem.* 282(9):6556-6563.

Shiva et al. (2007)"Myoglobin [*Rattus novegicus*]," NCB Accession No. NP_067599.

Sirlak et al. (2003) "Comparative Study of Microfibrillar Collagen Hemostat (Colgel) and Oxidized Cellulose (Surgical) in High Transfusion-Risk Cardiac Surgery," *J. Thorac. Cardiovasc. Surg.* 126:666-670.

Sklar et al. (May. 2000) "Solubilization and Display of G Protein-Coupled Receptors on Beads for Real-Time Fluorescence and Flow Cytometric Analysis," *BioTechniques* 28(5):976-985.

Skulachev, V.P. (1982) "A Single Turnover Study of Photoelectric Current0Generating Proteins," *Methods Enzymol.* 88:35-45.

Sligar, S. (2003) "Finding a Single-Molecule Solution for Membrane Proteins," *Biochem. Biophys. Res. Comm.* 312:115-119.

Smeets et al. (1996) "Contribution of Different Phospholipid Classes to the Prothrombin Converting Capacity of Sonicated Lipid Vesicles," *Thromb. Res.* 81:419-426.

Smith et al. (2004) "Rapid and Efficient Incorporation of Tissue Factor into Liposomes," *J. Thromb. Haemost.* 2:1155-1162.

Smith et al. (2004) "Properties of Recombinant Human Thromboplastin That Determine the International Sensitivity Index (ISI)," *J. Thromb. Haemosst.* 2:1610-1616.

Soffer et al. (May 2003) "Fibrin Sealants and Platelet Preparations in Bone and Periodontal Healing," *Oral Surg. Oral Med. Oral Pathol. Oral Radiol. Endod.* 95(5):521-528.

Sorci-Thomas et al. (1998) "The Hydrophobic Face Orientation of Apolipoprotein A-I Amphipathic Helix Domain 143-164 Regulates Lecithin: Cholesterol Acyltransferase Activation," *J. Biol. Chem.* 273(19):11776-11782.

Sorci-Thomas et al. (1997) "Alteration in Apolipoprotein A-I 22-Mer Repeat Order Results in a Decrease in Lecithin: Cholesterol Acyltransferase Activity," *J. Biol. Chem.* 272(11):7278-7284.

Sviridov et al. (1996) "Identification of a Sequence of Apolipoprotein A-I Associated with the Activation of Lecithin: Cholesterol Acyltransferase," *J. Biol. Chem.* 275(26):19707-19712.

Sviridov et al. (1996) "Efflux of Cellular Cholesterol and Phospholipid to Apolipoprotein A-I Mutants," *J. Biol. Chem.* 271(52):33277-33283.

Thorpe et al. (2000) "Tumor Infarction by Targeting Tissue Factor to Tumor Vasculature," *Cancer J.* 6 Supp.3:S237-S244.

Tocanne et al. (1994) "Lipid Domains and Lipid/Protein Interactions in Biological Membranes," *Chem. Phys. Lipids* 73:139-158.

Trail et al. (May 2003) "Monoclonal Antibody Drug Immunoconjugates for Targeted Treatment of Cancer," *Cancer Immunol. Immunother.* 52(5):328-337.

van Voorst et al. (Dec. 2000) "The High Affinity ATP Binding Site Modulates the SecA-Precursor Interaction," *FEBS Lett.* 486(1):57-62.

Wald et al. (1990) "Investigation of the Lipid Domains and Apolipoprotein Orientation in Reconstituted High Density Lipoproteins by Fluorescence and IR Methods," *J. Biol. Chem.* 265(32):20044-20050.

Wald et al. (1990) "Structure of Apolipoprotein A-I in Three Homogeneous, Reconstituted High Density Lipoprotein Particles," *J. Biol. Chem.* 265(32):20037-20043.

Waner M. (2004) "Novel Hemostatic Alternatives in Reconstructive Surgery," *Semin. Hematol.* 41:163-167.

Wang et al. (1997) "Three-Dimensional Structure of NADPH-Cytochrome P4510 Reductase: Prototype for FMN and FAD-Containing Enzymes," *Proc. Nat. Acad. Sci.* USA 49:8411-8416.

Wlodawer et al. (1979) "High-Density Lipoprotein Recombinants: Evidence for a Bicycle Tire Micelle Structure Obtained by Neutron Scattering and Electron Microscopy," *FEBS Lett.* 104(2):231-235 Segr35.

Wright et al. (2004) "Thermal Injury Resulting from Application of a Granular Mineral Hemostatic Agent," *J. Trauma* 57:224-230.

Yasui et al. (Dec. 2, 2003) "Collagen-Protein Interactions Mapped by Phototriggered Thiol Introduction," *J. Am. Chem. Soc.* 125(51):15728-15729.

Zuch et al. (Sep. 1999) "Ligand-Receptor Binding Measured by Laser-Scanning Imaging," *Proc. Nat. Acad. Sci. USA* 96:11122-11127.

Carson et al. (1981) "Coagulation Factor III (Tissue Factor) Interaction with Phospholipid Vesicles Induced by Cadmium: Characterization of the Reconstituted Protein-Membrane Complex," *Biosci. Rep.* 1:197-205.

International Search Report and Written Opinion, Corresponding to International Application No. PCT/US05/38781, Mailed Jun. 6, 2006.

International Preliminary Report on Patentability, corresponding to International Application No. PCT/US05/38781, mailed May 10, 2007.

McCallum et al. (Nov. 28, 1997) "Tissue Factor Positions and Maintains the Factor VIIa Active Site far above the Membrane Surface even in the Absence of the Factor VIIa Gla Domain," *J. Biol. Chem.* 72(48):30160-30166.

* cited by examiner

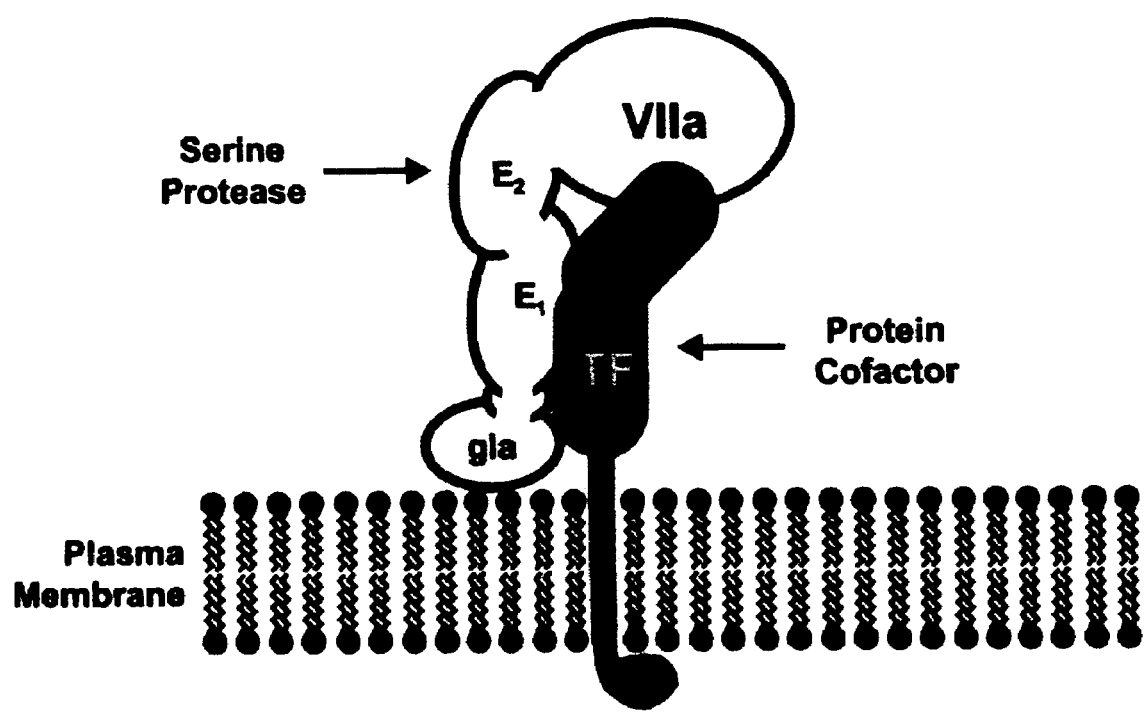
FIGURE 1A - PRIOR ART

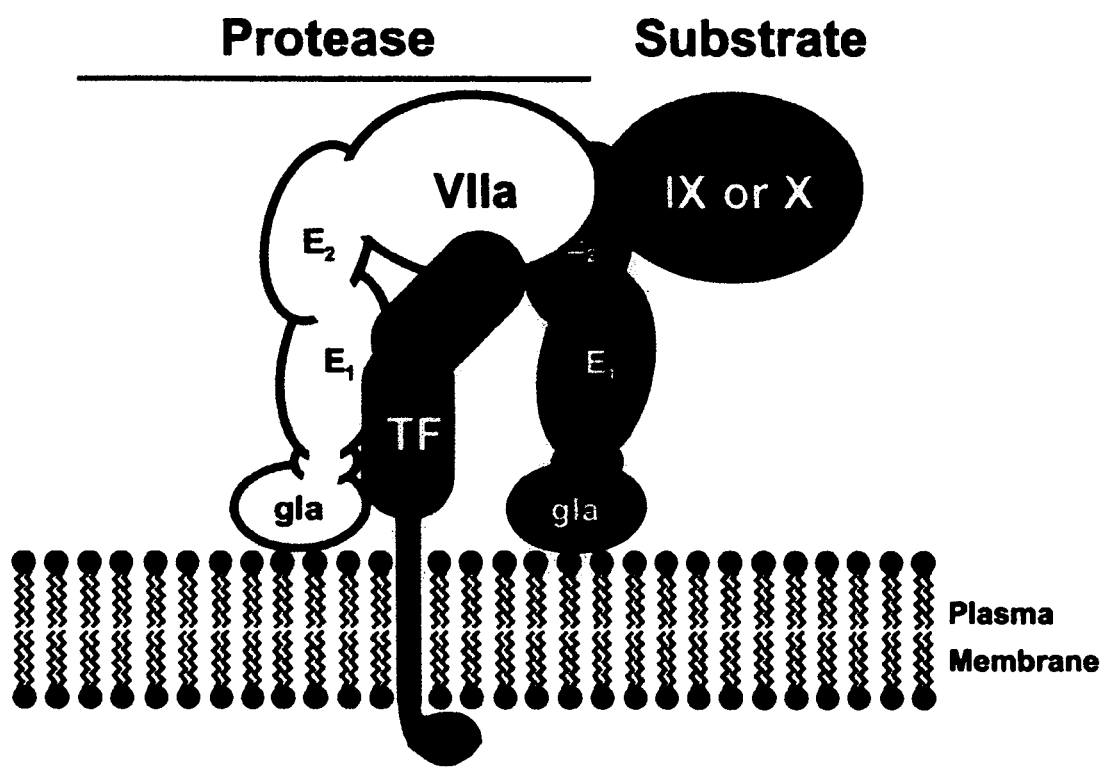
FIGURE 1B - PRIOR ART

TISSUE FACTOR COMPOSITIONS AND METHODS

CROSS-REFERENCE TO RELATED APPLICATIONS

This application claims benefit of U.S. Provisional Application No. 60/622,737, filed Oct. 27, 2004, and is a Continuation-in-Part of U.S. patent application Ser. No. 11/033,489, filed Jan. 11, 2005, which claims benefit of U.S. Provisional Application 60/536,281, filed Jan. 13, 2004 and is a Continuation-in-Part of U.S. patent application Ser. No. 10/465,789, filed Jun. 18, 2003, which is a Continuation-in-Part of U.S. patent application Ser. No. 09/990,087, filed Nov. 20, 2001, which claims benefit of U.S. Provisional Application No. 60/252,233, filed Nov. 20, 2000. All prior applications are incorporated by reference in their entireties to the extent there is no inconsistency with the present disclosure.

STATEMENT REGARDING FEDERALLY SPONSORED RESEARCH OR DEVELOPMENT

This invention was made with government support under Grant Nos. GM33775 and R01 HL 47014 awarded by the National Institutes of Health. The government has certain rights in the invention.

BACKGROUND OF THE INVENTION

The field of this invention is the area of therapeutic nanoscale particulate compositions, in particular to formulations of improved solubility and stability for the delivery of tissue factor. These formulations can be used to kill tumors, to stop bleeding, as topical hemostatic agents and as reagents in prothrombin time assays.

Tissue factor (TF) is the integral membrane protein that triggers blood coagulation. TF is composed of two fibronectin type 3 domains, a single membrane-spanning domain, and a short cytoplasmic domain (FIG. 1A). TF is typically expressed on the cell surface. A type I integral membrane protein, TF has its N-terminus located outside the cell and its C-terminus is in the cytoplasm.

TF is abundant in adventitial cells, found exterior to the smooth muscle of blood vessels. This layer can be considered a hemostatic envelope (Drake et al. 1989. Amer. J. Pathol. 134:1087-1097). Where there is damage to a blood vessel, TF participates in the clotting cascade to form a "patch" to stop further blood loss from the vasculature. Where blood vessels contain plaque and there is a rupture of the plaque, TF participates in the formation of a hemostatic "patch" at the point of rupture. This serves as a focus for clotting, leading to further occlusion of the blood vessel at that location.

TF functions to initiate blood clotting by selectively binding one of the soluble plasma proteins (factor VII or the activated form, factor VIIa) with high affinity. This results in the formation of TF:VIIa complexes on the cell surface. Factor VIIa, the first enzyme in the blood clotting cascade, is a serine protease that circulates as a soluble protein in the plasma. Factor VIIa is an extremely weak enzyme (low activity) unless it is bound to its protein cofactor (TF). Factor VIIa is allosterically activated when it binds TF, creating an extremely potent, two subunit enzyme (TF:VIIa). The TF:VIIa complex then triggers blood clotting by proteolytically activating two plasma serine protease zymogens (factors IX and X), which then go on to propagate the clotting cascade. The ultimate result is the formation of blood clots composed of polymerized fibrin and activated platelets. TF is thought to be involved in thrombotic diseases in addition to its beneficial role in preventing blood loss from the vasculature.

Structurally, TF is a type I integral membrane protein composed of an extracellular domain, a single membrane-spanning domain and a short cytoplasmic tail. TF must be incorporated into suitable phospholipid membranes in order to exhibit maximal activity. Soluble TF is thousands of times less active than TF embedded in a suitable membrane, underscoring the essential role of membrane anchoring for TF function. In order for TF to exhibit strong procoagulant activity, the membrane or disc in which it is embedded must contain negatively charged phospholipids, desirably phosphatidylserine. There are several methods available for incorporating purified TF into phospholipid vesicles and nanoscale disc-like structures of varying composition.

Nanoscale disc-like particles comprising a membrane scaffold protein (MSP, naturally occurring or engineered) and phospholipid have been successfully used to provide stable, soluble and biologically active hydrophobic proteins. See, for example, WO 02/40501 and US Published Applications 2004/0053384 and 2005/0182243 for a thorough discussion of these particles, the structural proteins in them and their formation. These particles contain the phospholipid in the form of a disc which is surrounded by a "belt" formed of the amphiphilic membrane scaffold protein (MSP). Where there is a hydrophobic protein incorporated, it is bound in, within or to the phospholipid portion and may or may not have peripheral association with the encircling MSP. These particles are typically from about 5 to about 50 nm, usually about 5 to about 20 nm, in diameter, depending on the specific composition.

SUMMARY OF THE INVENTION

It is an object of the present invention to provide improved compositions comprising tissue factor, including but not limited to human tissue factor, which compositions are improved in stability, solubility and handling characteristics. As specifically exemplified herein, tissue factor is incorporated into nanoscale particles comprising at least one membrane scaffold protein and phospholipid, desirably but not necessarily including at least one net negatively charged phospholipid. Desirably, the phospholipid is phosphatidylserine (PS) and phosphatidylcholine (PC) at a molar ratio of 1:99 to 50:50, or from 5:95, 10:40 or 20:80. If phosphatidylethanolamine (PE) is present instead of PC, then the proportion of PS or other net negatively charged phospholipid can be lower. Where a net negatively charged phospholipid is incorporated, it can make up from 1 to 50% (molar basis) of the total phospholipid. The membrane scaffold protein can be a naturally occurring protein such as apolipoprotein A1, apolipoprotein C or E, or other predominantly amphipathic helical protein, or it can be any of a number of engineered (designed and produced by the hand of man) membrane scaffold proteins, for example as described in United States Patent Publications 2005/0182243 and 2004/0053384, both of which are incorporated by reference to the extent there is no inconsistency with the present disclosure. For coding and amino acid sequences of MSPs useful in the practice of the present invention, see Tables 4-56 herein below. Specifically exemplified MSPs include, but are not limited to, SEQ ID NO:2, SEQ ID NO: 4, SEQ ID NO:6, SEQ ID NO:8, amino acids 13-414 of SEQ ID NO:8, SEQ ID NO:10, amino acids 13-422 of SEQ ID NO:10, SEQ ID NO:12, amino acids 13-168 of SEQ ID NO:12, SEQ ID NO:14, amino acids 13-168 of SEQ ID NO:14, SEQ ID NO:16, amino acids 13-201 of SEQ ID NO:16, SEQ ID NO:17, amino acids 13-201 of SEQ ID NO:17, SEQ ID NO:18, amino acids 13-392 of SEQ ID NO:18, SEQ ID
NO:50, amino acids 13-234 of SEQ ID NO:50, SEQ ID
NO:51, amino acids 13-256 of SEQ ID NO:51, SEQ ID
NO:52, amino acids 13-278 of SEQ ID NO:52, SEQ ID
NO:53, amino acids 24-223 of SEQ ID NO:53, SEQ ID
NO:54, SEQ ID NO:55, amino acids 24-212 of SEQ ID
NO:55, SEQ ID NO:56, SEQ ID NO:57, amino acids 24-201
of SEQ ID NO:57, SEQ ID NO:58, amino acids 13-190 of
SEQ ID NO:58, SEQ ID NO:59, amino acids 13-201 of SEQ
ID NO:59, SEQ ID NO:60, amino acids 13-190 of SEQ ID
NO:60, SEQ ID NO:61, amino acids 24-201 of SEQ ID
NO:61, SEQ ID NO:62, amino acids 24-190 of SEQ ID
NO:62, SEQ ID NO:63, amino acids 24-179 of SEQ ID
NO:63, SEQ ID NO:64, amino acids 24-289 of SEQ ID
NO:64, SEQ ID NO:65, amino acids 24-289 of SEQ ID
NO:64, SEQ ID NO:65, amino acids 24-278 of SEQ ID
NO:65, SEQ ID NO:66, amino acids 24-423 of SEQ ID
NO:66, SEQ ID NO:67, amino acids 24-199 of SEQ ID
NO:67, SEQ ID NO:68, amino acids 24-401 of SEQ ID
NO:68, SEQ ID NO:69, amino acids 24-392 of SEQ ID
NO:69, SEQ ID NO:81, amino acids 24-397 of SEQ ID
NO:81, SEQ ID NO:83, amino acids 24-383 of SEQ ID
NO:83, SEQ ID NO:85, amino acids 24-379 of SEQ ID
NO:85, SEQ ID NO:87, amino acids 24-381 of SEQ ID
NO:87, SEQ ID NO:89, amino acids 25-212 of SEQ ID
NO:89, SEQ ID NO:91, amino acids 25-212 of SEQ ID
NO:91, SEQ ID NO:93 and amino acids 13-212 of SEQ ID
93.

The molar ratio of phospholipid to membrane scaffold protein to tissue factor or truncated recombinant tissue factor in the mixture from which the nanoscale particles are prepared can be from about 45:1:0.1 to about 80:1:0.1, desirably about 50:1:0.1 to 70:1:0.1, or 65:1:0.1, where the membrane scaffold protein in MSP1, rTF and a 20:80 molar ratio of PS:PC. Other phospholipid mixtures can comprise net-negative charged phospholipids (including but not limited to PS) present from 1 to 50, from 3 to 50, from 10 to 40 or 20, on a mol % basis, with the balance being net-neutral phospholipids such as phosphatidylcholine (PC) or phosphatidylethanolamine (PE). In the specifically exemplified case where an MSP is larger than MSP1, for example MSP1E3D1, then a higher molar ratio of lipid to MSP is used (from 70:1 to 140:1, from 90:1 to 125:1, or from 115:1). It is understood that if more than one TF (or rTF) molecule per nanoscale particle is acceptable the ratio of that TF or rTF in the preparation mixture can be higher than those specified above.

It is a further object of the present invention to provide tissue factor-containing compositions useful as topical hemostatic agents. These compositions comprise tissue factor incorporated into nanoscale particles as described above. The topical hemostatic agent can be applied to a site of trauma in a human or animal patient, or it can be applied to a surgical incision, a site of post-surgical bleeding, soft tissue trauma or to patient afflicted with hemophilia or thrombocytopenia, in an amount sufficient to control bleeding in the patient. The nanoparticles containing the tissue factor can be attached to or adsorbed onto a solid support such as to a collagen sponge or netting, or microcrystalline collagen powder, which is convenient for use at a surgical or trauma locus. Alternatively, such nanoparticles can be attached to a solid support such as beads or coated onto biologically inert particles or to materials such as ground chitin, chitosan or chitosan derivatives, which can then be applied at a trauma site in a patient or introduced into a solid tumor. In some embodiments, tissue factor is attached to solid supports so that it will not be allowed to migrate freely into and/or throughout the bloodstream, and so that it will not be washed out of a wound by hemorrhaging blood. Alternatively, the TF-containing particles can be embedded in a slow release composition.

The present invention provides a useful therapeutic composition to supplement a deficiency in the clotting system in a human or animal patient, for example, as a result of a genetic or acquired deficiency, due to chemotherapy, or as a result of inhibitory antibodies. Desirably, the tissue factor and the membrane scaffold protein in the nanoparticles are from the same species as the patient to which the composition is administered.

It is another object of the invention to provide a method for stopping bleeding in a human or animal patient, said method comprising the step of administering a therapeutic composition comprising tissue factor-containing nanoscale particles as described above to the patient in need of said treatment, in an amount sufficient to control or stop bleeding in said patient. Advantageously, the TF-containing particles are immobilized on a solid support so that migration into the bloodstream or loss of the particles from the wound site is limited.

It is further object of the invention to provide a method for killing or inhibiting growth of a tumor in a human or animal patient, said method comprising the step of administering a therapeutic composition comprising tissue factor-containing nanoscale particles as described above to the patient in need of said treatment. The tumor can be a neoplastic growth in the patient. Especially in this method, the particles further comprise a targeting agent which specifically binds to the tumor cells and tissue, including but not limited to a lectin an antibody, single chain body, or an antigen-binding antibody fragment.

It is yet another object of the invention to provide a reagent for use in prothrombin time assays, specifically nanoscale particles comprising tissue factor, as described above.

BRIEF DESCRIPTION OF THE DRAWINGS

FIG. 1A (prior art) diagrammatically illustrates the catalytically active, membrane-bound complex of TF and factor VIIa. FIG. 1B diagrammatically illustrates the TF:VIIa complex bound to factor IX or X, which is activated by the proteolytic action of the TF:VIIa complex bound to the membrane.

FIG. 1B (prior art) shows the complex of Factor VIIa, TF and Factor IX or X with the relative position of the membrane.

DETAILED DESCRIPTION OF THE INVENTION

Figure 2:
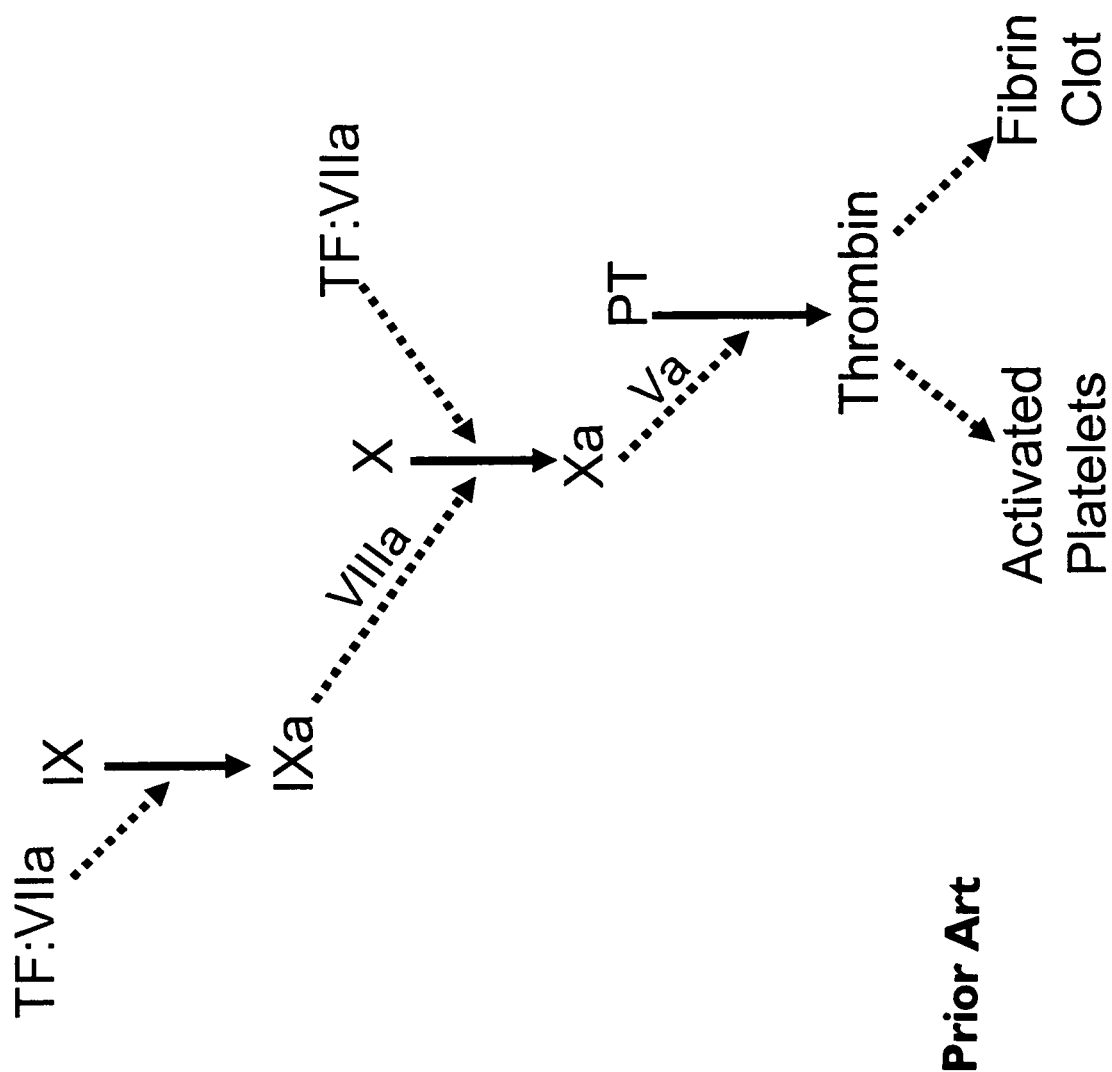
FIG. 2 (prior art) is a simplified schematic of the clotting cascades, with the two action points of the TF:VIIa complex shown.
Figure 3:
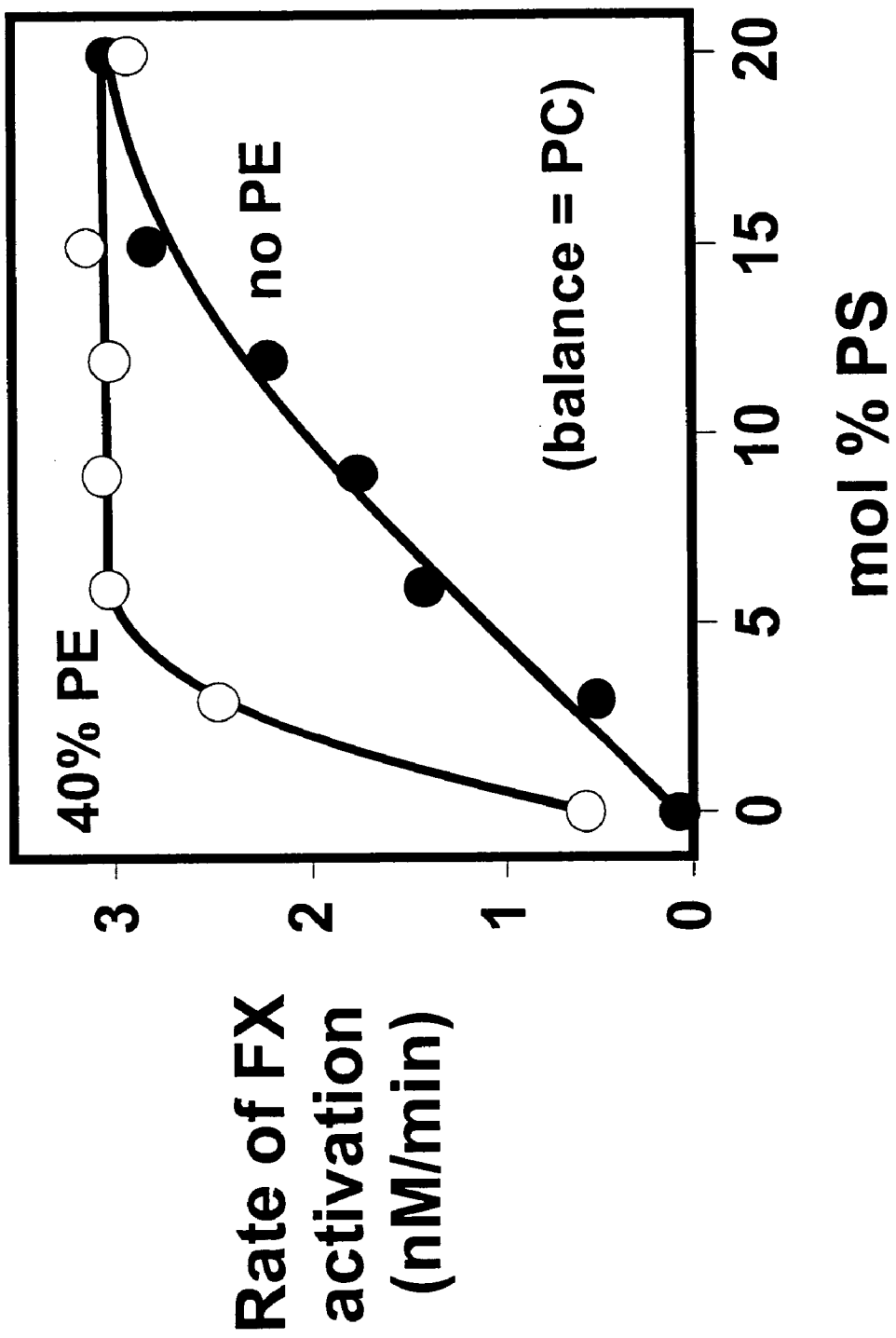
FIG. 3 (prior art, Neuenschwander and Morrissey. 1993. Biochemistry 34:13988-13993) shows the response of TF:VIIa to the phospholipid content.
Figure 4B:
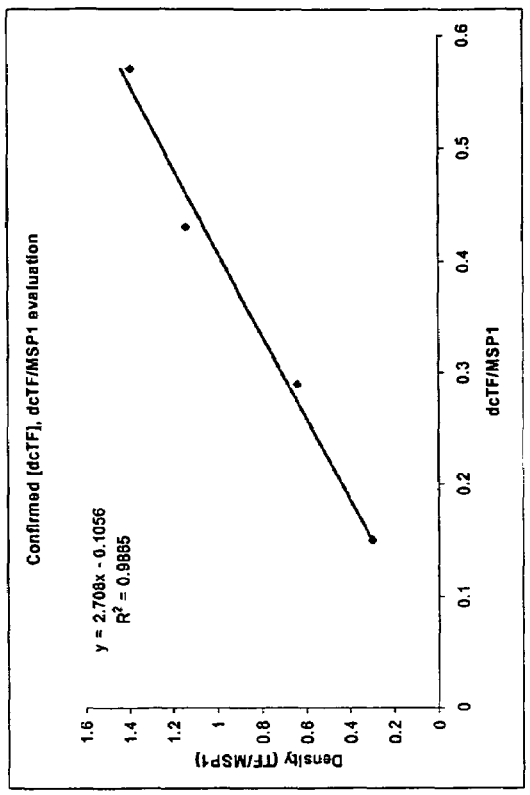
FIG. 4B shows that the ratio of TF:MSP1 is 0.51 in the nanoscale particle preparation.
Figure 4A:
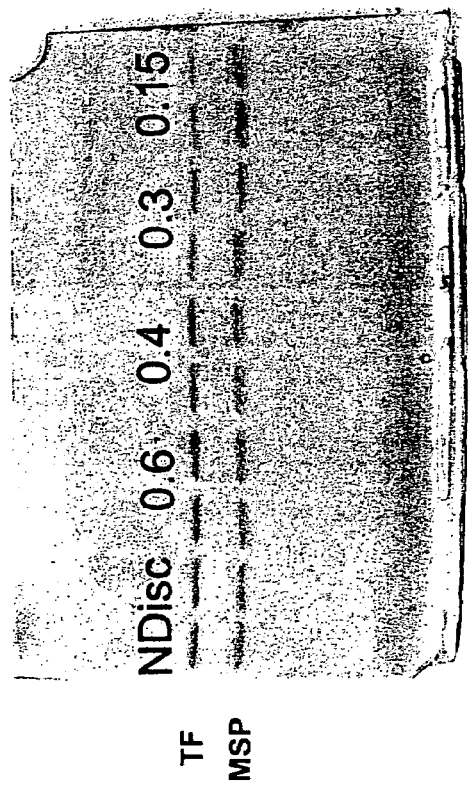
FIG. 4A shows the results of sodium dodecyl sulfate polyacrylamide gel electrophoresis of solubilized TF-containing, MSP1-supported nanoscale disc-like particles purified by HPLC, where those particles were prepared under different conditions.

Abbreviations used herein include DOPC, 1,2-dioleoyl-sn-glycero-3-phosphocholine; DOPS, 1,2-dioleoyl-sn-glycero-3-phosphoserine; DPPC, 1,2-dipalmitoyl-sn-glycero-phosphocholine; Gla, γ-carboxyglutamate; Gla-domain, Gla-rich domain; PC, phosphatidylcholine; PCPS, vesicles composed of mixtures of PC and PS, typically 80% PC, 20% PS; PE, phosphatidylethanolamine; PS, phosphatidylserine; SPR, surface plasmon resonance; sTF, soluble TF (extracellular domain of TF); TF:VIIa, the 1:1 complex of TF and factor VIIa; rTF, recombinant trucnated TF; PL, phospholipid; POPC, palmitoyl-oleoyl-sn-glycero-3-phosphatidylcholine; POPS, palmitoyl-oleoyl-sn-glycero-3-phosphatidylserine.

Tissue factor (TF) is the integral membrane protein that triggers blood coagulation (Morrissey, J H. Tissue Factor and Factor VII Initiation of Coagulation. In: Hemostasis and Thrombosis: Basic Principles and Clinical Practice (Fourth Edition), R W Colman, J Hirsh, V J Marder, A W Clowes, and J N George, eds. (Lippincott Williams & Wilkins, Philadelphia), pp 89-101, 2001). TF is composed of two fibronectin type 3 domains, a single membrane-spanning domain, and a short cytoplasmic domain (FIG. 1A). TF is typically expressed on the cell surface. A type I integral membrane protein, TF has its N-terminus located outside the cell and its C-terminus is in the cytoplasm.

Membrane (or Matrix) Scaffold Proteins (MSPs) as used herein may be naturally occurring, recombinant or artificial (do not occur in nature) amphiphilic proteins which self-assemble phospholipids and phospholipid mixtures into nanometer size membrane bilayers. A subset of these nanometer size assemblies are discoidal in shape, and are referred to as nanoscale discs or nanoscale disc-like particles. Typical nanoscale disc-like particles are from about 9 to about 13 nm in diameter. Such particles comprise about 65 to about 120 phospholipid molecules per side, ringed by one or more amphipathic membrane scaffold proteins, also call matrix scaffold protein. Desirably the MSPs comprise several helical domains, wherein successive helical domains are separated by a punctuation region, made up of one to five amino acids which do not favor helix formation or which tend to stop helix formation of adjacent amino acids. These assembled structures of MSP and phospholipid preserve the overall bilayer structure of normal membranes but provide a system which is both soluble in solution and can be assembled or affixed to a variety of surfaces.

An example of a naturally occurring MSP is apolipoprotein A1. In addition, MSPs can be designed using helical segments of proteins other than human apolipoprotein A-1, for example, apo A-1 of other species, or apo C, apo E, myoglobin or hemoglobin proteins of various species. Helical segments from more than one protein can be combined, with the appropriate punctuation sequences (where the punctuation sequence confers flexibility it can also be called a hinge region or hinge sequence) to form an MSP having the useful properties described herein. See Tables 4-56 below for specifically exemplified MSPs and their coding sequences. Additionally, functional MSPs can be generated by de novo protein design wherein the desired traits of amphipathic helical protein structures are produced. It is also understood that conservative amino acid substitutions can be made in the sequences specifically exemplified, with the proviso that the self-association function is maintained. Such substitution variants can be termed homologs of the specifically exemplified sequences. Various helix-forming, amphiphilic proteins of interest are described in Bolanos-Garcia et al. (2003) Progress in Biophys. Molec. Biol. 83:47-68.

It is also readily within the grasp of the skilled artisan to design other MSPs for packaging tissue factor (natural or truncated) proteins or complexes where the MSP assumes an amphiphilic conformation based on beta sheets, where the amino acid sequence of the protein is punctuated so that there are regions of beta sheet forming portions separated by a flexible region of amino acids. The region of beta sheet-forming sequence is desirably from about 10 to about 30 amino acids, and the punctuation region can include from 3 to 10 amino acids, where there are antiparallel beta sheets in the MSP or from about 10 to about 30 amino acids where the beta sheets are parallel.

Functional MSPs may or may not have punctuation regions between domains of secondary structure within the protein. The punctuation region disrupts regions of secondary structure within a protein. Proline and/or glycine residues are preferred punctuation regions in a protein having helical domains. Besides disrupting a domain with a particular characteristic secondary structure, the punctuation regions can provide flexibility to the structure of a protein, especially in the case of two to three amino acids, desirably including glycine and alanine residues. A punctuation region (or sequence) can include from 5 to 30 amino acids, especially 1 or 2 when the secondary structure elements or domains are alpha helices and 3 to 10, where there are antiparallel beta sheets in the MSP.

Sequences of several apolipoproteins, hemoglobins and myoglobins are available on the internet at the site of The National Center for Biotechnology Information (NCIB), National Institutes of Health. The coding sequences can be found on the internet and used in the construction of artificial MSP coding sequences or the sequences can be tailored to optimize expression in the recombinant host cell of choice. There is a large body of information about codon choice and nontranslated sequences in the art. Apolipoprotein C sequences include, without limitation, bovine, XP 77416; mouse, AAH 28816; human NP 000032; and monkey, Q28995. Myoglobin sequences include, for example, those of mouse, NP 038621; bovine, NP 776306; rat, NP 067599; and human, NP 005359. Hemoglobin alpha chain sequences include human, AAH 32122 or NP 000549; beta chain sequences include human, NP 000509 or PO20203; rat, NP 150237; mouse NP032246; bovine, NP 776342. Others may be found at the NCBI website and in the scientific literature.

As used herein, amphiphilic and amphipathic are used synonymously in reference to membrane scaffold proteins. An amphiphilic protein or an amphiphilic helical region of a protein is one which has both hydrophobic and hydrophilic regions.

The MSPs used in preparing the nanoscale disc-like particles of the present invention must be amphipathic, with one part of its structure more or less hydrophilic and facing the aqueous solvent and another part more or less hydrophobic and facing the center of the hydrophobic bilayer that is to be stabilized. The elements of secondary structure of the protein generate the hydrophilic and hydrophobic regions in three dimensional space. Examination of the basic biochemical literature reveals two candidate protein structures that can have this required amphipathic character: the helix and the pleated sheet. The MSPs useful in packaging TF into soluble and stable nanoscale discs have a helix as the fundamental amphipathic building block. Each MSP has an amino acid sequence which forms amphipathic helices with more hydrophobic residues (such as A, C, F, I, L, M, V, W or Y, using one letter abbreviations for amino acids as well known to the art) predominantly on one face of the helix and more polar or charged residues (such as D, E, N, Q, S, T, H, K or R and sometimes C) on the other face of the helix. In addition, each helical building block can be punctuated (but punctuation is not necessary) with residues such as proline (P) or glycine (G) periodically, which can introduce flexibility into the overall structure by interrupting the general topology of the helix. In one embodiment, these punctuations occur about every 20-25 amino acids to form "kinks" or to initiate turns to facilitate the "wrapping" of the MSP around the edge of a discoidal phospholipid bilayer. The punctuation region (or sequence) can include from one to 10 amino acids, especially 3 to 10 where there are antiparallel beta sheets in the MSP.

In order to generate smaller belts around the bilayer structure, the overall length of the helical building blocks can be reduced, and the punctuations may be introduced more frequently. The exact amino acid sequence can vary in the positioning and number of the hydrophobic amino acids within the designed linear sequence. Simple models in which either the helical axis is parallel or perpendicular to the normal of the nanoscale disc bilayer can be generated. To generate a disc with a diameter of roughly 10 nm, an MSP comprises about 12 to about 20 or more repeating units having this generalized amphipathic sequence. Preferably, this protein would be composed of amphipathic alpha helices each with a length of between 14 and 25 amino acids, punctuated in the linear sequence by a residue unfavorable for helix formation, such as proline or glycine or a sequence from about 1 to 5 amino acids which does not favor helix formation, which form small helical building blocks that stabilize the hydrophobic core of the phospholipid bilayer. A helix of about 20-25 amino acids (a small helical building block) has a length comparable to the thickness of a membrane bilayer. These small helical segments are linked together (punctuated) with from 0 to about 5, optimally 1 or 2, amino acid residues, especially G or P. To cover the edge of a 10 nm discoidal particle in either of the "belt" models presented, one would need between 10-20 such helices, with 16 being a useful number. Desirably, the helix contains from about 3 to about 18 amino acids per turn, and the type of helix can be an alpha, pi or 3,10 helix, among others. Helices with three to sixteen, three to eight, desirably three to four, amino acids per turn of the helix are useful in the present invention. An MSP of the present invention can comprise from 50 to 400 turns.

Secondary structure predictions can be determined using programs readily accessible to the art; see, for example, on the internet at the ExPASy proteomics server of the Swiss Institute of Bioinformatics. Guidance in predicting secondary structure is also given in publications such as Chou et al. (1974) Biochemistry 13:211, 222; Chou et al. (1978) Ann. Rev Biochem. 47:251-278; Fasman (1987) Biopolymers 26(supp.):S59-S79. Where there is a dimer or higher oligomer of a protein such as a 7-TM membrane protein or where more than one protein is to be incorporated within a single nanoscale disc, for example a reductase and a cytochrome, the MSP used is ideally capable of forming a nanoscale disc-like particle with a diameter greater than 9-10 nm. Many of the examples described herein utilize MSP1, but MSP1T2 and others can be used as well. See, e.g., U.S. Patent Publication 2004/0053384 or U.S. 2005/0182243 and herein below. The increasingly larger nanoscale discs are prepared using increasingly longer MSP sequences, such as MSP1E1, MSP1E2 or MSP1E3, with or without polyhistidine tags (see U.S. 2004/0053384 and U.S. 2005/0182243). MSP1 yields a particle 8.5 nm in diameter. MSP1E1 9.7 nm, MSP1E2, 10.9 nm and MspE3 12.1 nm, when assembled only with phospholipids. Concomitantly, the average number of DPPC (fully saturated phospholipid) molecules assembled in these particles increases from 164±2 for MSP1 particles to 334±12 for MSP1E3 particles. With the unsaturated phospholipids, e.g., POPC (1-palmitoyl-2-oleyoyl-sn-glycero-3-phosphocholine) the numbers of phospholipid molecules for MSP1 particles was 122±10 and for MSP1E3 particles there were 248±24 molecules per disc. Without wishing to be bound by theory, it is believed that using a larger rather than a smaller MSP results in TF-containing nanoscale with improved clotting, antitumor or hemostatic activity.

In an alternative embodiment, the engineered amphiphilic MSP contains regions of secondary structure in three dimensional space, such as parallel or antiparallel beta sheets, with spacer regions of appropriate length to allow association of hydrophobic regions with a target hydrophobic molecule which is protected from the aqueous milieu, and thus stabilized and solubilized.

As specifically exemplified herein, the compositions and methods of the present invention utilize recombinant human tissue factor (rTF) that has been expressed in, and purified from, *Escherichia coli*, although other forms of native tissue factor and recombinant tissue factor can be used. The human rTF used in the experiments described herein differs from wild-type human TF in several ways. First, a small peptide epitope (HPC4 epitope) has been added to the N-terminus of rTF for ease of purification (Rezaie et al. 1992. Protein Express. Purif. 3: 453-460). The presence of this epitope on the N-terminus of TF does not affect its function in blood clotting. Second, all but two of the amino acids in the cytoplasmic domain of TF have been deleted (this is also termed des-cyto-TF, dcTF or rTF). The reason for removing most of the cytoplasmic domain is that it causes problems in expression and purification of rTF. The cytoplasmic domain of TF is dispensable for TF clotting functions, so there is no harm in removing this portion of TF. (See FIGS. 1A-1B). Third, rTF expressed in bacteria lacks the N-linked carbohydrate chains normally found on human TF, but the carbohydrate chains are not required for TF procoagulant activity (Paborsky et al. 1989. Biochemistry 28:8072-8077).

In order for TF to have optimal activity, it must be embedded into a phospholipid (PL) membrane which contains net-negatively charged phospholipids (Neuenschwander et al. 1995. Biochemistry 34, 13988-13993). The most active negatively charged phospholipid is phosphatidylserine (PS), although other phospholipids with a net negative charge, e.g., phosphatidic acid, phosphatidylglycerol or phosphatidylinositol, can be used. However, it is not possible to prepare phospholipid bilayers composed of just PS or other net negatively charged phospholipid. Therefore, PS is mixed with a net-neutral phospholipid, usually phosphatidylcholine (PC). Typically, PS is used in these phospholipid mixtures at levels ranging from 3 to 50 mol %. Most commonly, the phospholipid preparations used in the present invention contain 20 mol % PS and 80 mol % PC. This mixture is referred to herein as PCPS. Other neutral phospholipids, such as phosphatidylethanolamine (PE), can be incorporated into the mixture in place of some of the PC. An example of such a mixture is 10 mol % PS, 40 mol % PE and 50 mol % PC. Phospholipids, purchased from Avanti Polar Lipids, Inc., Alabaster, Ala., are derived from natural sources, although synthetic phospholipids can also be used.

TF functions as the cell-surface binding protein (and essential protein cofactor) for coagulation factor VIIa (FVIIa). FVIIa is a trypsin-like plasma serine protease (see FIG. 2 for clotting cascade). TF binds to FVIIa with high affinity ($K_d$<50 pM) and with 1:1 stoichiometry. The TF:VIIa complex is the first enzyme in the extrinsic pathway of the blood clotting cascade, in which TF can be considered the regulatory subunit, and FVIIa the catalytic subunit. TF:VIIa activates the clotting cascade by converting two serine protease zymogens (factors IX and X) into active enzymes (factors IXa and Xa) via limited proteolysis.

The isolated extracellular domain of TF has been expressed and purified using recombinant means. This truncated protein is water-soluble, so it is often referred to as soluble tissue factor (sTF). sTF has drastically reduced procoagulant activity relative to membrane-anchored TF (Neuenschwander and Morrissey. 1992. J. Biol. Chem. 267: 14477-14482; Fiore, M. M et al. 1994. J. Biol. Chem. 269: 143-149; Paborsky et al. 1991. J. Biol. Chem. 266:21911-21916) This underscores the importance of the membrane surface in supporting the enzymatic activity of the TF:VIIa complex.

rTF can be incorporated into supported phospholipid bilayers (nanoscale disc-like particles) in such a way as to retain procoagulant activity. To do this, it was necessary to identify conditions under which TF could be reliably inserted into the nanoscale disc bilayer. In addition, it was necessary to incorporate a mixture of negatively charged phospholipids (in this case, a mixture of PC and PS) into the supported phospholipid bilayer to insure optimal activity, although activity can be modulated (i.e., dampened) by increasing the proportion of neutral phospholipids in the core of the particle.

Initial studies were carried out to optimize PCPS nanoscale disc assembly without rTF. Our first optimization studies were aimed at determining which molar ratios of phospholipids (PL) to scaffold protein (MSP1) yielded the most homogeneous preparations of nanoscale discs when using PCPS as phospholipid. A molar ratio of 65:1 (PL:MSP) gave satisfactory result, with quite homogeneous preparations of nanoscale discs, as judged by size-exclusion chromatography.

Figure 5A:
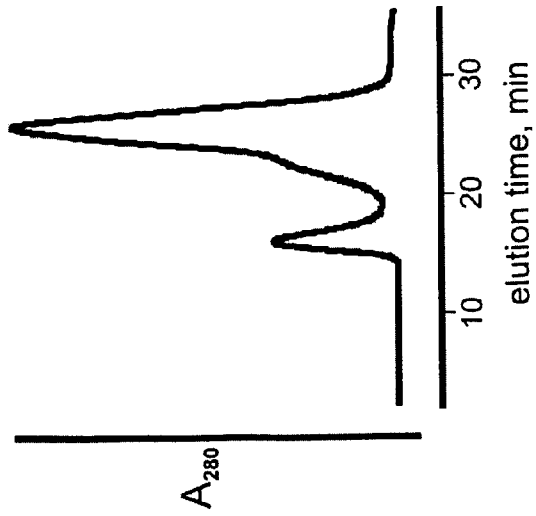
FIG. 5A shows the results of gel filtration (on a Superdex 200 sizing column) of a crude preparation of nanoscale disc-like particles containing rTF that were prepared using the detergent, deoxycholate. The x-axis is retention time on the column and the y-axis is A280. The nanoscale disc-like particles eluted from the column between 20 and 30 min.
Figure 5B:
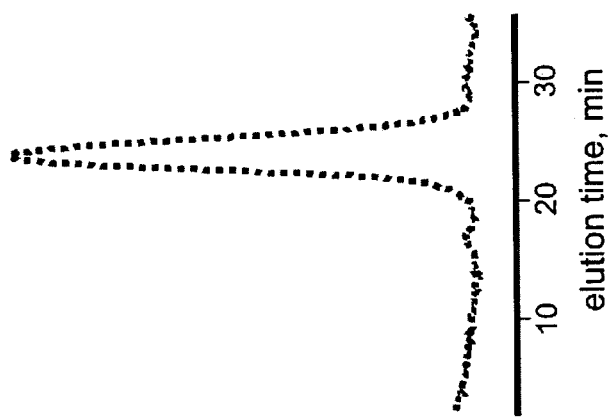
FIG. 5B shows the results of gel filtration (on a Superdex 200 sizing column) of the same preparation of nanoscale disc-like particles containing rTF shown in FIG. 5A, after they were enriched for TF-containing nanodiscs by immunoaffinity chromatography using immobilized HPC4 antibody. Note that the elution profile is more symmetrical and therefore the preparation appears to be more homogeneous than the crude nanoscale particle preparation exhibited in FIG. 5A.
Figure 5C:
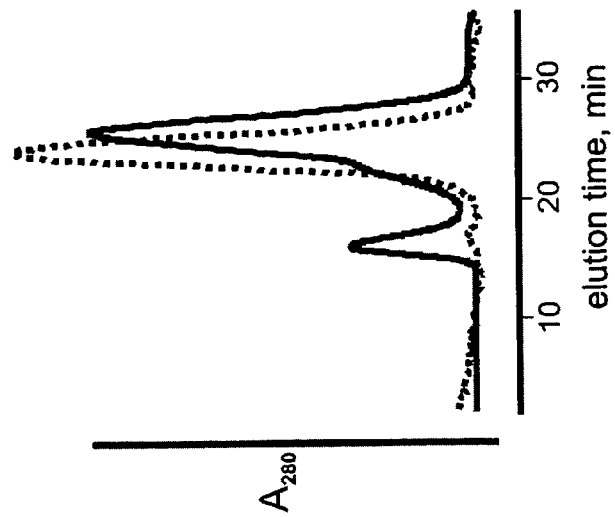
FIG. 5C shows the superimposition of the chromatograms from FIG. 5A and FIG. 5B.

When preparing TF-Nanodiscs, we typically use molar ratios of phospholipid:MSP1:membTF of 140:2:0.2. Using a tenfold molar excess of MSP over TF means that, on average, one TF molecule is incorporated for every five Nanodiscs. This ensures that, statistically, the majority of TF-Nanodiscs contain only one TF molecule, but only about 20% of the Nanodiscs contain TF. Pure populations of TF-Nanodiscs are isolated from the Nanodisc mixture as follows. First, the products of the Nanodisc self-assembly reactions are chromatographed by size-exclusion chromatography. A small peak consisting of aggregated material elutes first and is discarded, while Nanodiscs elute between 20 and 27 min on this column and are collected. The Nanodisc fraction, which contains a mixture of Nanodiscs with and without membTF, is then subjected to immunoaffinity chromatography using immobilized HPC4 monoclonal antibody. A small epitope tag incorporated at the N-terminus of membTF facilitates purification from the E. coli expression system (Rezaie et al. 1992. Prot. Expr. Purif. 3:453-460). The HPC4 antibody binds to this peptide epitope with very high affinity in a $Ca^{2+}$-dependent manner, which allows for gentle elution of the tagged protein using EDTA. The presence of this epitope tag on the N-terminus of TF has no effect on its activity. The HPC4 epitope tag enables isolation of a pure population of TF-Nanodiscs. When re-chromatographed on size-exclusion chromatography, TF-Nanodiscs elute in a much more symmetrical peak whose Stokes diameter is slightly larger than that of Nanodiscs not containing TF (FIG. 5B).

The TF and MSP content of the purified TF-Nanodisc preparation was analyzed by SDS-PAGE followed by Coomassie staining. Densitometry scanning of the lane (calibrated against known quantities of TF and MSP loaded on the same gel) revealed a 0.51 molar ratio of TF:MSP protein. Since each Nanodisc contains two MSP molecules, this equates to 1.02 TF molecules per Nanodisc. We have also quantified the TF content of Nanodisc preparations using a TF ELISA (after detergent solubilization), and by titrating a fixed concentration of factor VIIa with increasing TF-Nanodisc concentrations, using the increase in factor VIIa amidolytic activity as the readout. These approaches all confirm an average of one TF molecule per Nanodisc.

Figure 6:
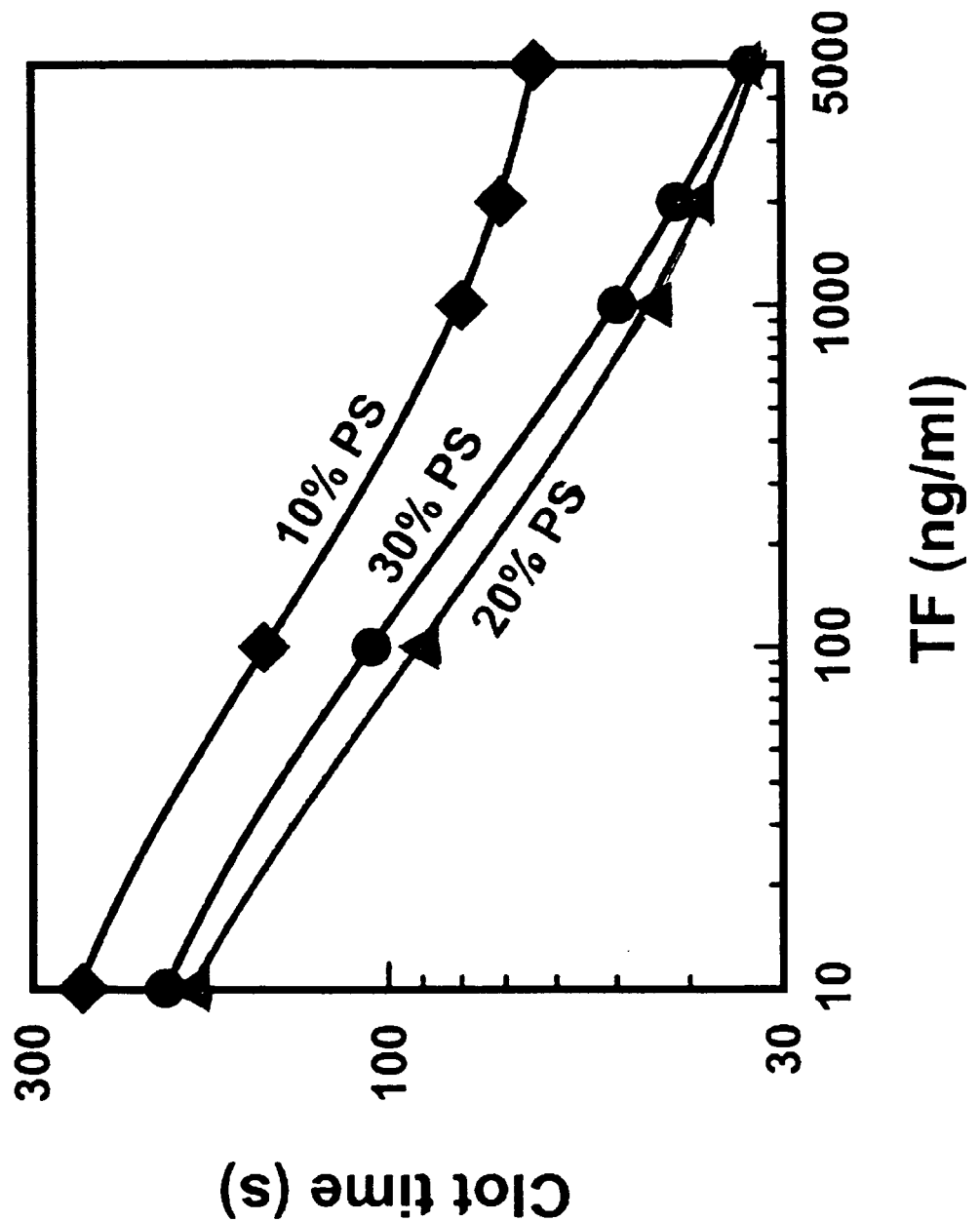
FIG. 6 shows the clotting activity of TF-Nanodiscs containing varying proportions of PS (remainder of phospholipid is PC). Clotting time is measured as a function time.
Figure 7:
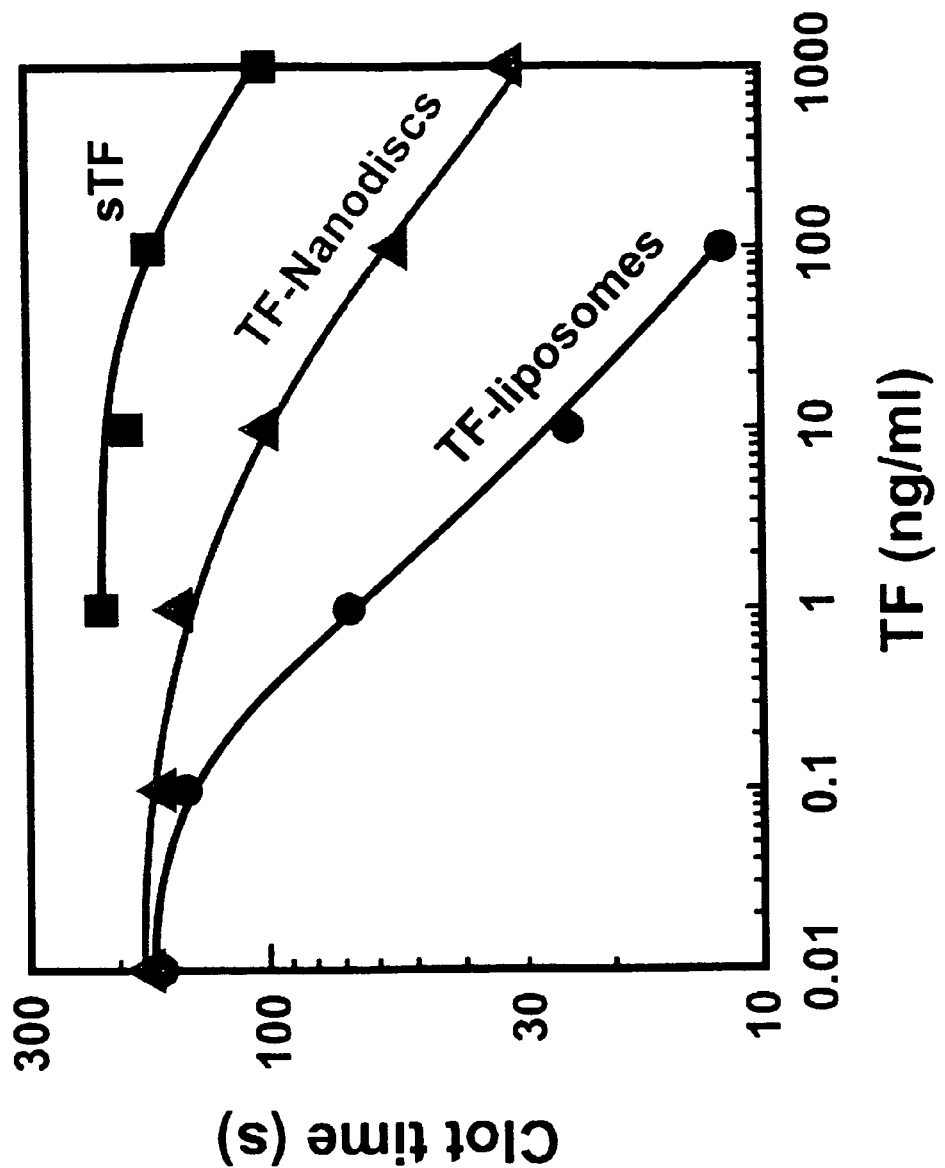
FIG. 7 provides a comparison of the clotting activities of TF-liposomes, TF-Nanodiscs and a mixture of sTF and PCPS vesicles.

It was demonstrated that we could make Nanodiscs with a phospholipid composition that was known, at least in liposomes, to optimally support blood clotting reactions and that we could incorporate a single molecule of TF per Nanodisc. TF-Nanodiscs function was evaluated in plasma clotting assays using three different preparations of TF-Nanodiscs in which the PS content was varied from 10 to 30 mol % (FIG. 6). The ability of TF-Nanodiscs to shorten the clotting time of plasma in a standard Prothrombin Time (PT) clotting test was tested as a function of TF concentration. This result demonstrated that TF-Nanodiscs do indeed possess procoagulant activity, and furthermore, that 20% PS was optimal. This finding parallels the known PS-dependence of TF procoagulant activity in liposomes (Neuenschwander et al. 1995. Biochemistry 34:13988-13993). We next compared the procoagulant activity of TF-Nanodiscs (containing 20% PS) to that of TF-liposomes (also containing 20% PS), and to a mixture of sTF and phospholipid vesicles containing 20% PS (FIG. 7). These results showed that TF-Nanodiscs exhibit appreciable procoagulant activity, although their specific activity is somewhat lower than that of TF-liposomes. Interestingly, the procoagulant activity of TF-Nanodiscs was at least 100-fold higher than that of sTF. Clotting of plasma in PT assays is dependent upon the sequential functioning of two membrane-bound protease-cofactor complexes: The first is the TF:VIIa complex, and the second is the prothrombinase complex (factor Va:factor Xa complex). The procoagulant activity of TF- Nanodiscs indicates that at least the first reaction (TF:VIIa activation of factor X) can occur on the Nanodisc surface.

A comparison of sodium cholate-solubilized phospholipids vs. sodium deoxycholate-solubilized phospholipids in discs was carried out. The detergent, sodium cholate, has typically been used previously in the preparation of nanoscale disc-like particles. However, recent studies have shown that sodium cholate is a relatively poor detergent for incorporating TF into phospholipid vesicles (Smith and Morrissey. 2004. J. Thromb. Haemost. 2: 1155-1162). Sodium deoxycholate, on the other hand, works very well for reconstituting TF into PCPS vesicles. We reasoned that sodium deoxycholate may also be preferable to cholate for incorporating rTF into PCPS-containing nanoscale discs. Our studies confirmed that more homogeneous preparations of PCPS-nanoscale discs were obtained using sodium deoxycholate than sodium cholate, as determined by size-exclusion chromatography. TF, MSP, deoxycholate and phospholipids (especially 80% PC, 20% PS) are incubated together at room temperature. Detergent is removed, for example using Biobeads, and the nanoscale disc-like particles self-assemble so that the TF is biologically active and associated with the particles. Size exclusion chromatography separates unincorporated molecules and aggregates from the nanoscale-disc-like particles. Those disc-like particles containing TF which has been engineered to contain an HPC4 epitope tag can be purifying by chromatography over an immunoaffinity column to which HPC4-specific antibody is bound.

While sodium deoxycholate has been used successfully in the preparation of the tissue factor-containing nanoscale particles, other detergents can be used as well. In addition to cholate and deoxycholate, other detergents can be used to assist in the incorporation of tissue factor into phospholipid bilayers, including t-octylphenoxypolyethoxyethanol (Triton X-100, Union Carbide Chemicals and Plastics Co., Inc.), n-octyl-beta-D-glucopyranoside (octylglucoside), octaethylene glycol monododecyl ether ($C_{12}E_8$), and nonaethylene glycol monododecyl ether ($C_{12}E_9$).

Once we had determined the optimal PL:MSP ratio for preparing PCPS-nanoscale discs and had found that sodium deoxycholate was preferable to sodium cholate, we incorporated rTF into PCPS-nanoscale discs. In this experiment, a molar ratio of 65:1:0.1 was used (PL:MSP:rTF) in the preparation mixture. This resulted in apparently homogeneous rTF-PCPS-nanoscale disc assemblies (as judged by size-exclusion chromatography). Further experiments identified an advantageous molar ratio of phospholipid:MSP:TF of 70:1:0.1. Useful range includes from 50:1:0.1 to 80:1:0.1. The proportion of rTF in the mixture from which the nanoscale particles is greater where more rTF molecules on average per particle is acceptable.

Tissue factor activity of rTF containing nanoscale disc-like particles, prepared as described herein, was then studied. The nanoscale discoid particles were fractionated using size-exclusion chromatography, and the various fractions were tested for TF procoagulant activity (the ability to shorten the clotting time of pooled normal human plasma). The shortest clotting times (highest TF activity) corresponded to the major absorption peak on the chromatogram. This indicates that active rTF was successfully incorporated into the nanoscale discs. By contrast, rTF that is not incorporated into a suitable phospholipid surface has negligible activity in this clotting test.

Because the starting ratio of MSP:rTF was 1:0.1 (i.e., a tenfold excess of MSP over rTF), and because there are two MSP molecules per nanoscale disc, it is estimated that even if one obtained 100% incorporation of rTF into discs, only about 20% of the discs would have rTF in them under these conditions. If the rate of rTF incorporation were less, then even fewer than 20% of the nanoscale discs would contain rTF. Therefore it is desirable to enrich for those nanoscale discs containing rTF. To do so, we took advantage of the HPC4 epitope tag on the N-terminus of rTF to purify the discs that contained rTF. The nanoscale disc preparation was made 5 mM in $CaCl_2$, and then the preparation was pumped over an HPC4 column, which column consists of the monoclonal antibody HPC4 attached covalently to AffiGel beads. HPC4 binds tightly, in a calcium-dependent manner, to the HPC4 epitope. HPC4 beads can be readily used to purify recombinant proteins containing this tag (Rezaie et al. 1992. vide infra). Purified HPC4 IgG is attached to a N-hydroxysuccinimide ester chromatography matrix (AffiGel, Bio-Rad Laboratories, Hercules, Calif.). HPC4 IgG and HPC4 attached to beads can also be purchased from Roche Applied Science. The nanoscale discs containing rTF bind to the HPC4 column, while "empty" nanoscale discs do not bind. After washing the column to remove any unbound particles, the rTF-containing particles were eluted with buffer containing 10 mM EDTA. Some material eluted from the HPC4 column in this initial experiment; it appeared to be severely aggregated material, as determined by size-exclusion chromatography. The published procedure for purifying rTF and sTF on HPC4 columns includes a step in which the column is washed in a "high-salt" (contains 1 M NaCl) buffer just prior to elution. Without wishing to be bound by theory, it is believed that the 1 M NaCl disrupted the nanoscale discs and promoted aggregation. The HPC4 purification procedure was repeated using a fresh preparation of nanoscale discs, and the HPC4 column was washed with a buffer containing 0.1 M NaCl instead of 1 M NaCl. This was successful and yielded a homogeneous preparation of nanoscale discs that eluted at the correct position when analyzed by size-exclusion chromatography (FIG. 5B).

An experiment was carried out to examine the optimum ratio of MSP:rTF when making rTF-PCPS-nanoscale disc-like particles. As the rTF content was increased, an increasingly large shoulder on the nanoparticle peak was observed when the preparations were subjected to size-exclusion chromatography. The shoulder region elutes before the main nanoscale disc peak, and is therefore apparently larger than nanoscale discs which did not contain TF. TF procoagulant activity eluted approximately with the main disc peak. Without wishing to be bound by any particular theory, it is believed that the shoulder includes aggregated material. A ratio of 1:0.1 MSP:rTF is used routinely, but higher proportions of rTF result in greater average incorporation of rTF per particle.

Some clotting tests were carried out with unoptimized nanoscale disc preparations. The experiments showed that even the unoptimized particles had readily measurable TF procoagulant activity.

More extensive studies with optimized rTF-PCPS-nanoscale disc-like particles were conducted, including measuring the $K_d$ for binding of factor VIIa to rTF within nanoscale discs. Factor VIIa binds to rTF in PCPS vesicles with a $K_d$<50 pM. On the other hand, it binds to sTF, or to rTF in pure PC vesicles, with a $K_d$ of about 2 to 5 nM. The explanation for the difference in binding affinity between rTF and sTF is that the protein-protein interactions between factor VIIa and TF are sufficient to provide a $K_d$ of 2 to 5 nM. When factor VIIa binds to rTF in PCPS vesicles, however, there are both protein-protein interactions (between factor VIIa and TF) and protein-phospholipid interactions (between the Gla domain of factor VIIa and negatively-charged phospholipids). The protein-phospholipid interactions are thought to provide additional binding energy, giving rise to the tighter $K_d$. We have observed that factor VIIa binds to rTF-PCPS-nanoscale discs with a $K_d$ that is also in the pM range, and is only slightly higher than that observed for binding of factor VIIa to rTF in PCPS vesicles. This indicates that rTF-PCPS-nanoscale discs provide an environment for binding factor VIIa that is very similar to rTF incorporated into phospholipid vesicles.

The purpose of this study was to compare the binding and enzyme kinetic properties of recombinant human tissue factor (rTF) incorporated into PCPS-nanoscale discs to rTF incorporated into PCPS vesicles. The rTF used in these studies is recombinant human tissue factor produced in bacteria. rTF was incorporated into PCPS-nanoscale discs as described, and then further purified on an HPC4 column to isolate nanoscale disc-like particles that contain rTF. For comparison purposes, rTF was also incorporated into PCPS vesicles using a Bio-Bead method (Smith and Morrissey. 2004. supra). The compositions of the two preparations are given as follows:

rTF-PCPS-nanoscale discs:
  20 mol % phosphatidylserine (PS)
  80 mol % phosphatidylcholine (PC)
  molar ratio of PL:MSP was 65:1
rTF in PCPS vesicles:
  20 mol % PS
  80 mol % PC
  molar ratio of PL:rTF was 8700:1

We determined the apparent $K_d$ for binding of factor VIIa to rTF in both settings using the TF-dependent enhancement of factor VIIa enzymatic activity as the readout for complex formation. We also determined apparent $K_m$ and $k_{cat}$ values for factor X activation by the rTF:VIIa complex using either 500 pM factor VIIa and 5 pM rTF. Factor X concentrations varied from 0 to 800 nM. Table 2 lists the $K_d$, $K_m$, and $k_{cat}$ values obtained.

TABLE 1

Kinetic parameters for Factor X Activation

|  | $K_{d, app}$ (pM) | Km, app (nM) | kcat$^{-1}$ (s) |
|---|---|---|---|
| rTF in PCPS vesicles | 26.4 ± 2.8 | 20.2 ± 1.0 | 2.4 ± 0.4 |
| rTF-PCPS-nanoscale discs | 65.1 ± 3.7 | 68.6 ± 4.3 | 1.5 ± 0.3 |

As can be seen from this data, factor VIIa bound to rTF very tightly when rTF was incorporated into either nanoscale discs or phospholipid vesicles. Both $K_d$ values were in the low pM range, in agreement with literature values (Neuenschwander and Morrissey. 1994. J. Biol. Chem. 269: 8007-8013). The binding of factor VIIa to rTF was slightly stronger when rTF was in phospholipid vesicles compared to nanoscale discs, but in both cases the binding was sufficiently tight to ensure complete binding of factor VII to rTF at plasma concentrations of factor VII, which is approximately 10 nM (Fair. 1983. Blood 62: 784-791).

We have also measured $k_{cat}$ and $K_m$ values for the activation of factor X by factor VIIa bound to rTF-PCPS-nanoscale discs; kinetic constants for this reaction are very similar to those of factor VIIa bound to rTF in PCPS vesicles. This is another important test of the ability of factor VIIa bound to rTF within nanoscale discs to function as the activating enzyme of the blood clotting system. A priori, it was unclear whether or not rTF-PCPS-nanoscale discs would be comparable to rTF in PCPS vesicles in supporting factor VIIa proteolytic activity. The lipid bilayer encompassed by the nanoscale discs is relatively small, with only approximately 65 phospholipid molecules per side. This relatively tiny lipid bilayer has to bind both the enzyme (factor VIIa) and the substrate (factor X) onto the same side of the nanoscale disc-like particle in order for catalysis to occur efficiently.

The $K_m$ and $k_{cat}$ values obtained for factor VIIa bound to rTF in PCPS vesicles (given in the table above) are comparable to literature values (Fiore et al. 1994. supra). Note that the $K_m$ values for factor X activation by rTF:VIIa are given as apparent $K_m$ values because this number depends strongly on the phospholipid concentration used in the assay. The $K_m$ and $k_{cat}$ values obtained for the two forms of rTF:VIIa complexes were similar. Both forms of the enzyme exhibited $K_m$ values that are below the factor X concentration in plasma, indicating that they are both efficient in recognizing factor X as a substrate in plasma. The $k_{cat}$ value obtained with factor VIIa bound to rTF-PCPS-nanoscale disc-like particles was approximately 1.6-fold lower than the value obtained for factor VIIa bound to PCPS vesicles. This indicates that the rTF:VIIa complex on nanoscale discs is only slightly less active than rTF:VIIa complexes in phospholipid vesicles in converting factor X to Xa. This may be a consequence of the much smaller membrane surface available for binding factor X or Xa in a nanoscale disc of about 10 nm to about 14 nm in diameter, compared to a phospholipid vesicle of some 300 nm diameter.

We have shown TF can be incorporated into Nanodiscs with high yield, and that TF-Nanodiscs can be purified from mixtures containing Nanodiscs lacking TF using immunoaffinity chromatography, providing a highly homogeneous population, containing on average one TF molecule per disc. We also showed that TF-Nanodiscs exhibit significant procoagulant activity, orders of magnitude more active in clotting assays than is the combination of sTF and PCPS vesicles. TF incorporated into Nanodiscs containing PS is highly functional, and the TF-Nanodisc system is capable of supporting membrane-dependent blood clotting reactions.

A priori, it had been uncertain whether or not TF could efficiently initiate clotting when embedded in such small membrane bilayers (approximately 65 phospholipid molecules per side) because TF, as an integral membrane protein, occupies some of the membrane surface, and factor VIIa occupies a bit more, owing to interactions between its Gla domain and phospholipids. We previously quantified the ability of interactions between the factor VIIa Gla domain and PS to stabilize the TF:VIIa complex (Neuenschwander and Morrissey 1994. J. Biol. Chem. 269:8007-8013). TF incorporated into pure PC vesicles binds factor VIIa with a $K_d$ in the nM range, while TF-liposomes containing 20% PS bind factor VIIa with a $K_d$ in the low pM range. Therefore, we expect that some of the PS molecules in TF-Nanodiscs are bound to factor VIIa's Gla domain when the TF:VIIa complex forms on these discs.

In order for TF:VIIa complexes on TF-Nanodiscs to exhibit significant procoagulant activity, the remaining phospholipid surface must have sufficient room, and sufficient free PS, to reversibly bind protein substrates, which in the case of the clotting assay is factor X. Like factor VIIa, factor X also interacts with negatively charged phospholipids including PS via its Gla domain, and these interactions are important for efficient recognition as a substrate by TF:VIIa. With conventional TF-liposomes, the apparent $K_m$ for factor X activation by the TF:VIIa complex is in the pM range in the absence of PS, but this falls to the nM range (generally, 20 to 100 nM depending upon the experimental conditions) in the presence of PS. Binding of factor X's Gla domain to PS molecules in the immediate vicinity of TF:VIIa therefore contributes to stabilizing the enzyme-substrate complex, lowering the apparent $K_m$. The TF-Nanodisc system provides a system for analyzing highly localized protein-phospholipid interactions within the immediate vicinity of the membrane-bound enzyme and the binding characteristics of the enzyme, factor VIIa, to TF-Nanodiscs, and also the binding of substrates (factors IX and X) to both Nanodiscs and TF-Nanodiscs.

Two methods are used for quantifying the binding affinity of factor VIIa to TF-Nanodiscs. In the first method, we use the large increase in factor VIIa enzymatic activity as the readout for complex formation (see Neuenschwander and Morrissey. 1994. supra). In the second method, surface plasmon resonance (SPR) in a Biacore 3000 instrument is used to quantify association of factor VIIa with TF-Nanodiscs. We have used the first method (change in enzyme activity) to quantify binding of factor VIIa to TF-Nanodiscs in which the supported phospholipid bilayer contained 10, 20 or 30% PS (with the balance being PC). This was compared to binding of factor VIIa to TF in liposomes containing 20% PS using the same method. Table 2 shows that factor VIIa bound to TF-liposomes with a 26.4 pM $K_d$, which is in agreement with published values (Neuenschwander and Morrissey. 1994. supra). Factor VIIa bound to TF in Nanodiscs with similarly tight $K_d$ values (in the low pM range) when the TF-Nanodiscs contained 10, 20 or 30% PS. TF in Nanodiscs containing mixtures of PS and PC binds factor VIIa with similarly high affinity with which TF in conventional liposomes binds factor VIIa.

TABLE 2

Binding constants for TF:VIIa complexes

|  | Phospholipid | Factor VIIa binding $K_d$ (pM) |
|---|---|---|
| TF-liposomes | 20% PS, 80% PC | 26.4 ± 2.8 |
| TF-Nanodiscs | 10% PS, 90% PC | 83.7 ± 6.0 |
|  | 20% PS, 80% PC | 65.1 ± 3.7 |
|  | 30% PS, 70% PC | 57.4 ± 1.3 |
| sTF |  | about 3000 |

The TF-dependent enhancement of factor VIIa enzymatic activity is used to quantify the binding affinity of factor VIIa to TF on Nanodiscs of variable phospholipid composition and variable Nanodisc size.

SPR (Biacore) approaches are used to quantify the equilibrium binding affinities as well as association and dissociation rate constants for the binding of clotting factors to Nanodiscs of varying size and composition. Nanodiscs of a desired composition are bound to a sensorchip and then the protein of interest is allowed to flow over the Nanodisc-chip to quantify binding. While other types of immobilized phospholipid membrane surfaces can be prepared on sensorchips, immobilizing Nanodiscs has the advantage that the binding rates of various membrane-binding proteins are measured as they associate with the identical membrane surface that are used in functional studies, in solution, of the catalytic activities of membrane-bound protease complexes.

Nanodiscs can be attached to the sensorchip surface using a variety of approaches, owing to the adaptability built into the recombinant MSPs that encircle them. One approach used successfully is to simply flow Nanodiscs over an NTA chip. The MSP encircling the Nanodiscs have an oligohistidine tag engineered therein for ease of purification, and this same oligohistidine tag can be exploited to immobilize the Nanodiscs onto a Nickel-Nitriloacetic acid (NTA) chip. Nickel chelated by nitrilotriacetic acid (NTA) is pre-immobilized on a carboxymethylated dextran matrix of the sensor chip. The sensor chip can be regenerated with the use of the metal chelating compound (ethylenedinitrilo)tetraacetic acid (EDTA).

To form a more specific linkage to sensor chips, as well as one that could be used in the presence of other divalent cations, such as calcium, which can disrupt the histidine tag binding to nickel, a second method was developed. This attachment involves covalently labeling the MSP with a single-stranded DNA; a biotinylated complementary strand of DNA is bound to a sensor chip with pre-immobilized streptavidin and used to capture the DNA-tagged Nanodiscs. The heterobifunctional linker sulfosuccinimidyl 4-N-maleimidomethyl cyclohexane-1-carboxylate (Sulfo-SMCC) has been used to bind amine-labeled DNA to the thiol group of a cysteine mutant engineered into MSPs. The same DNA has also been attached to carboxyl groups present on MSPs using (1-Ethyl-3-[3-dimethylaminopropyl]carbodiimide hydrochloride) (EDC). Both methods of DNA attachment show specific binding to the complementary strand immobilized on Biacore chips, and the chips are regenerated using a high salt solution containing sodium hydroxide which separates the strands of DNA. The use of these DNA-tagged Nanodiscs has been extended to patterning the discs on DNA chips where highly-fluorescent Nanodiscs have been arrayed and imaged upon binding to microarrayed spots of complementary DNA. When Nanodiscs with oligonucleotide-tagged MSPs are flowed over the sensorchip containing the immobilized complementary oligonucleotide, the discs become immobilized via hybridization between the complementary oligonucleotide sequences. Both approaches work well, and each approach has its own advantages.

Figure 8:
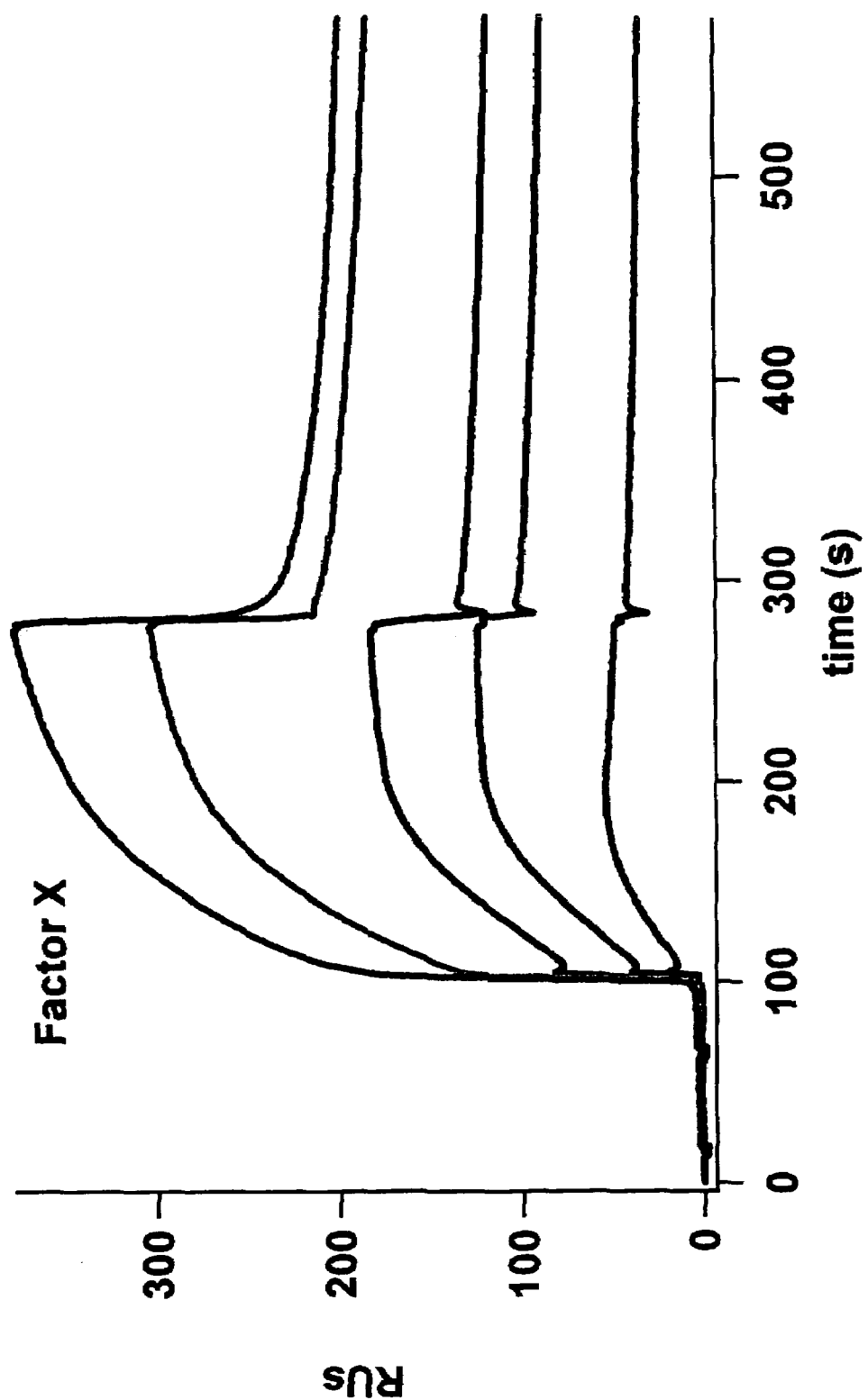
FIG. 8 shows the results of SPR (Biacore 3000) analysis of factor X binding to Nanodiscs of varying phospholipid content. Nanodiscs (no TF) were prepared using mixtures of the indicated percent POPS, with the balance being POPC. The Nanodiscs were then immobilized on NTA chips via the oligohistidine tag present as part of MSP1. Factor X was flowed over the immobilized discs starting at 100 seconds (association phase) followed by buffer only at 280 seconds (dissociation phase) Nanodiscs containing 100% POPC employed as a control showed no evidence of factor X binding; they only exhibited the RU shift due to the refractive index of the factor X solution (not shown). Sensorgrams for POPC Nanodiscs run in parallel were therefore subtracted from the sensorgrams presented herein. Traces from top to bottom are 25%, 20%, 15%, 10% and 5% POPS.
Figure 9:
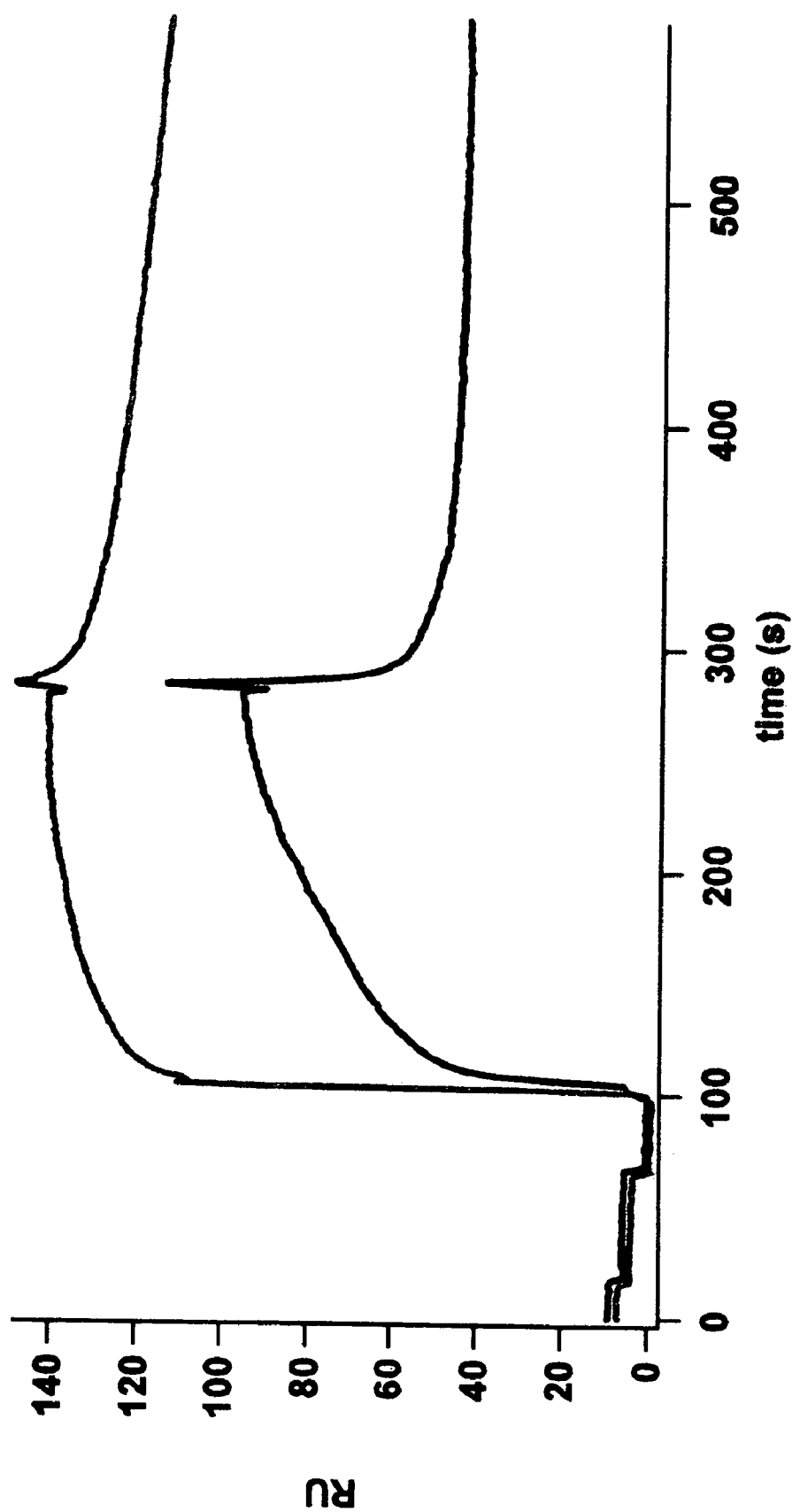
FIG. 9 demonstrates that factor VIIa binding to TF-Nanodiscs is faster than to Nanodiscs containing only MSP and phospholipids, as measured by SPR. The upper trace is that of the TF-Nanodiscs and the lower is that for containing only MSP and phospholipids.

An example of immobilizing Nanodiscs on an NTA sensorchip surface is given in FIG. 8. Nanodiscs lacking TF but containing 5 to 25% POPS (with the balance being POPC) were immobilized on NTA Biacore chips and analyzed using a Biacore 3000 instrument. Nanodiscs were loaded onto the chips at a concentration of 50 nM MSP using a flow rate of 5 µL/min. Nanodisc loading was monitored by the Biacore sensorgram and was stopped when 500 RU of discs were loaded for each sample. We chose to examine factor X binding to these immobilized Nanodiscs. Factor X was injected at a concentration of 1 µM using a flow rate of 10 µL/min. All portions of the experiment were performed using a buffer solution containing 10 mM HEPES pH 7.4, 150 mM NaCl, 2.5 mM $CaCl_2$. Immobilized Nanodiscs containing only POPC were run simultaneously as a control and were subtracted from each sample yielding the binding curves shown in FIG. 8.

FIG. 8 demonstrates that we can successfully use Biacore analysis to study binding of vitamin K-dependent clotting factor (factor X) to immobilized Nanodiscs. As can be seen from the experiment in FIG. 8, factor X binding to the immobilized Nanodiscs depended strongly on the PS content of the supported bilayers, with both the rate and extent of binding being highest at the highest PS contents. Furthermore, dissociation rates were slowest in Nanodiscs containing the highest % PS. This system can be used to quantify the binding of factors VIIa, IX and X to immobilized Nanodiscs containing varying phospholipid compositions. Data obtained from such studies are used to characterize the Nanodisc system and to provide a baseline from which to calculate affinities of both enzyme and substrate to the same membrane microenvironment enclosed within Nanodiscs, with care taken to ensure that apparent binding and dissociation rate constants are not complicated by artifacts arising from mass transport limitations and rebinding effects, for example, by limiting the quantity of Nanodiscs attached to the membrane surface and examining the effects of altering the flow rate and concentration of the ligand that is being flowed over the sensorchip. It is understood that other strategies can be employed to immobilize the nanoscale particles comprising TF, for example by anchoring via the cytoplasmic tail or truncated cytoplasmic tail of the TF, or via at least one phospholipid molecule.

We have shown that TF-Nanodiscs have substantial procoagulant activity, although their specific activities in clotting assays were somewhat lower than TF-liposomes when compared at the same TF concentrations (FIG. 7). The lower specific activity in clotting assays could be due to lower catalytic efficiency of TF:VIIa complexes on Nanodiscs compared to TF-liposomes, or it could be due to lower ability to support the prothrombinase complex, since both reactions are required in a typical PT clotting assay. We therefore examined, in preliminary experiments, how well the TF:VIIa complex activated factor X on Nanodiscs compared to TF-liposomes with the same phospholipid composition. We already showed that TF-Nanodiscs bound factor VIIa with affinities that were comparable to TF-liposomes (Table 3), so we know that assembly of the TF:VIIa complex is not impaired on Nanodiscs. We therefore addressed the catalytic competence of the TF:VIIa complex toward activation of factor X. Initial rates of factor X activation were quantified using TF:VIIa complexes assembled on liposomes and Nanodiscs as a function of increasing factor X concentration. Initial estimates of the rate constants for factor X activation are given in Table 3.

TABLE 3

Kinetic constants for TF:VIIa complexes

|  | Phospholipid | Factor X activation | |
|---|---|---|---|
|  |  | $K_m$ (nM) | $k_{cat}$ (s$^{-1}$) |
| TF-liposomes | 20% PS, 80% PC | 20.2 + 1 | 2.4 ± 0.24 |
| TF-Nanodiscs | 10% PS, 90% PC | 131.8 + 12.1 | 1.4 ± 0.2 |
|  | 20% PS, 80% PC | 68.6 ± 4.3 | 1.5 ± 0.3 |
|  | 30% PS, 70% PC | 45.2 ± 2.4 | 1.4 ± 0.3 |

Remarkably, TF:VIIa complexes assembled on Nanodiscs exhibited kcat values that differed from by less than a factor of two from those of TF:VIIa complexes assembled on liposomes of the same phospholipid composition. TF:VIIa complexes assembled on liposomes exhibited lower apparent Km values than did TF:VIIa complexes assembled on Nanodiscs. There was a trend toward lower Km values as the PS content of the Nanodiscs increased. The higher apparent Km values of TF-Nanodiscs compared with TF-liposomes may explain, at least in part, the somewhat lower specific procoagulant activity of TF-Nanodiscs compared with TF-liposomes in PT clotting assays. In a typical PT assay, the plasma is diluted three-fold in the final clotting reaction. The plasma concentration of factor X is approximately 170 nM, so diluting the plasma in the PT clotting assay reduces its concentration to about 57 nM. This tends to exaggerate the difference in apparent specific activity between TF-liposomes and TF-Nanodiscs; therefore these clotting assays are desirably supplemented with sufficient factor X to keep its final concentration at 170 nM, as a more direct estimation of specific activities that these various TF complexes exhibit in undiluted plasma.

In summary, rTF in nanoscale discs exhibits properties that are surprisingly similar to rTF in large unilamellar vesicles. Factor VIIa bound very tightly to rTF in nanoscale discs, and the rTF:VIIa complex on these discs exhibited enzyme kinetic properties that are surprisingly similar to rTF:VIIa complexes on the surface of phospholipid vesicles. These studies demonstrate the feasibility of using rTF-PCPS-nanoscale discs as nanoreactors for the activation of plasma factor X to factor Xa, thereby triggering the blood coagulation cascade.

TF (especially as rTF) formulated within nanoscale disc-like particles as described herein can be administered for killing tumors. Previous studies by others have shown that truncated recombinant TF (sTF) can be attached to a bispecific targeting antibody for delivery of sTF to the vascular bed of tumors in experimental animals, resulting in killing of the tumor (Huang et al. 1997. Science 275: 547-550). This general targeting strategy appears to work by concentrating sTF at the surface of the tumor vasculature, whereupon sTF triggers the blood clotting cascade locally, forming a thrombus that infarcts the tumor vascular bed and kills the tumor. Delivery of sTF to tumor vascular beds as a means of tumor killing has been successfully employed in a number of other model studies, which have used different targeting molecules for addressing the sTF payload to the tumor vasculature. This includes coupling sTF to antibodies to vascular cell adhesion molecule-1 (VCAM-1) (Ran et al. 1998. Cancer Res. 58: 4646-4653); coupling sTF to antibodies to the receptor for vascular endothelial growth factor (VEGFR1) (Brekken and Thorpe 2001. Anticancer Res. 21: 4221-4229); coupling sTF to single-chain antibody fragments to fibroblast activation protein (FAP) (Rippmann et al. 2000. Biochem. J. 349: 805-812); creating a fusion protein between sTF and portions of fibronectin (Nilsson et al. 2001. Cancer Res. 61: 711-716; Liu et al. 2004. Mol. Cancer. Ther.); and coupling sTF to a catalytic site inhibitor of prostate-specific antigen (PSMA) (Liu et al. 2002. Cancer Res. 62: 5470-5475).

TF formulated within nanoscale disc-like particles can be targeted to the tumor vasculature using the same targeting strategies and targeting molecules as have been used to target sTF. This can be accomplished by linking the targeting antibody (or other suitable targeting molecule) directly to rTF within the nanoscale disc-like particles, or it can be accomplished by linking the targeting antibody (or other suitable targeting molecule) directly to the matrix scaffold protein within the nanoscale disc-like particles. Alternatively, targeting can be accomplished by linking the targeting antibody (or other suitable targeting molecule) to the supported phospholipid bilayers within the nanoscale disc-like particles. TF formulated within nanoscale disc-like particles has much higher procoagulant activities than sTF and therefore has superior efficacy in triggering the blood clotting cascade locally once targeted. In addition to the targeting strategies discussed above for targeting sTF to vascular beds, other targeting strategies, both general and specific, have been discussed in the scientific literature which can be utilized for targeting rTF within nanoscale disc-like particles to tumor vasculature, including bispecific antibodies, conjugates with monoclonal antibodies, recombinant single-chain antibodies, and other targeting molecules (Cao and Lam 2003. Adv. Drug Del. Rev. 55: 171-197; Trail et al. 2003. Cancer Immunol. Immunother. 52: 328-337; Carter 2001. Nat. Rev. Cancer 1: 118-129; Gottstein et al. 2001. Biotechniques 30: 190-194; Ruoslahti 2002 Drug Discov. Today 7: 1138-1143; and Konig et al. 2002. Endothelium 9:161-171; Ran et al. 1998. Cancer Res. 58:4646-4653).

The TF-containing particles can be administered locally to the tumor, for example, incorporated within slowly dissolved materials, or they can be administered intravenously and targeted to the tumor by incorporating targeting molecules, such as antibodies, single chain tumor-binding antibodies or tumor-binding fragments of antibodies, within the nanoscale particles so that the tumor-binding portion is external to the disc and free to bind to the target tissue. Desirably, the dose of TF administered should be about 0.5 mg TF incorporated in particles per kg body weight to about 5 mg TF incorporated in particles per kg body weight. It is preferred that a targeting molecule be included within the particle either within the MSP or TF derivative so that clotting activity is not systemic or excessive so as to cause harm to the patient to whom the particles have been administered.

Clinical situations in which excessive bleeding is encountered include surgery or trauma in patients with hereditary or acquired deficiencies in the blood clotting system. Patients with such deficiencies include patients with thrombocytopenia and hemophilia (patients lacking factor VIII or IX), especially patients who have developed inhibitory antibodies against therapeutically administered factor VII or IX. Current therapies for such refractory patients include injection of coagulation factor concentrates or recombinant factor VIIa, which are generally very expensive (Carr and Martin, 2004. Expert Rev. Cardiovasc. Ther. 2: 661-674). Additionally, bleeding (especially surgical bleeding) is sometimes treated using topical hemostatic agents such as collagen sponges, oxidized cellulose, chitosan derivatives, and "fibrin glue" (which contains a mixture of thrombin, fibrinogen and factor XIII). Topical agents containing materials like collagen, cellulose or chitosan are designed to activate blood platelets and stimulate vasoconstriction, both of which can facilitate hemostasis. Additionally, these agents may be used in conjunction with thrombin or "fibrin glue" to stimulate the formation of cross-linked fibrin in order to enhance the formation of hemostatic plugs, thereby helping to control bleeding (Pusateri et al. 2003. J. Trauma 55: 518-526; Soffer et al. 2003. Oral Surg. Oral Med. Oral Pathol. Oral Radiol. Endod. 95: 521-528). TF in a suitable phospholipid membrane is the most potent known initiator of blood clotting and, because of its extremely potent procoagulant activity, would be advantageous to incorporate into topical hemostatic agents in place of thrombin. However, phospholipid vesicles containing TF are relatively unstable and are difficult to immobilize onto solid surfaces. Nanoscale, disc-like particles comprising a membrane scaffold protein, on the other hand, are known to be stable after lyophilization and they can be attached to solid supports via crosslinking between the membrane scaffold protein and sites on the solid support matrices. It would therefore be highly desirable to immobilize nanoscale particles comprising TF in or on topical hemostatic agents in order to stop bleeding.

The present invention provides nanoscale particles comprising TF, which can be applied topically, either alone or administered bound to a solid support, desirably a macroscopic support material, such as a collagen sponge, microcrystalline collagen, chitosan derivatives, cellulose or latex beads, in applications of nanoscale disc-like particles containing TF (or rTF) as described herein for controlling bleeding. An example of a cellulosic material useful in the present context is a gauze used in bandages or wound dressings. An example of topical application of nanoscale particles comprising TF alone is a mouthwash containing a suspension of such particles, which can be used to control bleeding in the oral cavity following dental surgery. In other examples, nanoscale particles comprising TF in which the nanoscale particles are bound to solid support matrices can be applied to surgical sites and sites of trauma in order to activate the blood clotting cascade locally. In these settings, immobilization of nanoscale particles comprising TF has the additional advantage that the TF particle is not washed out of the wound site by hemorrhaging blood, and furthermore, that the TF particle is not readily released back into the circulation of the patient. Similarly, such bound TF can be advantageously administered to a patient who does not suffer from a hemophilia but who is experiencing bleeding due to trauma or surgery or any other reason. The target incorporated into the nanoscale disc-like particles can be attached to the surface of a solid support, including collagen sponges or other macroscopic pieces, microcrystalline collagen, or latex beads, in a variety of ways. The first is the easiest and nonspecific way, which is to rely on physisorption to the surface of the material using either hydrophobic or electrostatic forces. More stable incorporation or attachment can be via covalent bonding. This can be accomplished through chemical cross-linking between the scaffold protein and the solid support. There are a number of chemical cross-linking reagents that can be used to form covalent crosslinks between the scaffold protein and the support matrix, including homobifunctional amine reagents such as glutaraldehyde, bis(imido esters), and bis(succinimidyl esters), and heterobifunctional reagents such as 1-ethyl-3-[3-dimethylaminopropyl]carbodiimide hydrochloride. The nanoscale disc-like particles can also be immobilized through incorporation of derivatized phospholipids or fatty acyl chains, or including biotinylated phospholipids, which can then be attached to the support matrix via interaction with immobilized avidin or streptavidin. The TF is bound to a collagen sponge or similar solid support at a density of from about 1 ng to about 100 μg rTF (incorporated in nanoscale particles) per gram (dry weight) of solid support matrix. The use of a cysteine-containing MSP allows the use of a heterofunctional cross linker where one reactive group reacts with a free sulfhydryl to effect bonding the TF particle to the solid material (such as a collagen sponge). Descriptions of immobilization reactions using bifunctional cross linking molecules are given herein.

Alternatively, the particles containing the TF can be injected intravenously and targeted to adhesion molecules that are exposed on activated platelets or to other molecules such as collagen or tissue adhesive proteins that are not normally exposed to blood in intact blood vessels but are exposed to blood at sites of wounds. This can be achieved by binding or crosslinking a targeting antibody or other targeting agent to the MSP with nanoscale particles containing TF, although care must be taken to avoid excessive or uncontrolled clotting factor activation in circulation.

In addition to hemophiliac patients, other patients subject to excessive bleeding can also benefit from the administration, especially local administration, of nanoscale particles containing TF. Victims of accidents or other traumatic injuries or surgical patients, including but not limited to liver surgery patients, can be treated with the particles of the present invention. Other types of patients who can be treated by administration of nanoscale particles containing TF to control bleeding include patients with acquired or congenital coagulopathies including patients with thrombocytopenia, sepsis, liver failure, disseminated intravascular coagulation, and other coagulopathies.

The target incorporated into nanoscale disc-like particles can be attached to a surface, either a sponge or latex bead, in one of three ways. The first, easiest but also non-specific, is to rely on physisorbtion to the material using either hydrophobic or electrostatic forces. More stable incorporation is via covalent linkages. This can be accomplished through crosslinking with the scaffold protein or through incorporation of labeled phospholipids or fatty acyl chains.

An additional application of the TF-containing nanoscale disc-like particles of the present invention is as a reagent in Prothrombin Time (PT) assays which are employed to screen for defects in the blood clotting system and to monitor patients who are being treated with anticoagulants. This assay uses a source of TF activity (a thromboplastin reagent) to trigger clotting of blood or plasma in vitro, and the time interval between adding the TF reagent and the formation of the blood or plasma clot is the PT value. Previously, the thromboplastin reagent was simply an extract of homogenized tissue, most commonly animal or human brain or human placenta. More recently recombinant thromboplastins have been developed based on purified recombinant human or rabbit TF that has been reconstituted into suitable phospholipid vesicles. TF-containing nanoscale discs-like particles can be used as the thromboplastin reagent in PT assays. They have the advantages of stability to aggregation in aqueous environments as well as excellent stability of the procoagulant activity of TF in these particles.

TF can be embedded into the phospholipid portion of membrane scaffold protein-supported nanoscale disc-like particles by virtue of the interaction of the membrane-spanning domain of TF with the phospholipid of the particles. The nanoscale particles provide the necessary phospholipid surface to support the TF:VIIa enzymatic activity. Clearly, TF in the nanoscale discs can bind and allosterically activate factor VIIa, because the resultant discs exhibit strong procoagulant activity. It is also clear from the clotting studies that the TF:VIIa complex in the nanoscale particles can proteolytically activate its natural substrate, factor X. The TF in the nanoscale particles provides a unique way to deliver and control TF activity. The procoagulant activity of TF can, for example, be controlled by modulating the content of negatively charged phospholipids in the nanoscale disc-like particles.

To study the half-life in circulation, fluorescein-labeled nanoscale discs, which served as a model for rTF-containing discs, were prepared using MSP1 and phospholipid (PSPC 80:1) and injected intravenously into a rat. Based on measurement of the absorbance at 280 nm, 20.6 µM particles (about 255 µg particles) were injected in a 0.5 ml bolus. The estimate based on absorbance at 497 nm was 16.7 µM particles, with an assumption of 2 molecules fluorescein conjugated per particle. The rats used were about 200 g, with an estimated blood volume of about 13 ml. 0.2 ml aliquots of blood were taken at time intervals after injection. The blood was collected into dry heparin, with a final concentration of heparin of 333 U/ml. The heparinized blood was centrifuged to remove cells, and the emission of fluorescein was measured at 520 nm. The estimated half-life of the particles in circulation was about 5.5 hours. The equation describing the persistence in circulation is $y=-0.055x+1.64$; $R2=0.9663$.

Recombinant tissue factor consists of an extracellular domain, a transmembrane anchor and a truncated cytosolic domain. The truncation increases the homogeneity of the protein by removing the C-terminal portions of the protein which are subject to proteolysis by bacterial enzymes, but this modification does not affect TF activity. Additional modifications to the protein include an N-terminal trafficking peptide and an HPC4 epitope tag. The trafficking peptide directs the expressed protein to the intermembrane space of the recombinant *E. coli* host cell, in which space the peptide sequence is cleaved. The HPC4 epitope allows for affinity purification with $Ca^{2+}$ dependent antibody (Rezaie et al., 1992) and does not affect TF activity.

rTF-containing nanoscale disc-like particles can be prepared using cholate and dialysis as follows. A 25 mM lipid mixture containing 80% phosphatidylcholine and 20% phosphatidylserine was solubilized with 50 mM sodium cholate in 10 mM Tris Cl, 150 mM NaCl at pH 8.0. TF, MSP1 and phospholipid (in a ratio of 1:10:1000) were combined and incubated overnight at 37° C. The sample was then dialyzed at 37° C. (10,000 dalton molecular weight cutoff membrane) against buffer containing 10 mM Tris Cl, 150 mM NaCl at pH 8.0 (lacking sodium cholate) for 2 hours. Dialysis was then continued at 400 for an additional 6 hours with buffer changes every 2 hours. The approximately 1 ml sample was then concentrated to <250 µl using a YM-10 centrifuge concentrator and injected into a Pharmacia 10/30 Superdex 200 HR gel filtration column. Samples were eluted with buffer identical to that described above (no sodium cholate) at 0.5 ml per minute. Fractions from chromatography were run on an 8-25% gradient SDS polyacrylamide gel to determine apparent size and then checked for coagulation activity.

The activity of TF in several disc fractions was determined by coagulation assays with human plasma. Activity was monitored in fractions 25-28 as the inverse of coagulation time. Activity was highest in fraction 25 at 40 and decreased through fraction 28 at 30 $hr^{-1}$. This is expected from the size chromatogram in that the leading edge of the nanoscale disc peak has a larger effective mass due to the incorporation of TF in the MSP-supported bilayer. This assay thus demonstrates that TF is incorporated into nanoscale discs in an active conformation and that the membrane environment of the nanoscale disc closely mimics that of the native membrane system.

Alternatively, rTF-containing nanoscale disc-like particles can be prepared using deoxycholate and Bio-Beads as follows. Purified phospholipids for these studies were obtained from Avanti Polar Lipids (Alabaster, Ala.) and consisted of egg yolk L-α-phosphatidylcholine (PC) and porcine brain L-α-phosphatidylserine (PS), both of which were provided as solutions in chloroform. Before use, aliquots of the phospholipid solutions were dispensed into a glass test tube and the chloroform was evaporated under a stream of nitrogen. To ensure the removal of any traces of remaining chloroform, the dried-down lipids were placed under high vacuum overnight. The next day, the dried phospholipids were dissolved in a solution of 10.4 mM sodium deoxycholate in TBS buffer (50 mM Tris Cl, 100 mM NaCl, 0.1% sodium azide at pH 7.5) to yield a final concentration of 5.2 mM total phospholipid, with sonication being used to facilitate the complete solubilization of the phospholipids. Typically, the phospholipids were mixed to give 80% PC and 20% PS (abbreviated PCPS). Recombinant human TF (rTF) was combined with the solubilized lipid mixture and incubated for 1 hour at room temperature, after which MSP1 was added and incubated at room temperature for an additional 4 hours. The final reaction mixture contained 8 µM rTF and 80 µM MSP1, with a molar ratio of rTF to MSP1 to total phospholipid of 1:10:650. The deoxycholate detergent was then selectively removed from the sample by adsorption to Bio-Beads SM2 (Bio-Rad Laboratories, Hercules, Calif.). This was achieved by adding 0.5 mg washed Bio-Beads per ml of sample and incubating for an additional hour at room temperature with gentle agitation on a rocking platform. The Bio-Beads were then removed by filtration through a 0.22 µM sterilizing filter, yielding a crude preparation of rTF in nanoscale disc-like particles. The sample was then injected into a gel filtration column (10/30 Superdex 200 HR, Pharmacia, Piscataway, N.J.). Samples were eluted with TBS buffer at 0.5 ml per minute and the elution profile monitored by $A_{280}$. Fractions from chromatography were analyzed using an 8-25% gradient SDS polyacrylamide gel to determine apparent size and protein content, and then checked for procoagulant activity. The chromatogram showing elution of rTF incorporated into an excess population of MSP1 nanoscale discs is shown in FIG. 5A.

When desired, the rTF-containing nanoscale discs were further purified by immunoaffinity chromatography using the calcium-dependent antibody, HPC4, essentially as described (Rezaie, A. R. et al. 1992. Protein Expr. Purif. 3:453-460), except that the wash step with 1 M NaCl was not performed because this appeared to disrupt the integrity of the nanodiscs. This purification method takes advantage of the fact that the peptide epitope for the HPC4 antibody was engineered into the N-terminus of recombinant TF. It resulted in an essentially pure population of nanodiscs into which rTF was embedded. When a sample of this highly purified material was rechromatographed on a 10/30 Superdex 200 HR gel filtration column, it eluted as a single, highly homogeneous peak.

The procoagulant activity of TF in disc fractions was determined by clotting assays with pooled human plasma essentially as described (Smith, S. A. and Morrissey, J. H. 2004. J. Thromb. Haemost. 2:1155-1162).

Derivatives of MSP that have a single cysteine residue engineered into the "belt" surrounding Nanodiscs have been designed and prepared. These single cysteine residues have successfully been used to attach compounds that react with sulfydryls, allowing the incorporation of desired chemical functionalities onto Nanodiscs at defined spatial locations. A heterobifunctional crosslinker can be attached to these SH groups. An example of such a crosslinker is APDP (N-[4-(p-Azidosalicylamido) butyl]-3'-(2'-pyridyldithio)propionamide), available from Pierce Biotechnology, Inc., Rockford, Ill. TF-Nanodiscs are prepared using these cysteine-containing versions of MSP by the same methodology as for preparing TF-Nanodiscs using conventional MSP. After TF-Nanodiscs are prepared, they are reacted with APDP as follows (with all of the following steps carried out in the dark): First, 3 mg APDP is dissolved in 50 µl of dimethylsulfoxide (DMSO). Then, 1 microliter of the APDP/DMSO solution is added to 199 µl of phosphate-buffered saline (PBS: 20 mM sodium phosphate, 150 mM NaCl, pH 7.2). The crosslinking reaction is commenced by mixing 0.1 ml of the APDP/PBS solution to 0.3 ml of a preparation of TF-Nanodiscs that had previously been dialyzed into 0.1 M sodium borate buffer, pH 8.4, and allowing the reaction mixture to incubate for 30 minutes at room temperature in the dark. (The TF-Nanodisc preparation in borate buffer can contain up to 2 mg/ml MSP, in order to maintain an excess of APDP over MSP to ensure complete labeling.) Excess unreacted APDP is then separated from labeled TF-Nanodiscs by applying the mixture to a desalting column, such as a D-Salt Execellulose Desalting Column (Pierce Biotechnology, Inc.), that has previously been equilibrated with PBS. TF-Nanodiscs elute in the void volume of such desalting columns, yielding TF-Nanodiscs that are specifically derivatized with APDP on the cysteine residues in the MSP protein.

The APDP-labeled TF-Nanodiscs can be immobilized onto solid supports by photoactivatable crosslinking as follows: The APDP-labeled TF-Nanodiscs are mixed in the dark with the substance to which they are to be crosslinked (for example, collagen sponges). The mixture is then irradiated with an ultraviolet light (302 nm) for 5 minutes at a distance of 3.5 cm at room temperature. Ultraviolet light activates the hydroxyphenyl azide functional group of APDP, allowing it to react covalently and non-selectively with proteins or other organic compounds. Any TF-Nanodiscs that fail to react with the collagen sponge are removed by gentle washing of the sponges with PBS. Once the APD-labeled TF-Nanodiscs have been crosslinked to a solid support, they can be handled in the light.

Examples of publications using APDP to react with free cysteine residues of target proteins, and then crosslinking the derivatized protein to other molecules include, without limitation, Yasui N, and Koide T. J. Am. Chem. Soc. 125:15728-15729, 2003 and van Voorst et al. FEBS Lett. 486:57-62, 2000.

As an alternative to using MSPs with engineered cysteine residues, conventional TF-Nanodiscs (that is, using conventional MSP that do not contain cysteines) can also be immobilized onto solid supports using amine-reactive crosslinking agents such as Sulfo-SASD (Sulfosuccinimidyl-2-[p-azidosalicylamido]ethyl-1,3'-dithiopropionate), also available from Pierce. Sulfo-SASD is reacted with TF-Nanodiscs in the dark according to the manufacturer's directions, which allows the crosslinker to react with primary amines present on the TF-Nanodiscs. The derivatized TF-Nanodiscs are then reacted with solid supports such as collagen sponges using ultraviolet light as above. The final result is immobilized TF-Nanodiscs. This method is slightly less preferable since the site of attachment of the crosslinker to the TF-Nanodiscs cannot be as precisely controlled as with the combination of MSP containing cysteine residues and a sulfhydryl-specific crosslinker such as APDP.

For targeting TF-Nanodiscs to specific anatomic sites in vivo, it is desirable to attach targeting sequences to the TF-Nanodiscs. Targeted TF-Nanodiscs can be used to confer hemostasis or to induce the formation of an occlusive thrombus in the vasculature of a tumor, killing it by infarction. This depends on the in vivo location to which the TF-Nanodiscs are targeted.

Targeting of TF-Nanodiscs to specific in vivo locations can be accomplished in several ways. Monoclonal antibodies specific for desired in vivo targets can be chemically cross-linked to the TF-Nanodiscs using the Sulfo-SASD or APDP crosslinkers as described above. In this case, the crosslinker is first attached to the TF-Nanodiscs using the same methodology described above for immobilizing TF-Nanodiscs on solid supports. Once the crosslinker is attached to TF-Nanodiscs, the purified targeting antibody IgG is added and crosslinking between the TF-Nanodiscs and IgG molecules is initiated by exposing the reaction mixture to ultraviolet light as described above and according to the manufacturer's instructions. Alternatively, fusion proteins between a targeting molecule (such as the antibody combining regions of monoclonal antibodies) and either TF or MSP can be created in order to target TF-Nanodiscs to desired in vivo locations. This can be accomplished as has been described previously by others for making fusion proteins between targeting antibodies and a truncated form of TF (soluble tissue factor, or sTF). In the present invention, however, the membrane-anchored form of TF is used for preparing the fusion proteins. The targeting molecule can be fused either to the N- or C-terminus of membrane TF. As an alternative, the targeting molecule can be fused to either the N- or C-terminus of MSP. The advantages to using fusion proteins with MSP instead of TF is that there is less likelihood of steric hindrance between the TF fusion protein and its ligands (factors VIIa, IX and X) when the targeting molecule is attached to MSP. Alternatively, attaching the targeting molecule to the C-terminus of TF (which is uniquely accessible to the solution in TF-Nanodiscs but not in TF-liposomes) is expected also to avoid problems with steric hindrance, since the targeting molecule is on the other side of the membrane bilayer relative to the ligand binding surface of TF.

Published examples describing how to prepare such targeting molecules using fusion proteins with sTF include Hu et al. 2003. Cancer Res. 63:5046-5053; Nilsson et al. 2001. Cancer Res. 61:711-6; Rippmann et al. 2000. Biochem J. 349 Pt 3:805-812. Examples of specific targeting molecules that can be used to target TF-Nanodiscs include antibody sequences chTNT-3 and chTV-1 (Hu et al. 2003); antibody sequence scFV(L19) (Nilsson et al. 2001) and antibody sequence scSV OS4 (Rippmann et al. 2000); RGD peptide sequence (for example, the amino acid sequence CDCRGDCFC, using the single amino acid abbreviations) (Hu et al. 2003). Any of these targeting molecules could be fused to the N- or C-terminus of either membrane TF or MSP. An important advantage of targeting TF-Nanodiscs instead of sTF using such fusion proteins or cross-linked proteins is the much greater procoagulant activity of TF-Nanodiscs compared with sTF.

The following provides numerous sequences of specifically exemplified MSPs (including the precursor of the naturally occurring apolipoprotein A1) and their coding sequences which could be employed in preparing the TF-nanoscale disc-like particles of the present invention.

TABLE 4

ProApo A-I coding sequence (SEQ ID NO:1)
Restriction sites used in cloning are underlined,
and the translation start and stop signals are
shown in bold.

CCATGGCCCATTTCTGGCAGCAAGATGAACCCCCCCAGAGCCCCTGGGATC
GAGTGAAGGACCTGGCCACTGTGTACGTGGATGTGCTCAAAGACAGCGGCA
GAGACTATGTGTCCCAGTTTGAAGGCTCCGCCTTGGGAAAACAGCTAAACC
TAAAGCTCCTTGACAACTGGGACAGCGTGACCTCCACCTTCAGCAAGCTGC
GCGAACAGCTCGGCCCTGTGACCCAGGAGTTCTGGGATAACCTGGAAAAGG
AGACAGAGGGCCTGAGGCAAGAGATGAGCAAGGATCTGGAGGAGGTGAAGG
CCAAGGTGCAGCCCTACCTGGACGACTTCCAGAAGAAGTGGCAGGAGGAGA
TGGAGCTCTACCGCCAGAAGGTGGAGCCGCTGCGCGCAGAGCTCCAAGAGG
CGCGCGCCAGAAGCTGCACGAGCTGCAAGAGAAGCTGAGCCCACTGGGCG
AGGAGATGCGCGACCGCGCGCGCGCCCATGTGGACGCGCTGCGCACGCATC
TGGCCCCCTACAGCGACGAGCTGCGCCAGCGCTTGGCCGCGCGCCTTGAGG
CTCTCAAGGAGAACGGCGGCGCCAGACTGGCCGAGTACCACGCCAAGGCCA
CCGAGCATCTGAGCACGCTCAGCGAGAAGGCCAAGCCCGCGCTCGAGGACC
TCCGCCAAGGCCTGCTGCCCGTGCTGGAGAGCTTCAAGGTCAGCTTCCTGA
GCGCTCTCGAGGAGTACACTAAGAAGCTCAACACCCAGTAATAAGCTT

TABLE 5

ProApo A-I amino acid sequence (SEQ ID NO:2)

MAHFWQQDEPPQSPWDRVKDLATVYVDVLKDSGRDYVSQFEGSALGKQLN
LKLLLDNWDSVTSTFSKLREQLGPVTQEFWDNLEKETEGLRQEMSKDLEEV
KAKVQPYLDDFQKKWQEEMELYRQKVEPLRAELQEGARQKLHELQEKLSP
LGEEMRDRARAHVDALRTHLAPYSDELRQRLAARLEALKENGGARLAEYH
AKATEHLSTLSEKAKPALEDLRQGLLPVLESFKVSFLSALEEYTKKLNTQ

TABLE 6

Histidine-tagged MSP1 coding sequence
(SEQ ID NO:3). Restriction sites used in cloning
are underlined, and the translation start and stop
signals are shown in bold.

TATACCATGGGCCATCATCATCATCATCATATAGAAGGAAGACTAAAGCT
CCTTGACAACTGGGACAGCGTGACCTCCACCTTCAGCAAGCTGCGCGAAC
AGCTCGGCCCTGTGACCCAGGAGTTCTGGGATAACCTGGAAAAGGAGACA
GAGGGCCTGAGGCAGGAGATGAGCAAGGATCTGGAGGAGGTGAAGGCCAA
GGTGCAGCCCTACCTGGACGACTTCCAGAAGAAGTGGCAGGAGGAGATGG
AGCTCTACCGCCAGAAGGTGGAGCCGCTGCGCGCAGAGCTCCAAGAGGC
GCGCGCCAGAAGCTGCACGAGCTGCAAGAGAAGTTGAGCCCACTGGGCGA
GGAGATGCGCGACCGCGCGCGCGCCCATGTGGACGCGCTGCGCACGCATC
TGGCCCCCTACAGCGACGAGCTGCGCCAGCGCTTGGCCGCGCGCCTTGAG
GCTCTCAAGGAGAACGGCGGCGCCAGACTGGCCGAGTACCACGCCAAGGC
CACCGAGCATCTGAGCACGCTCAGCGAGAAGGCCAAGCCCGCGCTCGAGG
ACCTCCGCCAAGGCCTGCTGCCCGTGCTGGAGAGCTTCAAGGTCAGCTTC
CTGAGCGCTCTCGAGGAGTACACTAAGAAGCTCAACACCCAGTAATAATA
AGCTTGC

TABLE 7

Histidine-tagged MSP1 amino acid sequence
(SEQ ID NO:4)

MGHHHHHHIEGRLKLLDNWDSVTSTFSKLREQLGPVTQEFWDNLEKETEG
LRQEMSKDLEEVKAKVQPYLDDFQKKWQEEMELYRQKVEPLRAELQEGAR
QKLHELQEKLSPLGEEMRDRARAHVDALRTHLAPYSDELRQRLAARLEAL
KENGGARLAEYHAKATEHLSTLSEKAKPALEDLRQGLLPVLESFKVSFLS
ALEEYTKKLNTQ

TABLE 8

Non-Histidine-tagged MSP1 DNA sequence (SEQ ID NO:5).
Restriction sites used in cloning are underlined,
and the translation start and stop signals are
shown in bold.

TACCATGGCAAAGCTCCTTGACAACTGGGACAGCGTGACCTCCACCTTCA
GCAAGCTGCGCGAACAGCTCGGCCCTGTGACCCAGGAGTTCTGGGATAAC
CTGGAAAAGGAGACAGAGGGCCTGAGGCAGGAGATGAGCAAGGATCTGGA
GGAGGTGAAGGCCAAGGTGCAGCCCTACCTGGACGACTTCCAGAAGAAGT
GGCAGGAGGAGATGGAGCTCTACCGCCAGAAGGTGGAGCCGCTGCGCGCA
GAGCTCCAAGAGGCGCGCGCGCCAGAAGCTGCACGAGCTGCAAGAGAAGTT
GAGCCCACTGGGCGAGGAGATGCGCGACCGCGCGCGCGCCCATGTGGACG
CGCTGCGCACGCATCTGGCCCCCTACAGCGACGAGCTGCGCCAGCGCTTG
GCCGCGCGCCTTGAGGCTCTCAAGGAGAACGGCGGCGCCAGACTGGCCGA
GTACCACGCCAAGGCCACCGAGCATCTGAGCACGCTCAGCGAGAAGGCCA
AGCCCGCGCTCGAGGACCTCCGCCAAGGCCTGCTGCCCGTGCTGGAGAGC
TTCAAGGTCAGCTTCCTGAGCGCTCTCGAGGAGTACACTAAGAAGCTCAA
CACCCAGTAATAAGCTTGC

TABLE 9

Non-Histidine-tagged MSP1 amino acid sequence
(SEQ ID NO:6).

MAKLLDNWDSVTSTFSKLREQLGPVTQEFWDNLEKETEGLRQEMSKDLEE
VKAKVQPYLDDFQKKWQEEMELYRQKVEPLRAELQEGARQKLHELQEKLS
PLGEEMRDRARAHVDALRTHLAPYSDELRQRLAARLEALKENGGARLAEY
HAKATEHLSTLSEKAKPALEDLRQGLLPVLESFKVSFLSALEEYTKKLNT
Q

TABLE 10

MSP2 (with histidine tag, without long linker) DNA
sequence (SEQ ID NO:7). The translation start and
stop codons are in bold type, and the restriction
endonuclease recognition sites used in cloning are
underlined.

TATACCATGGGCCATCATCATCATCATCATATAGAAGGAAGACTAAAGCT
CCTTGACAACTGGGACAGCGTGACCTCCACCTTCAGCAAGCTGCGCGAAC
AGCTCGGCCCTGTGACCCAGGAGTTCTGGGATAACCTGGAAAAGGAGACA
GAGGGCCTGAGGCAGGAGATGAGCAAGGATCTGGAGGAGGTGAAGGCCAA
GGTGCAGCCCTACCTGGACGACTTCCAGAAGAAGTGGCAGGAGGAGATGG
AGCTCTACCGCCAGAAGGTGGAGCCGCTGCGCGCAGAGCTCCAAGAGGGC
GCGCGCCAGAAGCTGCACGAGCTGCAAGAGAAGTTGAGCCCACTGGGCGA
GGAGATGCGCGACCGCGCGCGCGCCCATGTGGACGCGCTGCGCACGCATC
TGGCCCCCTACAGCGACGAGCTGCGCCAGCGCTTGGCCGCGCGCCTTGAG
GCTCTCAAGGAGAACGGCGGCGCCAGACTGGCCGAGTACCACGCCAAGGC
CACCGAGCATCTGAGCACGCTCAGCGAGAAGGCCAAGCCCGCGCTCGAGG
ACCTCCGCCAAGGCCTGCTGCCCGTGCTGGAGAGCTTCAAGGTCAGCTTC
CTGAGCGCTCTCGAGGAGTACACTAAGAAGCTCAACACCCAGGGTACCCT
AAAGCTCCTTGACAACTGGGACAGCGTGACCTCCACCTTCAGCAAGCTGC
GCGAACAGCTCGGCCCTGTGACCCAGGAGTTCTGGGATAACCTGGAAAAG
GAGACAGAGGGCCTGAGGCAGGAGATGAGCAAGGATCTGGAGGAGGTGAA
GGCCAAGGTGCAGCCCTACCTGGACGACTTCCAGAAGAAGTGGCAGGAGG
AGATGGAGCTCTACCGCCAGAAGGTGGAGCCGCTGCGCGCAGAGCTCCAA
GAGGGCGCGCGCCAGAAGCTGCACGAGCTGCAAGAAGCTGAGCCCACT
GGGCGAGGAGATGCGCGACCGCGCGCGCGCCCATGTGGACGCGCTGCGCA
CGCATCTGGCCCCCTACAGCGACGAGCTGCGCCAGCGCTTGGCCGCGCGC
CTTGAGGCTCTCAAGGAGAACGGCGGCGCCAGACTGGCCGAGTACCACGC
CAAGGCCACCGAGCATCTGAGCACGCTCAGCGAGAAGGCCAAGCCCGCGC

TABLE 10-continued

MSP2 (with histidine tag, without long linker) DNA sequence (SEQ ID NO:7). The translation start and stop codons are in bold type, and the restriction endonuclease recognition sites used in cloning are underlined.

TCGAGGACCTCCGCCAAGGCCTGCTGCCCGTGCTGGAGAGCTTCAAGGTC
AGCTTCCTGAGCGCTCTCGAGGAGTACACTAAGAAGCTCAACACCCAG**TA
AT**<u>AAGCTT</u>GC

TABLE 11

MSP2 (with histidine tag, without long linker) amino acid sequence (SEQ ID NO:8)

MGHHHHHHIEGRLKLLDNWDSVTSTFSKLREQLGPVTQEFWDNLEKETEG
LRQEMSKDLEEVKAKVQPYLDDFQKKWQEEMELYRQKVEPLRAELQEGAR
QKLHELQEKLSPLGEEMRDRARAHVDALRTHLAPYSDELRQRLAARLEAL
KENGGARLAEYHAKATEHLSTLSEKAKPALEDLRQGLLPVLESFKVSFLS
ALEEYTKKLNTQGTLKLLDNWDSVTSTFSKLREQLGPVTQEFWDNLEKET
EGLRQEMSKDLEEVKAKVQPYLDDFQKKWQEEMELYRQKVEPLRAELQEG
ARQKLHELQEKLSPLGEEMRDRARAHVDALRTHLAPYSDELRQRLAARLE
ALKENGGARLAEYHAKATEHLSTLSEKAKPALEDLRQGLLPVLESFKVSF
LSALEEYTKKLNTQ

TABLE 12

MSP2L (with histidine tag, with long linker) DNA sequence (SEQ ID NO:9). Translation start and stop codons are in bold type; restriction endonuclease recognition sites used in cloning are underlined.

TA<u>CCATGG</u>GGCCATCATCATCATCATCATATAGAAGGAAGACTAAAGCTCC
TTGACAACTGGGACAGCGTGACCTCCACCTTCAGCAAGCTGCGCGAACAG
CTCGGCCCTGTGACCCAGGAGTTCTGGGATAACCTGGAAAAGGAGACAGA
GGGGCCTGAGGCAGGAGATGAGCAAGGATCTGGAGGAGGTGAAGGCCAAG
TGCAGCCCTACCTGGACGACTTCCAGAAGAAGTGGCAGGAGGAGATGGAG
CTCTACCGCCAGAAGGTGGAGCCGCTGCGCGAGAGCTCCAAGAGGGCGC
GCGCCAGAAGCTGCACGAGCTGCAAGAGAAGCTGAGCCCACTGGGCGAGG
AGATGCGCGACCGCGCGCGCGCCCATGTGGACGCGCTGCGCACGCATCTG
GCCCCCTACAGCGACGAGCTGCGCCAGCGCTTGGCCGCGCGCCTTGAGGC
TCTCAAGGAGAACGGCGGCGCCAGACTGGCCGAGTACCACGCCAAGGCCA
CCGAGCATCTGAGCACGCTCAGCGAGAAGGCCAAGCCCGCGCTCGAGGAC
CTCCGCCAAGGCCTGCTGCCCGTGCTGGAGAGCTTCAAGGTCAGCTTCCT
GAGCGCTCTCGAGGAGTACACTAAGAAGCTCAACACCCAGGGTACCGGTG
GAGGTAGTGGAGGTGGTACCCTAAAGCTCCTTGACAACTGGGACAGCGTG
ACCTCCACCTTCAGCAAGCTGCGCGAACAGCTCGGCCCTGTGACCCAGGA
GTTCTGGGATAACCTGGAAAAGGAGACAGAGGGGCCTGAGGCAGGAGATGA
GCAAGGATCTGGAGGAGGTGAAGGCCAAGGTGCAGCCCTACCTGGACGAC
TTCCAGAAGAAGTGGCAGGAGGAGATGGAGCTCTACCGCCAGAAGGTGGA
GCCGCTGCGCGCAGAGCTCCAAGAGGGCGCGCGCCAGAAGCTGCACGAGC
TGCAAGAGAAGCTGAGCCCACTGGGCGAGGAGATGCGCGACCGCGCGCGC
GCCCATGTGGACGCGCTGCGCACGCATCTGGCCCCCTACAGCGACGAGCT
GCGCCAGCGCTTGGCCGCGCGCCTTGAGGCTCTCAAGGAGAACGGCGGCG
CCAGACTGGCCGAGTACCACGCCAAGGCCACCGAGCATCTGAGCACGCTC
AGCGAGAAGGCCAAGCCCGCGCTCGAGGACCTCCGCCAAGGCCTGCTGCC
CGTGCTGGAGAGCTTCAAGGTCAGCTTCCTGAGCGCTCTCGAGGAGTACA
CTAAGAAGCTCAACACCCAGTAA<u>AAGCTT</u>GC

TABLE 13

MSP2 (with histidine tag, with long linker, in bold type) amino acid sequence (SEQ ID NO:10).

MGHHHHHHIEGRLKLLDNWDSVTSTFSKLREQLGPVTQEFWDNLEKETEG
LRQEMSKDLEEVKAKVQPYLDDFQKKWQEEMELYRQKVEPLRAELQEGAR
QKLHELQEKLSPLGEEMRDRARAHVDALRTHLAPYSDELRQRLAARLEAL
KENGGARLAEYHAKATEHLSTLSEKAKPALEDLRQGLLPVLESFKVSFLS
ALEEYTKKLNTQGTGGGSGGGTLKLLDNWDSVTSTFSKLREQLGPVTQEF
WDNLEKETEGLRQEMSKDLEEVKAKVQPYLDDFQKKWQEEMELYRQKVEP

TABLE 13-continued

MSP2 (with histidine tag, with long linker, in bold type) amino acid sequence (SEQ ID NO:10).

LRAELQEGARQKLHELQEKLSPLGEEMRDRARAHVDALRTHLAPYSDELR
QRLAARLEALKENGGARLAEYHAKATEHLSTLSEKAKPALEDLRQGLLPV
LESFKVSFLSALEEYTKKLNTQ

TABLE 14

MSP1D5D6 DNA sequence (SEQ ID NO:11). Translations start and stop codons are in bold type; restriction endonuclease recognition sites are underlined.

TATA<u>CCATGG</u>GGCCATCATCATCATCATCATATAGAAGGAAGACTAAAGCT
CCTTGACAACTGGGACAGCGTGACCTCCACCTTCAGCAAGCTGCGCGAAC
AGCTCGGCCCTGTGACCCAGGAGTTCTGGGATAACCTGGAAAAGGAGACA
GAGGGGCCTGAGGCAGGAGATGAGCAAGGATCTGGAGGAGGTGAAGGCCAA
GGTGCAGCCCTACCTGGACGACTTCCAGAAGAAGTGGCAGGAGGAGATGG
AGCTctaccgccagaaggtggagcCCTACAGCGACGAGCTGCGCCAGCGC
TTGGCCGCGCGCCTTGAGGCTCTCAAGGAGAACGGCGGCGCCAGACTGGC
CGAGTACCACGCCAAGGCCACCGAGCATCTGAGCACGCTCAGCGAGAAGG
CCAAACCCGCGCTCGAGGACCTCCGCCAAGGCCTGCTGCCCGTGCTGGAG
AGCTTCAAGGTCAGCTTCCTGAGCGCTCTCGAGGAGTACACTAAGAAGCT
CAACACCCAGTAA<u>AAGCTT</u>GC

TABLE 15

MSP1D5D6 amino acid sequence (SEQ ID NO:12).

MGHHHHHHIEGRLKLLDNWDSVTSTFSKLREQLGPVTQEFWDNLEKETEG
LRQEMSKDLEEVKAKVQPYLDDFQKKWQEEMELYRQKVEPYSDELRQRLA
ARLEALKENGGARLAEYHAKATEHLSTLSEKAKPALEDLRQGLLPVLESF
KVSFLSALEEYTKKLNTQ

TABLE 16

MSP1D6D7 DNA sequence (SEQ ID NO:13). Translation start and stop codons are shown in bold type, and restriction endonuclease recognition sites used in cloning are underlined.

TATA<u>CCATGG</u>GGCCATCATCATCATCATCATATAGAAGGAAGACTAAAGCT
CCTTGACAACTGGGACAGCGTGACCTCCACCTTCAGCAAGCTGCGCGAAC
AGCTCGGCCCTGTGACCCAGGAGTTCTGGGATAACCTGGAAAAGGAGACA
GAGGGGCCTGAGGCAGGAGATGAGCAAGGATCTGGAGGAGGTGAAGGCCAA
GGTGCAGCCCTACCTGGACGACTTCCAGAAGAAGTGGCAGGAGGAGATGG
AGCTCTACCGCCAGAAGGTGGAGCCGCTGCGCGAGAGCTCCAAGAGGGC
GCGCCAGAAGCTGCACGAGCTGCAAGAGAAGTTGAGCGCAGGCTAGC
CGAGTACCACGCCAAGGCCACCGAGCATCTGAGCACGCTCAGCGAGAAGG
CCAAACCCGCGCTCGAGGACCTCCGCCAAGGCCTGCTGCCCGTGCTGGAG
AGCTTCAAGGTCAGCTTCCTGAGCGCTCTCGAGGAGTACACTAAGAAGCT
CAACACCCAGTAA<u>AAGCTT</u>GC

TABLE 17

MSP1D6D7 amino acid sequence (SEQ ID NO:14).

MGHHHHHHIEGRLKLLDNWDSVTSTFSKLREQLGPVTQEFWDNLEKETEG
LRQEMSKDLEEVKAKVQPYLDDFQKKWQEEMELYRQKVEPLRAELQEGAR
QKLHELQEKLSARLAEYHAKATEHLSTLSEKAKPALEDLRQGLLPVLESF
KVSFLSALEEYTKKLNTQ

TABLE 18

Full synthetic gene sequence for MSP1
(SEQ ID NO:15). Restriction sites used in cloning
are underlined, and the translation start and stop
signals are shown in bold.

AC<u>CATGG</u>GTCATCATCATCATCATCACATTGAGGGACGTCTGAAGCTGTT
GGACAATTGGGACTCTGTTACGTCTACCTTCAGTAAACTTCGCGAACAAC
TGGGCCCCGTGACGCAGGAATTCTGGGACAACCTGGAAAAAGAAACCGAG
GGACTGCGTCAGGAAATGTCCAAAGATTTAGAAGAGGTGAAGGCCAAGGT
TCAGCCATATCTAGATGACTTTCAGAAAAAATGGCAGGAAGAGATGGAAT
TATATCGTCAAAAGGTGGAACCGCTGCGTGCGGAACTGCAAGAGGGGCA
CGCCAAAAACTCCATGAGCTCCAAGAGAAGCTCAGCCCATTAGGCGAAGA
AATGCGCGATCGCGCCCGTGCACATGTTGATGCACTCCGGACTCATTTGG
CGCCGTATTCGGATGAACTTCGCCAGCGTTTGGCCGCACGTCTCGAGGCG
CTGAAAGAAAACGGGGGTGCCCGCTTGGCTGAGTACCACGCGAAAGCGAC
AGAACACCTGAGCACCTTGAGCGAAAAAGCGAAACCGGCGCTGGAAGATC
TACGCCAGGGCTTATTGCCTGTTCTTGAGAGCTTTAAAGTCAGTTTTCTG
TCAGCTCTGGAAGAATATACTAAAAAGCTGAATACCCAGTAA<u>AAGCTTG</u>
G

The following is the amino acid sequence of a MSP polypeptide in which half repeats are deleted:

TABLE 19

MSP1D3 (SEQ ID NO:16).

MGHHHHHHIEGRLKLLDNWDSVTSTFSKLREQLGPVTQEFWDNLEKETEG
LRQEMSPYLDDFQKKWQEEMELYRQKVEPLRAELQEGARQKLHELQEKLS
PLGEEMRDRARAHVDALRTHLAPYSDELRQRLAARLEALKENGGARLAEY
HAKATEHLSTLSEKAKPALEDLRQGLLPVLESFKVSFLSALEEYTKKLNT
Q

TABLE 20

MSP1D9 (SEQ ID NO:17).

MGHHHHHHIEGRLKLLDNWDSVTSTFSKLREQLGPVTQEFWDNLEKETEG
LRQEMSKDLEEVKAKVQPYLDDFQKKWQEEMELYRQKVEPLRAELQEGAR
QKLHELQEKLSPLGEEMRDRARAHVDALRTHLAPYSDELRQRLAARLEAL
KENGGARLAEYHAKATEHLSTLSEKAKPVLESFKVSFLSALEEYTKKLNT
Q

TABLE 21

MSP tandem repeat with first half-repeats deleted
(MSP2delta1) (SEQ ID NO:18)

MGHHHHHHIEGRLKLLDNWDSVTSTFSKLREQLGPVTQEFWDNLEKETEG
LRQEMSPYLDDFQKKWQEEMELYRQKVEPLRAELQEGARQKLHELQEKLS
PLGEEMRDRARAHVDALRTHLAPYSDELRQRLAARLEALKENGGARLAEY
HAKATEHLSTLSEKAKPALEDLRQGLLPVLESFKVSFLSALEEYTKKLNT
QGTLKLLDNWDSVTSTFSKLREQLGPVTQEFWDNLEKETEGLRQEMSPYL
DDFQKKWQEEMELYRQKVEPLRAELQEGARQKLHELQEKLSPLGEEMRDR
ARAHVDALRTHLAPYSDELRQRLAARLEALKENGGARLAEYHAKATEHLS
TLSEKAKPALEDLRQGLLPVLESFKVSFLSALEEYTKKLNTQ

Plasmids for the expression of extended MSPs were constructed from plasmid for MSP1 described in Bayburt et al. (2002) *Nanoletters* 2:853-856 using a "Seamless" cloning kit (Stratagene) according to the manufacturer recommendations. An alternative N-terminus for MSP1TEV was added by PCR; the primers were designed to include Nco I and Hind III restriction sites. The PCR product was cloned into the pET28a plasmid (Novagen). Truncated mutants of MSP were produced with a Quick-change kit (Stratagene) using the MSP1TEV plasmid as a template. The presence of the desired insertions or deletions and absence of PCR-induced mutations were verified by DNA sequencing.

Expression and purification of the MSP proteins was performed as described herein. Protein purity was characterized by SDS-PAGE and Electrospray Mass Spectrometry; it was found to be greater than 95%. The TEV protease expression system was purchased (Science Reagents, Inc., Atlanta, Ga.) and used after some minor modifications. The sequences of new scaffold proteins were optimized with respect to salt link scores for the belt model of the antiparallel dimer as described in Segrest et al. (1999) *J. Biol. Chem.* 274:31755-31758. At first, the amino acid sequences of the extended mutants were generated so that each of the central helices (from H3 to H7) was inserted sequentially at every position between other central helices, i.e. after H3, H4, H5, and H6, and the number of favorable salt links minus number of unfavorable contacts of the same charges was calculated for all possible configurations of antiparallel dimers in the resulting scaffold protein (Segrest (1999) supra). As a result, the insertion mutants were selected as optimal for maximum salt link scores. These extended scaffold proteins, as well as truncated scaffold proteins, also containing different tag sequences at the N. terminus, were engineered in *E. coli* and expressed with a high yield and purified by standard procedures.

With reference to the following protein and DNA sequences, the MSPs we have utilized can be summarized as the following linked structures. Note H1, H2 refer to the sequences of Helix #1 etc. His is a (His)6 tag, TEV is the tobacco viral protease, X is the Factor X (ten) protease site.

TABLE 22

Amino Acid Sequences of MSP Building Blocks

| | |
|---|---|
| GLOB | DEPPQSPWDRVKDLATVYVDVLKDSGRDYVSQFEGSALGKQLN (SEQ ID NO:21) |
| HisX | MGHHHHHHIEGR (SEQ ID NO:20) |
| HisTEV | MGHHHHHHHDYDIPTTENLYFQG (SEQ ID NO:21) |
| Helix 1 (H1): | LKLLDNWDSVTSTFSKLREQLG (SEQ ID NO:22) |
| Helix 2 (H2): | PVTQEFWDNLEKETEGLRQEMS (SEQ ID NO:23) |
| Helix 3 (H3): | KDLEEVKAKVQ (SEQ ID NO:24) |
| Helix 4 (H4): | PYLDDFQKKWQEEMELYRQKVE (SEQ ID NO:25) |
| Helix 5 (H5): | PLRAELQEGARQKLHELQEKLS (SEQ ID NO:26) |
| Helix 6 (H6): | PLGEEMRDRARAHVDALRTHLA (SEQ ID NO:27) |
| Helix 7 (H7): | PYSDELRQRLAARLEALKENGG (SEQ ID NO:28) |
| Helix 8 (H8): | ARLAEYHAKATEHLSTLSEKAK (SEQ ID NO:29) |
| Helix 9 (H9): | PALEDLRQGLL (SEQ ID NO:30) |
| Helix 10(H10): | PVLESFKVSFLSALEEYTKKLNTQ (SEQ ID NO:31) |
| Helix 0.5(H0.5): | STFSKLREQLG (SEQ ID NO:32) |

TABLE 22-continued

Amino Acid Sequences of MSP Building Blocks

Helix 10.5 (H10.5): SALEEYTKKLNTQ
(SEQ ID NO:33)

Helix 2S (H2): PVTQEFWDNLEKETEGLRQEMS
(SEQ ID NO:34)

TABLE 23

Sequences encoding the MSP Building Blocks of Table 22.

| | |
|---|---|
| HisX | ATGGGTCATCATCATCATCATCACATTGAGGG ACGT (SEQ ID NO:35) |
| HisTEV | ATGGGTCATCATCATCATCATCATCACGATTA TGATATTCCTACTACTGAGAATTTGTATTTTC AGGGT (SEQ ID NO:36) |
| Helix 1 (H1): | CTGAAGCTGTTGGACAATTGGGACTCTGTTAC GTCTACCTTCAGTAAACTTCGCGAACAACTGG GC (SEQ ID NO:37) |
| Helix 2 (H2): | CCCGTGACGCAGGAATTCTGGGACAACCTGGA AAAAGAAACCGAGGGACTGCGTCAGGAAATGT CC (SEQ ID NO:38) |
| Helix 3 (H3): | AAAGATTTAGAAGAGGTGAAGGCCAAGGTTCA G (SEQ ID NO:39) |
| Helix 4 (H4): | CCATATCTCGATGACTTTCAGAAAAAATGGCA GGAAGAGATGGAATTATATCGTCAAAAGGTGG AA (SEQ ID NO:40) |
| Helix 5 (H5): | CCGCTGCGTGCGGAACTGCAAGAGGGGGCACG CCAAAAACTCCATGAGCTCCAAGAGAAGCTCA GC (SEQ ID NO:41) |
| Helix 6 (H6): | CCATTAGGCGAAGAAATGCGCGATCGCGCCCG TGCACATGTTGATGCACTCCGGACTCATTTGG CG (SEQ ID NO:42) |
| Helix 7 (H7): | CCGTATTCGGATGAACTTCGCCAGCGTTTGGC CGCACGTCTCGAGGCGCTGAAAGAAAACGGGG GT (SEQ ID NO:43) |
| Helix 8 (H8): | GCCCGCTTGGCTGAGTACCACGCGAAAGCGAC AGAACACCTGAGCACCTTGAGCGAAAAAGCGA AA (SEQ ID NO:44) |
| Helix 9 (H9): | CCGGCGCTGGAAGATCTACGCCAGGGCTTATT G (SEQ ID NO:45) |
| Helix 10 (H10): | CCTGTTCTTGAGAGCTTTAAAGTCAGTTTTCT GTCAGCTCTGGAAGAATATACTAAAAAGCTGA ATACCCAG (SEQ ID NO:46) |
| Helix 0.5 (H0.5): | TCTACCTTCAGTAAACTTCGCGAACAACTGGG C (SEQ ID NO:47) |
| Helix10.5 (H10.5): | CAGTTTTCTGTCAGCTCTGGAAGAATATACTA AAAAGCTGAATACCCAG (SEQ ID NO:48) |
| Helix 2S (H2S): | TCCGTGACGCAGGAATTCTGGGCAACCTGGA AAAAGAAACCGAGGGACTGCGTCAGGAAATGT CC (SEQ ID NO:49) |

Several particular MSP sequences useful in the present invention are the following combinations of the above sequences, as given in Table 24 and others.

TABLE 24

Engineered MSPs Useful in Nanodisc Preparation

| | |
|---|---|
| MSP1 | HisX-H1-H2-H3-H4-H5-H6-H7-H8-H9-H10 (SEQ ID NO:3) |
| MSP1E1 | HisX-H1-H2-H3-H4-H4-H5-H6-H7-H8-H9-H10 (SEQ ID NO:50) |
| MSP1E2 | HisX-H1-H2-H3-H4-H5-H4-H5-H6-H7-H8-H9-H10 (SEQ ID NO:51) |
| MSP1E3 | HisX-H1-H2-H3-H4-H5-H6-H4-H5-H6-H7-H8-H9-H10 (SEQ ID NO:52) |
| MSP1TEV | HisTev-H1-H2-H3-H4-H5-H6-H7-H8-H9-H10 (SEQ ID NO:53) |
| MSP1NH | H1-H2-H3-H4-H5-H6-H7-H8-H9-H10 (SEQ ID NO:54) |
| MSP1T2 | HisTev-H0.5-H2-H3-H4-H5-H6-H7-H8-H9-H10 (SEQ ID NO:55) |
| MSP1T2NH | H0.5-H2-H3-H4-H5-H6-H7-H8-H9-H10 (SEQ ID NO:56) |
| MSP1T3 | HisTev-H2-H3-H4-H5-H6-H7-H8-H9-H10 (SEQ ID NO:57) |
| MSP1D3 | HisX-H1-H2-H4-H5-H6-H7-H8-H9-H10 (SEQ ID NO:16) |
| MSP1D9 | HisX-H1-H2-H3-H4-H5-H6-H7-H8-H10 (SEQ ID NO:17) |
| MSP1D5D6 | HisX-H1-H2-H3-H4-H7-H8-H9-H10 (SEQ ID NO:12) |
| MSP1D6D7 | HisX-H1-H2-H3-H4-H5-H8-H9-H10 (SEQ ID NO:14) |
| MSP1D3D9 | HisX-H1-H2-H4-H5-H6-H7-H8-H10 (SEQ ID NO:58) |
| MSP1D10.5 | HisX-H1-H2-H3-H4-H5-H6-H7-H8-H9-H10.5 (SEQ ID NO:59) |
| MSP1D3D10.5 | HisX-H1-H2-H4-H5-H6-H7-H8-H9-H10.5 (SEQ ID NO:60) |
| MSP1T4 | HisTEV-H25-H3-H4-H5-H6-H7-H8-H9-H10 (SEQ ID NO:61) |
| Apo A-I | GLOB-H1-H2-H3-H4-H4-H5-H6-H5-H6-H7-H8-H9-H10 (SEQ ID NO:2, exclusive of the signal peptide) |
| MSP1T5 | HisTev-H2.5-H3-H4-H5-H6-H7-H8-H9-H10 (SEQ ID NO:62) |
| MSP1T6 | HisTev-H3-H4-H5-H6-H7-H8-H9-H10 (SEQ ID NO:63) |
| MSP1E3TEV: | HisTev-H1-H2-H3-H4-H5-H6-H4-H5-H6-H7-H8-H9-H10 (SEQ ID NO:64) |
| MSP1E3D1: | HisTev-H0.5-H2-H3-H4-H5-H6-H4-H5-H6-H7-H8-H9-H10 (SEQ ID NO:65) |
| MSP2TEV: | HisTev-H1-H2-H3-H4-H5-H6-H7-H8-H9-H10-GT-H1-H2-H3-H4-H5-H6-H7-H8-H9-H10 (SEQ ID NO:66) |
| MSP1N1: | His-TEV-H2S-H3-H4-H4-H5-H6-H7-H8-H9 (SEQ ID NO:67) |
| MSP2N1: | HisTev-H0.5-H2-H3-H4-H5-H6-H7-H8-H9-H10-GT-H0.5-H2-H3-H4-H5-H6-H7-H8-H9-H10 (SEQ ID NO:68) |

TABLE 24-continued

Engineered MSPs Useful in Nanodisc Preparation

MSP2N2: HisTev-H0.5-H2-H3-H4-H5-H6-H7-H8-H9-
H10-GT-H2-H3-H4-H5-H6-H7-H8-H9-H10
(SEQ ID NO:69)

In addition to these sequences, there are two fusion protein (tandem repeat MSP) constructs of reference. These are composed of two MSP1 constructs linked by a Gly-Thr linker:

```
MSP2 (MSP1-Gly-Thr-MSP1, SEQ ID NO:8)
and

MSP2D1D1
(MSP1T3-Gly-Thr-H2-H3-H4-H5-H6-H7-H8-H9-H10,
SEQ ID NO:70).
```

Other constructs that can be readily produced include permutations of the above, i.e., MSP1 or a tandemly repeated MSP with either a short or long linker sequence with any combination of the following: hinge deletion, hinge replacement, half-repeat deletion, histidine tag, different linkers for MSP2 analogs.

The coding and amino acid sequences of MSP1T4 are given in Tables 25 and 26, respectively.

TABLE 25

DNA sequence encoding MSP1T4 (SEQ ID NO:71)

atgggtcatcatcatcatcatcatcacgattatgatattcctactactga
gaatttgtattttcagggttccgtgacgcaggaattctgggacaacctgg
aaaaagaaaccgagggactgcgtcaggaaatgtccaaagatttagaagag
gtgaaggccaaggttcagccatatctcgatgactttcagaaaaaatggca
ggaagagatggaattatatcgtcaaaaggtggaaccgctgcgtgcggaac
tgcaagaggggcacgccaaaaactccatgagctccaagagaagctcagc
ccattaggcgaagaaatgcgcgatcgcgcccgtgcacatgttgatgcact
ccggactcatttggcgccgtattcggatgaacttcgccagcgtttggccg
cacgtctcgaggcgctgaaagaaacgggggtgcccgcttggctgagtac
cacgcgaaagcgacagaacacctgagcaccttgagcgaaaaagcgaaacc
ggcgctggaagatctacgccagggcttattgcctgttcttgagagcttta
aagtcagttttctgtcagctctggaagaatatactaaaaagctgaatacc
cag
```

TABLE 26

Amino acid sequence of MSP1T4 (SEQ ID NO:61)

MGHHHHHHHDYDIPTTENLYFQGSVTQEFWDNLEKETEGLRQEMSKDLEE
VKAKVQPYLDDFQKKWQEEMELYRQKVEPLRAELQEGARQKLHELQEKLS
PLGEEMRDRARAHVDALRTHLAPYSDELRQRLAARLEALKENGGARLAEY
HAKATEHLSTLSEKAKPALEDLRQGLLPVLESFKVSFLSALEEYTKKLNT
Q

In the schematic for MSP1T5, H2.5 indicates the second half of the H2 helical sequence, i.e. the last 33 nucleotides or 11 amino acids is not included in the MSP sequence. The coding and amino acid sequence for this protein is given in Tables 27 and 28, respectively.

TABLE 27

DNA sequence encoding MSP1T5 (SEQ ID NO:72)

atgggtcatcatcatcatcatcatcacgattatgatattcctactactga
gaatttgtattttcagggtaaagaaaccgagggactgcgtcaggaaatgt
ccaaagatttagaagaggtgaaggccaaggttcagccatatctcgatgac TABLE 27-continued DNA sequence encoding MSP1T5 (SEQ ID NO:72)

tttcagaaaaaatggcaggaagagatggaattatatcgtcaaaaggtgga
accgctgcgtgcggaactgcaagagggggcacgccaaaaactccatgagc
tccaagagaagctcagcccattaggcgaagaaatgcgcgatcgcgcccgt
gcacatgttgatgcactccggactcatttggcgccgtattcggatgaact
tcgccagcgtttggccgcacgtctcgaggcgctgaaagaaacgggggtg
cccgcttggctgagtaccacgcgaaagcgacagaacacctgagcaccttg
agcgaaaaagcgaaaccggcgctggaagatctacgccagggcttattgcc
tgttcttgagagctttaaagtcagttttctgtcagctctggaagaatata
ctaaaaagctgaatacccag

TABLE 28

Amino acid sequence of MSP1T5 (SEQ ID NO:62)

MGHHHHHHHDYDIPTTENLYFQGKEIEGLRQEMSKDLEEVKAKVQPYLDD
FQKKWQEEMELYRQKVEPLRAELQEGARQKLHELQEKLSPLGEEMRDRAR
AHVDALRTHLAPYSDELRQRLAARLEALKENGGARLAEYHAKATEHLSTL
SEKAKPALEDLRQGLLPVLESFKVSFLSALEEYTKKLNTQ

TABLE 29

DNA sequence encoding MSP1T6 (SEQ ID NO: 73)

atgggtcatcatcatcatcatcatcacgattatgatattcctactactga
gaatttgtattttcagggtaaagatttagaagaggtgaaggccaaggttc
agccatatctcgatgactttcagaaaaaatggcaggaagagatggaatta
tatcgtcaaaaggtggaaccgctgcgtgcggaactgcaagagggggcacg
ccaaaaactccatgagctccaagagaagctcagcccattaggcgaagaaa
tgcgcgatcgcgcccgtgcacatgttgatgcactccggactcatttggcg
ccgtattcggatgaacttcgccagcgtttggccgcacgtctcgaggcgct
gaaagaaacgggggtgcccgcttggctgagtaccacgcgaaagcgacag
aacacctgagcaccttgagcgaaaaagcgaaaccggcgctggaagatcta
cgccagggcttattgcctgttcttgagagctttaaagtcagttttctgtc
agctctggaagaatatactaaaaagctgaatacccag

TABLE 30

Amino acid sequence of MSP1T6 (SEQ ID NO:63)

MGHHHHHHHDYDIPTTENLYFQGKDLEEVKAKVQPYLDDFQKKWQEEMEL
YRQKVEPLRAELQEGARQKLHELQEKLSPLGEEMRDRARAHVDALRTHLA
PYSDELRQRLAARLEALKENGGARLAEYHAKATEHLSTLSEKAKPALEDL
RQGLLPVLESFKVSFLSALEEYTKKLNTQ

MSP1T5 and MSP1T6 discs preps are not homogeneous under all assembly conditions. The results are highly dependent on the particular assembly conditions.

In the following MSP construct (MSP1N1), H10 is not included, and two H4 motifs are inserted. The coding and amino acid sequences are given in Tables 31 and 32, respectively. This MSP is designed to increase the number of possible salt bridges on the interhelical interface.

TABLE 31

DNA sequence encoding MSP1N1 (SEQ ID NO:74)

atgggtcatcatcatcatcatcatcacgattatgatattcctactactga
gaatttgtattttcagggttccgtgacgcaggaattctgggacaacctgg
aaaaagaaaccgagggactgcgtcaggaaatgtccaaagatttagaagag
gtgaaggccaaggttcagccatatctcgatgactttcagaaaaaatggca
ggaagagatggaattatatcgtcaaaaggtggaaccatatctcgatgact
ttcagaaaaaatggcaggaagagatggaattatatcgtcaaaaggtggaa
ccgctgcgtgcggaactgcaagagggggcacgccaaaaactccatgagct
ccaagagaagctcagcccattaggcgaagaaatgcgcgatcgcgcccgtg
cacatgttgatgcactccggactcatttggcgccgtattcggatgaactt
cgccagcgtttggccgcacgtctcgaggcgctgaaagaaacgggggtgc

TABLE 31-continued

DNA sequence encoding MSP1N1 (SEQ ID NO:74)

ccgcttggctgagtaccacgcgaaagcgacagaacacctgagcaccttga
gcgaaaaagcgaaaccggcgctggaagatctacgccagggcttattg

TABLE 32

Amino acid sequence of MSPINI (SEQ ID NO:67)

MGHHHHHHHDYDIPTTENLYFQGSVTQEFWDNLEKETEGLRQEMSKDLEE
VKAKVQPYLDDFQKKWQEEMELYRQKVEPYLDDFQKKWQEEMELYRQKVE
PLRAELQEGARQKLHELQEKLSPLGEEMRDRARAHVDALRTHLAPYSDEL
RQRLAARLEALKENGGARLAEYHAKATEHLSTLSEKAKPALEDLRQGLL

The following "extended" MSPs incorporate a cleavable His-tag and use a TEV protease recognition site.

TABLE 33

DNA sequence encoding MSP1E3TEV
(HisTev-H1-H2-H3-H4-H5-H6-H4-H5-H6-H7-H8-H9-H10)
(SEQ ID NO:75)

atgggtcatcatcatcatcatcatcacgattatgatattcctactactga
gaatttgtattttcagggtctgaagctgttggacaattgggactctgtta
cgtctaccttcagtaaacttcgcgaacaactgggccccgtgacgcaggaa
ttctgggacaacctggaaaaagaaaccgagggactgcgtcaggaaatgtc
caaagatttagaagaggtgaaggccaaggttcagccatatctcgatgact
ttcagaaaaaatggcaggaagagatggaattatatcgtcaaaaggtggaa
ccgctgcgtgcggaactgcaagaggggcacgccaaaaactccatgagct
ccaagagaagctcagcccattaggcgaagaaatgcgcgatcgcgcccgtg
cacatgttgatgcactccggactcatttggcgccatatctcgatgactt
cagaaaaaatggcaggaagagatggaattatatcgtcaaaaggtggaacc
gctgcgtgcggaactgcaagaggggcacgccaaaaactccatgagctcc
aagagaagctcagcccattaggcgaagaaatgcgcgatcgcgcccgtgca
catgttgatgcactccggactcatttggcgccgtattcggatgaacttcg
ccagcgtttggccgcacgtctcgaggcgctgaaagaaaacggggtgccc
gcttggctgagtaccacgcgaaagcgacagaacacctgagcaccttgagc
gaaaaagcgaaaccggcgctggaagatctacgccagggcttattgcctgt
tcttgagagctttaaagtcagttttctgtcagctctggaagaatatacta
aaaagctgaatacccag

TABLE 34

Amino acid sequence of MSP1E3TEV (SEQ ID NO:64)

MGHHHHHHHDYDIPTTENLYFQGLKLLDNWDSVTSTFSKLREQLGPVTQE
FWDNLEKETEGLRQEMSKDLEEVKAKVQPYLDDFQKKWQEEMELYRQKVE
PLRAELQEGARQKLHELQEKLSPLGEEMRDRARAHVDALRTHLAPYLDDF
QKKWQEEMELYRQKVEPLRAELQEGARQKLHELQEKLSPLGEEMRDRARA
HVDALRTHLAPYSDELRQRLAARLEALKENGGARLAEYHAKATEHLSTLS
EKAKPALEDLRQGLLPVLESFKVSFLSALEEYTKKLNTQ

TABLE 35

DNA sequence encoding MSP1E3D1 (SEQ ID NO:76)
(HisTev-H0.5-H2-H3-H4-H5-H6-H4-H5-H6-H7-H8-H9-H10)

atgggtcatcatcatcatcatcatcacgattatgatattcctactactga
gaatttgtattttcagggtctgaccttcagtaaacttcgcgaacaactgg
gccccgtgacgcaggaattctgggacaacctggaaaaagaaaccgaggga
ctgcgtcaggaaatgtccaaagatttagaagaggtgaaggccaaggttca
gccatatctcgatgactttcagaaaaaatggcaggaagagatggaattat
atcgtcaaaaggtggaaccgctgcgtgcggaactgcaagaggggcacgc
caaaaactccatgagctccaagagaagctcagcccattaggcgaagaaat
gcgcgatcgcgcccgtgcacatgttgatgcactccggactcatttggcgc
catatctcgatgactttcagaaaaaatggcaggaagagatggaattatat
cgtcaaaaggtggaaccgctgcgtgcggaactgcaagaggggcacgcca
aaaactccatgagctccaagagaagctcagcccattaggcgaagaaatgc
gcgatcgcgcccgtgcacatgttgatgcactccggactcatttggcgccg

TABLE 35-continued

DNA sequence encoding MSP1E3D1 (SEQ ID NO:76)
(HisTev-H0.5-H2-H3-H4-H5-H6-H4-H5-H6-H7-H8-H9-H10)

tattcggatgaacttcgccagcgtttggccgcacgtctcgaggcgctgaa
agaaaacggggtgcccgcttggctgagtaccacgcgaaagcgacagaac
acctgagcaccttgagcgaaaaagcgaaaccggcgctggaagatctacgc
cagggcttattgcctgttcttgagagctttaaagtcagttttctgtcagc
tctggaagaatatactaaaaagctgaatacccag

TABLE 36

Amino acid sequence of MSP1E3D1 (SEQ ID NO:65)

MGHHHHHHHDYDIPTTENLYFQGSTFSKLREQLGPVTQEFWDNLEKETEG
LRQEMSKDLEEVKAKVQPYLDDFQKKWQEEMELYRQKVEPLRAELQEGAR
QKLHELQEKLSPLGEEMRDRARAHVDALRTHLAPYLDDFQKKWQEEMELY
RQKVEPLRAELQEGARQKLHELQEKLSPLGEEMRDRARAHVDALRTHLAP
YSDELRQRLAARLEALKENGGARLAEYHAKATEHLSTLSEKAKPALEDLR
QGLLPVLESFKVSFLSALEEYTKKLNTQ

A protein corresponding to MSP2 with a N-terminal TEV cleavable His-tag has been designed. The coding and amino acid sequences are given in Tables 37 and 38, respectively.

TABLE 37

DNA sequence encoding MSP2TEV (HisTev-H1-H2-H3-H4-H5-H6-H7-H8-H9-H10-GT-H1-H2-H3-H4-H5-H6-H7-H8-H9-H10) (SEQ ID NO:77)

atgggtcatcatcatcatcatcatcacgattatgatattcctactactga
gaatttgtattttcagggtctaaagctccttgacaactgggacagcgtga
cctccaccttcagcaagctgcgcgaacagctcggccctgtgacccaggag
ttctgggataacctggaaaaggagacagagggcctgaggcaggagatgag
caaggatctggaggaggtgaaggccaaggtgcagccctacctggacgact
tccagaagaagtggcaggaggagatggagctctaccgccagaaggtggag
ccgctgcgcgcagagctccaagagggcgcgcgccagaagctgcacgagct
gcaagagaagctgagcccactgggcgaggagatgcgcgaccgcgcgcg
ccatgtggacgcgctgcgcacgcatctggcccccctacagcgacgagctg
cgccagcgcctggccgcgcgcctggaggctctcaaggagaacggcggcgc
cagactggccgagtaccacgccaaggccaccgagcatctgagcacgctca
gcgagaaggccaagcccgcgctcgaggacctccgccaaggcctgctgccc
gtgctggagagcttcaaggtcagcttcctgagcgctctcgaggagtacac
taagaagctcaacacccaggtaccctaaagctccttgacaactgggaca
gcgtgacctccaccttcagcaagctgcgcgaacagctcggccctgtgacc
caggagttctgggataacctggaaaaggagacagagggcctgaggcagga
gatgagcaaggatctggaggaggtgaaggccaaggtgcagccctacctgg
acgacttccagaagaagtggcaggaggagatggagctctaccgccagaag
gtggagccgctgcgcgcagagctccaagagggcgcgcgccagaagctgca
cgagctgcaagagaagctgagcccactgggcgaggagatgcgcgaccgcg
cgcgcgccatgtggacgcgctgcgcacgcatctggcccccctacagcgac
gagctgcgccagcgcctggccgcgcgcctggaggctctcaaggagaacgg
cggcgccagactggccgagtaccacgccaaggccaccgagcatctgagca
cgctcagcgagaaggccaagcccgcgctcgaggacctccgccaaggcctg
ctgcccgtgctggagagcttcaaggtcagcttcctgagcgctctcgagga
gtacactaagaagctcaacacccag

TABLE 38

Amino acid sequence of HisTEV-MSP2 (SEQ ID NO:66)

MGHHHHHHHDYDIPTTENLYFQGLKLLDNWDSVTSTFSKLREQLGPVTQE
FWDNLEKETEGLRQEMSKDLEEVKAKVQPYLDDFQKKWQEEMELYRQKVE
PLRAELQEGARQKLHELQEKLSPLGEEMRDRARAHVDALRTHLAPYSDEL
RQRLAARLEALKENGGARLAEYHAKATEHLSTLSEKAKPALEDLRQGLLP
VLESFKVSFLSALEYTKKLNTQGTLKLLDNWDSVTSTFSKLREQLGPVTQ
EFWDNLEKETEGLRQEMSKDLEEVKAKVQPYLDDFQKKWQEEMELYRQKV
EPLRAELQEGARQKLHELQEKLSPLGEEMRDRARAHVDALRTHLAPYSDEL
RQRLAARLEALKENGGARLAEYHAKATEHLSTLSEKAKPALEDLRQGLLP
VLESFKVSFLSALEEYTKKLNTQ

New constructs have been designed to produce a "linear dimer" to generate Nanodiscs with only a single polypeptide sequence. These are fusions that make use of our knowledge of the parts of the MSP1 sequences which are important and are thus are "MSP2 derivatives". All have the TEV protease-cleavage His-tag.

TABLE 39

DNA sequence encoding MSP2N1 (HisTev-H0.5-H2-H3-H4-H5-H6-H7-H8-H9-H10-GT-H1/2-H2-H3-H4-H5-H6-H7-H8-H9-H10) (SEQ ID NO:78)

atgggtcatcatcatcatcatcatcacgattatgatattcctactactga
gaatttgtattttcagggttctaccttcagtaaacttcgcgaacaactgg
gccccgtgacgcaggaattctgggacaacctggaaaaagaaaccgaggga
ctgcgtcaggaaatgtccaaagatttagaagaggtgaaggccaaggttca
gccatatctcgatgactttcagaaaaaatggcaggaagagatggaattat
atcgtcaaaaggtggaaccgctgcgtgcggaactgcaagaggggcacgc
caaaaactccatgagctccaagagaagctcagcccattaggcgaagaaat
gcgcgatcgcgcccgtgcacatgttgatgcactccggactcatttggcgc
cgtattcggatgaacttcgccagcgtttggccgcacgtctcgaggcgctg
aaagaaaacggggtgcccgcttggctgagtaccacgcgaaagcgacaga
acacctgagcaccttgagcgaaaaagcgaaaccggcgctggaagatctac
gccagggcttattgcctgttcttgagagctttaaagtcagttttctgtca
gctctggaagaatatactaaaaagctgaatacccagggtaccttcagtaa
acttcgcgaacaactgggccccgtgacgcaggaattctgggacaacctgg
aaaaagaaaccgagggactgcgtcaggaaatgtccaaagattagaaagag
gtgaaggccaaggttcagccatatctcgatgactttcagaaaaaatggca
ggaagagatggaattatatcgtcaaaaggtggaaccgctgcgtgcggaac
tgcaagaggggcacgccaaaaactccatgagctccaagagaagctcagc
ccattaggcgaagaaatgcgcgatcgcgcccgtgcacatgttgatgcact
ccggactcatttggcgccgtattcggatgaacttcgccagcgtttggcgc
cacgtctcgaggcgctgaaagaaaacggggtgcccgcttggctgagtac
cacgcgaaagcgacagaacacctgagcaccttgagcgaaaaagcgaaacc
ggcgctggaagatctacgccagggcttattgcctgttcttgagagcttta
aagtcagttttctgtcagctctggaagaatatactaaaaagctgaatacc
cag

TABLE 40

Amino acid sequence of MSP2N1 (SEQ ID NO:68)

MGHHHHHHHDYDIPTTENLYFQGSTFSKLREQLGPVTQEFWDNLEKETEG
LRQEMSKDLEEVKAKVQPYLDDFQKKWQEEMELYRQKVEPLRAELQEGAR
QKLHELQEKLSPLGEEMRDRARAHVDALRTHLAPYSDELRQRLAARLEAL
KENGGARLAEYHAKATEHLSTLSEKAKPALEDLRQGLLPVLESFKVSFLS
ALEEYTKKLNTQGTFSKLREQLGPVTQEFWDNLEKETEGLRQEMSKDLEE
VKAKVQPYLDDFQKKWQEEMELYRQKVEPLRAELQEGARQKLHELQEKLS
PLGEEMRDRARAHVDALRTHLAPYSDELRQRLAARLEALKENGGARLAEY
HAKATEHLSTLSEKAKPALEDLRQGLLPVLESFKVSFLSALEEYTKKLNT
Q

TABLE 41

DNA sequence encoding MSP2N2 (SEQ ID NO:79)
(HisTev-H0.5-H2-H3-H4-H5-H6-H7-H8-H9-H10-GT-H2-H3-H4-H5-H6-H7-H8-H9-H10)

atgggtcatcatcatcatcatcatcacgattatgatattcctactactga
gaatttgtattttcagggttctaccttcagtaaacttcgcgaacaactgg
gccccgtgacgcaggaattctgggacaacctggaaaaagaaaccgaggga
ctgcgtcaggaaatgtccaaagatttagaagaggtgaaggccaaggttca
gccatatctcgatgactttcagaaaaaatggcaggaagagatggaattat
atcgtcaaaaggtggaaccgctgcgtgcggaactgcaagaggggcacgc
caaaaactccatgagctccaagagaagctcagcccattaggcgaagaaat
gcgcgatcgcgcccgtgcacatgttgatgcactccggactcatttggcgc
cgtattcggatgaacttcgccagcgtttggccgcacgtctcgaggcgctg
aaagaaaacggggtgcccgcttggctgagtaccacgcgaaagcgacaga
acacctgagcaccttgagcgaaaaagcgaaaccggcgctggaagatctac
gccagggcttattgcctgttcttgagagctttaaagtcagttttctgtca
gctctggaagaatatactaaaaagctgaatacccagggtaccccgcgtgac
gcaggaattctgggacaacctggaaaaagaaaccgagggactcgtcagg
aaatgtccaaagatttagaagaggtgaaggccaaggttcagccatatctc
gatgactttcagaaaaaatggcaggaagagatggaattatatcgtcaaaa
ggtggaaccgctgcgtgcggaactgcaagaggggcacgccaaaaactcc

TABLE 41-continued

DNA sequence encoding MSP2N2 (SEQ ID NO:79)
(HisTev-H0.5-H2-H3-H4-H5-H6-H7-H8-H9-H10-GT-H2-H3-H4-H5-H6-H7-H8-H9-H10)

atgagctccaagagaagctcagcccattaggcgaagaaatgcgcgatcgc
gcccgtgcacatgttgatgcactccggactcatttggcgccgtattcgga
tgaacttcgccagcgtttggccgcacgtctcgaggcgctgaaagaaaacg
ggggtgcccgcttggctgagtaccacgcgaaagcgacagaacacctgagc
accttgagcgaaaaagcgaaaccggcgctggaagatctacgccagggctt
attgcctgttcttgagagctttaaagtcagttttctgtcagctctggaag
aatatactaaaaagctgaatacccag

TABLE 42

Amino acid sequence of MSP2N2 (SEQ ID NO:69)

MGHHHHHHHDYDIPTTENLYFQGSTFSKLREQLGPVTQEFWDNLEKETEG
LRQEMSKDLEEVKAKVQPYLDDFQKKWQEEMELYRQKVEPLRAELQEGAR
QKLHELQEKLSPLGEEMRDRARAHVDALRTHLAPYSDELRQRLAARLEAL
KENGGARLAEYHAKATEHLSTLSEKAKPALEDLRQGLLPVLESFKVSFLS
ALEEYTKKLNTQGTPVTQEFWDNLEKETEGLRQEMSKDLEEVKAKVQPYL
DDFQKKWQEEMELYRQKVEPLRAELQEGARQKLHELQEKLSPLGEEMRDR
ARAHVDALRTHLAPYSDELRQRLAARLEALKENGGARLAEYHAKATEHLS
TLSEKAKPALEDLRQGLLPVLESFKVSFLSALEEYTKKLNTQ

A further MSP2 derivative (MSP2N3) has been designed to include helices 2-10 following the linker part of the H1 helix sequence. The DNA coding and amino acid sequences are given in Tables 43 and 44, respectively.

TABLE 43

DNA sequence encoding MSP2N3 (HisTev-H0.5-H2-H3-H4-H5-H6-H7-H8-H9-H10-GTREQLG-H2-H3-H4-H5-H6-H7-H8-H9-H10) (SEQ ID NO:80)

Atgggtcatcatcatcatcatcatcacgattatgatattcctactactga
gaatttgtattttcagggttctaccttcagtaaacttcgcgaacaactgg
gccccgtgacgcaggaattctgggacaacctggaaaaagaaaccgaggga
ctgcgtcaggaaatgtccaaagatttagaagaggtgaaggccaaggttca
gccatatctcgatgactttcagaaaaaatggcaggaagagatggaattat
atcgtcaaaaggtggaaccgctgcgtgcggaactgcaagaggggcacgc
caaaaactccatgagctccaagagaagctcagcccattaggcgaagaaat
gcgcgatcgcgcccgtgcacatgttgatgcactccggactcatttggcgc
cgtattcggatgaacttcgccagcgtttggccgcacgtctcgaggcgctg
aaagaaaacggggtgcccgcttggctgagtaccacgcgaaagcgacaga
acacctgagcaccttgagcgaaaaagcgaaaccggcgctggaagatctac
gccagggcttattgcctgttcttgagagctttaaagtcagttttctgtca
gctctggaagaatatactaaaaagctgaatacccagggtacccgcgaaca
actgggccccgtgacgcaggaattctgggacaacctggaaaaagaaaccg
agggactgcgtcaggaaatgtccaaagatttagaagaggtgaaggccaag
gttcagccatatctcgatgactttcagaaaaaatggcaggaagagatgga
attatatcgtcaaaaggtggaaccgctgcgtgcggaactgcaagaggggg
cacgccaaaaactccatgagctccaagagaagctcagcccattaggcgaa
gaaatgcgcgatcgcgcccgtgcacatgttgatgcactccggactcattt
ggcgccgtattcggatgaacttcgccagcgtttggccgcacgtctcgagg
cgctgaaagaaaacggggtgcccgcttggctgagtaccacgcgaaagcg
acagaacacctgagcaccttgagcgaaaaagcgaaaccggcgctggaaga
tctacgccagggcttattgcctgttcttgagagctttaaagtcagtttc
tgtcagctctggaagaatatactaaaaagctgaatacccagtaagctt

TABLE 44

Amino acid sequence of MSP2N3 (SEQ ID NO:81)

MGHHHHHHHDYDIPTTENLYFQGSTFSKLREQLGPVTQEFWDNLEKETEG
LRQEMSKDLEEVKAKVQPYLDDFQKKWQEEMELYRQKVEPLRAELQEGAR
QKLHELQEKLSPLGEEMRDRARAHVDALRTHLAPYSDELRQRLAARLEAL
KENGGARLAEYHAKATEHLSTLSEKAKPALEDLRQGLLPVLESFKVSFLS
ALEEYTKKLNTQGTREQLGPVTQEFWDNLEKETEGLRQEMSKDLEEVKAK

TABLE 44-continued

Amino acid sequence of MSP2N3 (SEQ ID NO:81)

VQPYLDDFQKKWQEEMELYRQKVEPLRAELQEGARQKLHELQEKLSPLGE
EMRDRARAHVDALRTHLAPYSDELRQRLAARLEALKENGGARLAEYHAKA
TEHLSTLSEKAKPALEDLRQGLLPVLESFKVSFLSALEEYTKKLNTQ

Unlike MSP2 and MSP2TEV these proteins self-assemble with lipids at 300:1 to 400:1 molar ratios with preferable formation of significantly bigger particles (Stokes diameter approximately 15.5 nm, corresponding to a calculated diameter assuming discoidal shape of about 17 nm).

Additional dimer sequences (i.e., tandem repeat MSP) have been designed with the fusion region to be composed of two different linkers which have high propensity to form beta-turns (Creighton, Proteins, p. 226). These scaffold proteins are specifically designed to promote the anti-parallel helix-turn-helix structure in Nanodiscs. The constituent scaffold proteins include MSP1T3, as well as the specially designed new scaffold proteins as described herein, MSP1N1 and the circularly permuted MSP2N5 which has a modified sequence of amphipathic helices to optimize the salt bridges formed between two scaffold proteins in the antiparallel helix-turn-helix structure.

The general scheme for a tandem repeat MSP is MSP-Linker-MSP, where linker may be either the Linker 1 or Linker 2 sequence defined below and MSP may be any of the monomeric membrane scaffold proteins previously defined. Linker 1 (Lb1) is composed of 4 amino acids, preferably the sequence Asn-Pro-Gly-Thr (SEQ ID NO:96). Linker 2 (Lb2) is composed of 6 amino acids with one additional residue on both ends to provide more flexibility, preferably the sequence Ser-Asn-Pro-Gly-Thr-Gln (SEQ ID NO:94).

TABLE 45

DNA sequence encoding MSP2N4 (His-TEV-H2S-H3-H4-
H5-H6-H7-H8-H9-H10-NPGT-H2-H3-H4-H5-H6-H7-H8-H9-
H10) (SEQ ID NO:82)

atgggtcatcatcatcatcatcatcacgattatgatattcctactactga
gaatttgtattttcagggttccgtgacgcaggaattctgggacaacctgg
aaaaagaaaccgagggactgcgtcaggaaatgtccaaagatttagaagag
gtgaaggccaaggttcagccatatctcgatgactttcagaaaaaatggca
ggaagagatggaattatatcgtcaaaaggtggaaccgctgcgtgcggaac
tgcaagaggggcacgccaaaaactccatgagctccaagagaagctcagc
ccattaggcgaagaaatgcgcgatcgcgcccgtgcacatgttgatgcact
ccggactcatttggcgccgtattcggatgaacttcgccagcgtttggccg
cacgtctcgaggcgctgaaagaaacgggggtgcccgcttggctgagtac
cacgcgaaagcgacagaacacctgagcacctttgagcgaaaaagcgaaacc
ggcgctggaagatctacgccagggcttattgcctgttcttgagagcttta
aagtcagttttctgtcagctctggaagaatatactaaaaagctgaatacc
cagaatccaggtaccccgtgacgcaggaattctgggacaacctggaaaa
agaaaccgagggactgcgtcaggaaatgtccaaagatttagaagaggtga
aggccaaggttcagccatatctcgatgactttcagaaaaaatggcaggaa
gagatggaattatatcgtcaaaaggtggaaccgctgcgtgcggaactgca
agaggggcacgccaaaaactccatgagctccaagagaagctcagcccat
taggcgaagaaatgcgcgatcgcgcccgtgcacatgttgatgcactccgg
actcatttggcgccgtattcggatgaacttcgccagcgtttggccg
cacgtctcgaggcgctgaaagaaacgggggtgcccgcttggctgagtaccacg
cgaaagcgacagaacacctgagcacctttgagcgaaaaagcgaaaccggcg
ctggaagatctacgccagggcttattgcctgttcttgagagctttaaagt
cagttttctgtcagctctggaagaatatactaaaaagctgaataccccag

TABLE 46

Amino acid sequence of MSP2N4 (SEQ ID NO:83)

MGHHHHHHHDYDIPTTENLYFQGSVTQEFWDNLEKETEGLRQEMSKDLEE
VKAKVQPYLDDFQKKWQEEMELYRQKVEPLRAELQEGARQKLHELQEKLS

TABLE 46-continued

Amino acid sequence of MSP2N4 (SEQ ID NO:83)

PLGEEMRDRARAHVDALRTHLAPYSDELRQRLAARLEALKENGGARLAEY
HAKATEHLSTLSEKAKPALEDLRQGLLPVLESFKVSFLSALEEYTKKLNT
QNPGTPVTQEFWDNLEKETEGLRQEMSKDLEEVKAKVQPYLDDFQKKWQE
EMELYRQKVEPLRAELQEGARQKLHELQEKLSPLGEEMRDRARAHVDALR
THLAPYSDELRQRLAARLEALKENGGARLAEYHAKATEHLSTLSEKAKPA
LEDLRQGLLPVLESFKVSFLSALEEYTKKLNTQ

TABLE 47

DNA sequence encoding MSP2N5 (His-TEV-H2S-H3-H4-
H4-H5-H6-H7-H8-H9-NPGT-H3-H4-H4-H5-H6-H7-H8-H9-
H2) (SEQ ID NO:84)

atgggtcatcatcatcatcatcatcacgattatgatattcctactactga
gaatttgtattttcagggttccgtgacgcaggaattctgggacaacctgg
aaaaagaaaccgagggactgcgtcaggaaatgtccaaagatttagaagag
gtgaaggccaaggttcagccatatctcgatgactttcagaaaaaatggca
ggaagagatggaattatatcgtcaaaaggtggaaccatatctcgatgact
ttcagaaaaaatggcaggaagagatggaattatatcgtcaaaaggtggaa
ccgctgcgtgcggaactgcaagaggggcacgccaaaaactccatgagct
ccaagagaagctcagcccattaggcgaagaaatgcgcgatcgcgcccgtg
cacatgttgatgcactccggactcatttggcgccgtattcggatgaactt
cgccagcgtttggccgcacgtctcgaggcgctgaaagaaacgggggtgc
ccgcttggctgagtaccacgcgaaagcgacagaacacctgagcaccttga
gcgaaaaagcgaaaccggcgctggaagatctacgccagggcttattgaat
ccaggtaccaaagattagaagaggtgaaggccaaggttcagccatatct
cgatgactttcagaaaaaatggcaggaagagatggaattatatcgtcaaa
aggtggaaccatatctcgatgactttcagaaaaaatggcaggaagagatg
gaattatatcgtcaaaaggtggaaccgctgcgtgcggaactgcaagaggg
ggcacgccaaaaactccatgagctccaagagaagctcagcccattaggcg
aagaaatgcgcgatcgcgcccgtgcacatgttgatgcactccggactcat
ttggcgccgtattcggatgaacttcgccagcgtttggccgcacgtctcga
ggcgctgaaagaaacgggggtgcccgcttggctgagtaccacgcgaaag
cgacagaacacctgagcaccttgagcgaaaaagcgaaaccggcgctggaa
gatctacgcagggcttattgcccgtgacgcaggaattctgggacaacctg
gaaaaagaaaccgagggactgcgtcaggaaatgtcc

TABLE 48

Amino acid sequence of MSP2N5 (SEQ ID NO:85)

MGHHHHHHHDYDIPTTENLYFQGSVTQEFWDNLEKETEGLRQEMSKDLEE
VKAKVQPYLDDFQKKWQEEMELYRQKVEPYLDDFQKKWQEEMELYRQKVE
PLRAELQEGARQKLHELQEKLSPLGEEMRDRARAHVDALRTHLAPYSDEL
RQRLAARLEALKENGGARLAEYHAKATEHLSTLSEKAKPALEDLRQGLLN
PGTKDLEEVKAKVQPYLDDFQKKWQEEMELYRQKVEPYLDDFQKKWQEEM
ELYRQKVEPLRAELQEGARQKLHELQEKLSPLGEEMRDRARAHVDALRTH
LAPYSDELRQRLAARLEALKENGGARLAEYHAKATEHLSTLSEKAKPALE
DLRQGLLPVTQEFWDNLEKETEGLRQEMS

TABLE 49

DNA sequence encoding MSP2N6 (His-TEV-H2S-H3-H4-
H4-H5-H6-H7-H8-H9-SNPGTQ-H3-H4-H4-H5-H6-H7-H8-
H9-H2) (SEQ ID NO:86)

atgggtcatcatcatcatcatcatcacgattatgatattcctactactga
gaatttgtattttcagggttccgtgacgcaggaattctgggacaacctgg
aaaaagaaaccgagggactgcgtcaggaaatgtccaaagatttagaagag
gtgaaggccaaggttcagccatatctcgatgactttcagaaaaaatggca
ggaagagatggaattatatcgtcaaaaggtggaaccatatctcgatgact
ttcagaaaaaatggcaggaagagatggaattatatcgtcaaaaggtggaa
ccgctgcgtgcggaactgcaagaggggcacgccaaaaactccatgagct
ccaagagaagctcagcccattaggcgaagaaatgcgcgatcgcgcccgtg
cacatgttgatgcactccggactcatttggcgccgtattcggatgaactt
cgccagcgtttggccgcacgtctcgaggcgctgaaagaaacgggggtgc
ccgcttggctgagtaccacgcgaaagcgacagaacacctgagcaccttga
gcgaaaaagcgaaaccggcgctggaagatctacgccagggcttattgtcc
aatccaggtaccaaaaagatttagaagaggtgaaggccaaggttcagcc

TABLE 49-continued

DNA sequence encoding MSP2N6 (His-TEV-H2S-H3-H4-H4-H5-H6-H7-H8-H9-SNPGTQ-H3-H4-H4-H5-H6-H7-H8-H9-H2) (SEQ ID NO:86)

```
atatctcgatgactttcagaaaaaatggcaggaagagatggaattatatc
gtcaaaaggtggaaccatatctcgatgactttcagaaaaaatggcaggaa
gagatggaattatatcgtcaaaaggtggaaccgctgcgtgcggaactgca
agaggggcacgccaaaaactccatgagctccaagagaagctcagcccat
taggcgaagaaatgcgcgatcgcgcccgtgcacatgttgatgcactccgg
actcatttggcgccgtattcggatgaacttcgccagcgtttggccgcacg
tctcgaggcgctgaaagaaaacgggggtgcccgcttggctgagtaccacg
cgaaagcgacagaacacctgagcaccttgagcgaaaaagcgaaaccggcg
ctggaagatctacgccagggcttattgcccgtgacgcaggaattctggga
caacctggaaaaagaaaccgagggactgcgtcaggaaatgtcc
```

TABLE 50

Amino acid sequence MSP2N6 (SEQ ID NO:87)

MGHHHHHHHDYDIPTTENLYFQGSVTQEFWDNLEKETEGLRQEMSKDLEE
VKAKVQPYLDDFQKKWQEEMELYRQKVEPYLDDFQKKWQEEMELYRQKVE
PLRAELQEGARQKLHELQEKLSPLGEEMRDRARAHVDALRTHLAPYSDEL
RQRLAARLEALKENGGARLAEYHAKATEHLSTLSEKAKPALEDLRQGLLS
NPGTQKDLEEVKAKVQPYLDDFQKKWQEEMELYRQKVEPYLDDFQKKWQE
EMELYRQKVEPLRAELQEGARQKLHELQEKLSPLGEEMRDRARAHVDALR
THLAPYSDELRQRLAARLEALKENGGARLAEYHAKATEHLSTLSEKAKPA
LEDLRQGLLPVTQEFWDNLEKETEGLRQEMS

MSP derivatives have been prepared with the incorporation of cysteine residues into the scaffold proteins by point mutation. DNA coding and amino acid sequences are given in Tables 51 and 52, respectively. In MSP1RC12' a cysteine residue is incorporated at the last residue in the Factor X recognition site. This mutant is used to prepare fluorescently labeled discs and attach to surfaces or matrices, for example, using heterofunctional cross linker molecules. In MSP1K90C, Lysine90 is replaced by a cysteine. See Tables 53 and 54 for coding and amino acid sequences respectively. In MSP1K152C, Lysine 152 is replaced by cysteine; see Tables 55 and 56.

TABLE 51

DNA sequence encoding MSP1RC12' (SEQ ID NO:88)

```
Atgggtcatcatcatcatcatcacattgagggatgtctgaagctgttgga
caattgggactctgttacgtctaccttcagtaaacttcgcgaacaactgg
gccccgtgacgcaggaattctgggacaacctggaaaaagaaaccgaggga
ctgcgtcaggaaatgtccaaagatttagaagaggtgaaggccaaggttca
gccatatctcgatgactttcagaaaaaatggcaggaagagatggaattat
atcgtcaaaaggtggaaccgctgcgtgcggaactgcaagaggggcacgc
caaaaactccatgagctccaagagaagctcagcccattaggcgaagaaat
gcgcgatcgcgcccgtgcacatgttgatgcactccggactcatttggcgc
cgtattcggatgaacttcgccagcgtttggccgcacgtctcgaggcgctg
aaagaaaacgggggtgcccgcttggctgagtaccacgcgaaagcgacaga
acacctgagcaccttgagcgaaaaagcgaaaccggcgctggaagatctac
gccagggcttattgcctgttcttgagagctttaaagtcagttttctgtca
gctctggaagaatatactaaaaagctgaatacccag
```

TABLE 52

MSP1RC12' Protein Sequence (SEQ ID NO:89)

MGHHHHHHIEGCLKLLLDNWDSVTSTFSKLREQLGPVTQEFWDNLEKETEG
LRQEMSKDLEEVKAKVQPYLDDFQKKWQEEMELYRQKVEPLRAELQEGAR
QKLHELQEKLSPLGEEMRDRARAHVDALRTHLAPYSDELRQRLAARLEAL
KENGGARLAEYHAKATEHLSTLSEKAKPALEDLRQGLLPVLESFKVSFLS
ALEEYTKKLNTQ

TABLE 53

DNA sequence encoding MSP1K90C (SEQ ID NO:90)

```
atgggtcatcatcatcatcatcacattgagggacgtctgaagctgttgga
caattgggactctgttacgtctaccttcagtaaacttcgcgaacaactgg
gccccgtgacgcaggaattctgggacaacctggaaaaagaaaccgaggga
ctgcgtcaggaaatgtccaaagatttagaagaggtgaaggccaaggttca
gccatatctcgatgactttcagaaaaaatggcaggaagagatggaattat
atcgtcaaaaggtggaaccgctgcgtgcggaactgcaagaggggcacgc
caatgtctccatgagctccaagagaagctcagcccattaggcgaagaaat
gcgcgatcgcgcccgtgcacatgttgatgcactccggactcatttggcgc
cgtattcggatgaacttcgccagcgtttggccgcacgtctcgaggcgctg
aaagaaaacgggggtgcccgcttggctgagtaccacgcgaaagcgacaga
acacctgagcaccttgagcgaaaaagcgaaaccggcgctggaagatctac
gccagggcttattgctgttcttgagagctttaaagtcagttttctgtca
gctctggaagaatatactaaaaagctgaatacccag
```

TABLE 54

MSP1K90C Protein sequence (SEQ ID NO:91)

MGHHHHHHIEGRLKLLLDNWDSVTSTFSKLREQLGPVTQEFWDNLEKETEG
LRQEMSKDLEEVKAKVQPYLDDFQKKWQEEMELYRQKVEPLRAELQEGAR
QCLHELQEKLSPLGEEMRDRARAHVDALRTHLAPYSDELRQRLAARLEAL
KENGGARLAEYHAKATEHLSTLSEKAKPALEDLRQGLLPVLESFKVSFLS
ALEEYTKKLNTQ

TABLE 55

DNA sequence encoding MSP1K152C (SEQ ID NO:92)

```
atgggtcatcatcatcatcatcacattgagggacgtctgaagctgttgga
caattgggactctgttacgtctaccttcagtaaacttcgcgaacaactgg
gccccgtgacgcaggaattctgggacaacctggaaaaagaaaccgaggga
ctgcgtcaggaaatgtccaaagatttagaagaggtgaaggccaaggttca
gccatatctcgatgactttcagaaaaaatggcaggaagagatggaattat
atcgtcaaaaggtggaaccgctgcgtgcggaactgcaagaggggcacgc
caaaaactccatgagctccaagagaagctcagcccattaggcgaagaaat
gcgcgatcgcgcccgtgcacatgttgatgcactccggactcatttggcgc
cgtattcggatgaacttcgccagcgtttggccgcacgtctcgaggcgctg
aaagaaaacgggggtgcccgcttggctgagtaccacgcatgcgcgacaga
acacctgagcaccttgagcgaaaaagcgaaaccggcgctggaagatctac
gccagggcttattgctgttcttgagagctttaaagtcagttttctgtca
gctctggaagaatatactaaaaagctgaatacccag
```

TABLE 56

MSP1K152C Protein sequence (SEQ ID NO:93)

MGHHHHHHIEGRLKLLLDNWDSVTSTFSKLREQLGPVTQEFWDNLEKETEG
LRQEMSKDLEEVKAKVQPYLDDFQKKWQEEMELYRQKVEPLRAELQEGAR
QKLHELQEKLSPLGEEMRDRARAHVDALRTHLAPYSDELRQRLAARLEAL
KENGGARLAEYHACATEHLSTLSEKAKPALEDLRQGLLPVLESFKVSFLS
ALEEYTKKLNTQ

The mutations in MSP1K90 C and in MSP1K152C are located on inter-helical interfaces. Discs were formed in the presence of DTT. The discs are more stable toward temperature-induced irreversible degradation. These are variants of the "Milano" mutations.

In addition to these sequences, there are two fusion protein constructs of reference. These are composed of two MSP1 constructs linked by a Gly-Ser linker: MSP2 (MSP1-Gly-Thr-MSP1, SEQ ID NO:8) and MSP2D1D1 (MSP1T3-Gly-Thr-H2-H3-H4-H5-H6-H7-H8-H9-H10, SEQ ID NO:70).

Other constructs that can be readily produced include permutations of the above, i.e. MSP1 or MSP2 or MSP2a with any combination of the following: hinge deletion, hinge replacement, half-repeat deletion, histidine tag, different linkers for MSP2 analogs.

To express MSP proteins, the nucleic acid constructs were inserted between the NcoI and HindIII sites in the pET28 expression vector and transformed into *E. coli* BL21(DE3).

Transformants were grown on LB plates using kanamycin for selection. Colonies were used to inoculate 5 ml starter cultures grown in LB broth containing 30 µg/ml kanamycin. For overexpression, cultures were inoculated by adding 1 volume overnight culture to 100 volumes LB broth containing 30 µg/ml kanamycin and grown in shaker flasks at 37° C. When the optical density at 600 nm reached 0.6-0.8, isopropyl-β-D-thiogalactopyranoside (IPTG) was added to a concentration of 1 mM to induce expression and cells were grown 3-4 hours longer before harvesting by centrifugation. Cell pellets were flash frozen and stored at −80° C.

Purification of histidine-tagged MSPs was carried out as follows. A frozen cell pellet from 1 liter of expression culture was resuspended in 25 milliliters of 20 mM Tris HCl pH 7.5 containing 1 mM phenylmethylsulfonyl fluoride. Triton X-100 (t-octylphenoxypolyethoxyethanol) was added from a 10% (w/v) stock in distilled H2O to a final concentration of 1%. The resuspended cells were sonicated on ice at 50% duty cycle at a power setting of 5 for four cycles of 1 minute on, 5 minutes off with a Branson probe sonifier. The resulting lysate was centrifuged for 30 minutes at 30,000 rpm in a Beckman Ti 45 rotor in an ultracentrifuge. The resulting supernatant was filtered through a 0.22 µm nylon syringe filter. The salt concentration was adjusted to 0.5 M from a 4 M NaCl stock in water and applied to a 5 ml Hi-Trap nickel loaded column (Pharmacia, Piscataway, N.J.).

For His-tagged-MSP1, the column is washed with 20 ml buffer (10 mM Tris pH 8, 0.5 M NaCl) containing 1% Triton X-100, followed by 20 ml buffer+50 mM sodium cholate, and then 20 ml buffer and 20 ml 100 mM imidazole in buffer. The His-tagged polypeptide is eluted with 15 ml 0.5 M imidazole in buffer.

For His-tagged-MSP2, the column is washed with 20 ml buffer (10 mM Tris pH 8, 0.5 M NaCl) containing 1% Triton X-100; 20 ml buffer+50 mM cholate; 20 ml buffer; 20 ml 35 mM imidazole in buffer. The His-tagged polypeptide is then eluted with 15 ml 0.5 M imidazole in buffer, and the purified protein is dialyzed against 10 mM Tris pH 8, 0.15 M NaCl using a 10,000 MW cutoff cellulose dialysis membrane.

The amino acid sequence of the recombinant TF is given in Table 57; see also SEQ ID NO:95. The mature rTF lacks the 22 N-terminal amino acids. The HPC4 epitope which allows immunoaffinity purification is at amino acids 23-35. The TF extracellular domain is amino acids 36-254; the transmembrane domain which inserts into the phospholipid bilayer of the disc-like nanoscale particles occurs at amino acids 255-277; and amino acids 278-279 are the remnants of the cytoplasmic domain (most of which has been deleted. Expression of this rTF is carried out as described in Rezaie et al. 1992. Protein Expr. Purif. 3:453-460, 1992 and Smith S A and Morrissey J. H. 2004. J. Thromb. Haemost. 2:1610-1616. In general, although TF may not be specified as rTF, TF incorporated into nanoscale disc-like particles is the truncated rTF.

All references cited herein are hereby incorporated by reference to the extent there is no inconsistency with the present disclosure; and the references cited herein reflect the level of skill in the relevant arts.

In general the terms and phrases used herein have their art-recognized meaning, which can be found by reference to standard texts, journal references and contexts known to those skilled in the art.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations not specifically disclosed herein.

The exact formulation, route of administration and dosage can be chosen by the individual physician in view of the patient's condition (see e.g. Fingl et al., in The Pharmacological Basis of Therapeutics, 1975, Ch. 1 p. 1).

It should be noted that the attending physician would know how to and when to terminate, interrupt, or adjust administration due to toxicity, or to organ dysfunctions, or to other adverse effects. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and dose frequency may also vary according to the age, body weight, and response of the individual patient. A program comparable to that discussed above also may be used in veterinary medicine.

Depending on the specific conditions being treated and the targeting method selected, such agents may be formulated and administered systemically or locally. Techniques for formulation and administration may be found in Alfonso and Gennaro (1995). Suitable routes may include, for example, oral, rectal, transdermal, vaginal, transmucosal, or intestinal administration; parenteral delivery, including intramuscular, subcutaneous, or intramedullary injections, as well as intrathecal, intravenous, or intraperitoneal injections.

TABLE 57

Amino Acid Sequence of rTF (see also SEQ ID NO:95)

```
  1 MKYLLPTAAA GLLLLAAQPA MAAEDQVDPR LIDGKSGTTN TVAAYNLTWK STNFKTILEW
 61 EPKPVNQVYT VQISTKSGDW KSKCFYTTDT ECDLTDEIVK DVKQTYLARV FSYPAGNVES
121 TGSAGEPLYE NSPEFTPYLE TNLGQPTIQS FEQVGTKVNV TVEDERTLVR RNNTFLSLRD
181 VFGKDLIYTL YYWKSSSSGK KTAKTNTNEF LIDVDKGENY CFSVQAVIPS RTVNRKSTDS
241 PVECMGQEKG EFREIFYIIG AVVFVVIILV IILAISLHK
```

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular those formulated as solutions, may be administered parenterally, such as by intravenous injection. Appropriate compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve the intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions, including those formulated for delayed release or only to be released when the pharmaceutical reaches the small or large intestine.

The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The terms and expressions which have been employed are used as terms of description and not of limitation, and there is no intention in the use of such terms and expressions to exclude any equivalents of the features shown and described or portions thereof, but it is recognized that various modifications are possible within the scope of the invention claimed. Thus, it should be understood that although the present invention has been specifically disclosed by particular embodiments and optional features, modification and variation of the concepts herein disclosed may be resorted to by those skilled in the art, and that such modifications and variations are considered to be within the scope of this invention as defined by the appended claims.

Although the description herein contains certain specific examples and information, these should not be construed as limiting the scope of the invention but rather as merely providing illustrations of some of the presently preferred embodiments of the invention. For example, thus the scope of the invention should be determined by the appended claims and their equivalents, rather than by the examples given.

SEQUENCE LISTING

<160> NUMBER OF SEQ ID NOS: 96

<210> SEQ ID NO 1
<211> LENGTH: 762
<212> TYPE: DNA
<213> ORGANISM: Homo sapiens

<400> SEQUENCE: 1

```
ccatggccca tttctggcag caagatgaac cccccagag ccctggggat cgagtgaagg      60
acctggccac tgtgtacgtg gatgtgctca agacagcgg cagagactat gtgtcccagt     120
ttgaaggctc cgccttggga aaacagctaa acctaaagct ccttgacaac tgggacagcg     180
tgacctccac cttcagcaag ctgcgcgaac agctcggccc tgtgacccag gagttctggg     240
ataacctgga aaaggagaca gagggcctga ggcaagagat gagcaaggat ctggaggagg     300
tgaaggccaa ggtgcagccc tacctggacg acttccagaa gaagtggcag gaggagatgg     360
agctctaccg ccagaaggtg gagccgctgc gcgcagagct ccaagagggc gcgcgccaga     420
agctgcacga gctgcaagag aagctgagcc cactgggcga ggagatgcgc gaccgcgcgc     480
gcgcccatgt ggacgcgctg cgcacgcatc tggcccccta cagcgacgag ctgcgccagc     540
gcttggccgc gcgccttgag gctctcaagg agaacggcgg cgccagactg gccgagtacc     600
acgccaaggc caccgagcat ctgagcacgc tcagcgagaa ggccaagccc gcgctcgagg     660
acctccgcca aggcctgctg cccgtgctgg agagcttcaa ggtcagcttc ctgagcgctc     720
tcgaggagta cactaagaag ctcaacaccc agtaataagc tt                        762
```

<210> SEQ ID NO 2
<211> LENGTH: 250
<212> TYPE: PRT
<213> ORGANISM: Homo sapiens

<400> SEQUENCE: 2

```
Met Ala His Phe Trp Gln Gln Asp Glu Pro Pro Gln Ser Pro Trp Asp
  1               5                  10                  15
Arg Val Lys Asp Leu Ala Thr Val Tyr Val Asp Val Leu Lys Asp Ser
             20                  25                  30
Gly Arg Asp Tyr Val Ser Gln Phe Glu Gly Ser Ala Leu Gly Lys Gln
         35                  40                  45
Leu Asn Leu Lys Leu Leu Asp Asn Trp Asp Ser Val Thr Ser Thr Phe
     50                  55                  60
Ser Lys Leu Arg Glu Gln Leu Gly Pro Val Thr Gln Glu Phe Trp Asp
 65                  70                  75                  80
Asn Leu Glu Lys Glu Thr Glu Gly Leu Arg Gln Glu Met Ser Lys Asp
                 85                  90                  95
Leu Glu Glu Val Lys Ala Lys Val Gln Pro Tyr Leu Asp Asp Phe Gln
            100                 105                 110
Lys Lys Trp Gln Glu Glu Met Glu Leu Tyr Arg Gln Lys Val Glu Pro
        115                 120                 125
Leu Arg Ala Glu Leu Gln Glu Gly Ala Arg Gln Lys Leu His Glu Leu
    130                 135                 140
Gln Glu Lys Leu Ser Pro Leu Gly Glu Glu Met Arg Asp Arg Ala Arg
145                 150                 155                 160
Ala His Val Asp Ala Leu Arg Thr His Leu Ala Pro Tyr Ser Asp Glu
                165                 170                 175
Leu Arg Gln Arg Leu Ala Ala Arg Leu Glu Ala Leu Lys Glu Asn Gly
            180                 185                 190
Gly Ala Arg Leu Ala Glu Tyr His Ala Lys Ala Thr Glu His Leu Ser
        195                 200                 205
Thr Leu Ser Glu Lys Ala Lys Pro Ala Leu Glu Asp Leu Arg Gln Gly
    210                 215                 220
Leu Leu Pro Val Leu Glu Ser Phe Lys Val Ser Phe Leu Ser Ala Leu
```

```
                        225                 230                 235                 240

Glu Glu Tyr Thr Lys Lys Leu Asn Thr Gln
                    245                 250

<210> SEQ ID NO 3
<211> LENGTH: 654
<212> TYPE: DNA
<213> ORGANISM: Artificial
<220> FEATURE:
<223> OTHER INFORMATION: Nucleotide sequence encoding MSP1

<400> SEQUENCE: 3
tataccatgg gccatcatca tcatcatcat atagaaggaa gactaaagct ccttgacaac      60
tgggacagcg tgacctccac cttcagcaag ctgcgcgaac agctcggccc tgtgacccag     120
gagttctggg ataacctgga aaaggagaca gagggcctga ggcaggagat gagcaaggat     180
ctggaggagt gaaggccaa ggtgcagccc tacctggacg acttccagaa gaagtggcag      240
gaggagatgg agctctaccg ccagaaggtg agccgctgc gcgcagagct ccaagagggc      300
gcgcgccaga gctgcacga gctgcaagag aagttgagcc cactgggcga ggagatgcgc     360
gaccgcgcgc gcgcccatgt ggacgcgctg cgcacgcatc tggcccccta cagcgacgag     420
ctgcgccagc gcttggccgc gcgccttgag gctctcaagg agaacggcgg cgccagactg     480
gccgagtacc acgccaaggc caccgagcat ctgagcacgc tcagcgagaa ggccaaaccc     540
gcgctcgagg acctccgcca aggcctgctg cccgtgctgg agagcttcaa ggtcagcttc     600
ctgagcgctc tcgaggagta cactaagaag ctcaacaccc agtaataagc ttgc           654

<210> SEQ ID NO 4
<211> LENGTH: 212
<212> TYPE: PRT
<213> ORGANISM: Artificial
<220> FEATURE:
<223> OTHER INFORMATION: MSP1

<400> SEQUENCE: 4

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175
```

```
Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln
    210
```

<210> SEQ ID NO 5
<211> LENGTH: 619
<212> TYPE: DNA
<213> ORGANISM: Artificial
<220> FEATURE:
<223> OTHER INFORMATION: Nucleotide sequence encoding MSP1 without His tag

<400> SEQUENCE: 5

```
taccatggca aagctccttg acaactggga cagcgtgacc tccaccttca gcaagctgcg     60
cgaacagctc ggccctgtga cccaggagtt ctgggataac ctggaaaagg agacagaggg    120
cctgaggcag agatgagca aggatctgga ggaggtgaag gccaaggtgc agccctacct    180
ggacgacttc cagaagaagt ggcaggagga gatggagctc taccgccaga aggtggagcc    240
gctgcgcgca gagctccaag agggcgcgcg ccagaagctg cacgagctgc aagagaagtt    300
gagcccactg ggcgaggaga tgcgcgaccg cgcgcgcgcc catgtggacg cgctgcgcac    360
gcatctggcc ccctacagcg acgagctgcg ccagcgcttg gccgcgcgcc ttgaggctct    420
caaggagaac ggcggcgcca gactggccga gtaccacgcc aaggccaccg agcatctgag    480
cacgctcagc gagaaggcca aacccgcgct cgaggacctc cgccaaggcc tgctgcccgt    540
gctggagagc ttcaaggtca gcttcctgag cgctctcgag gagtacacta agaagctcaa    600
cacccagtaa taagcttgc                                                  619
```

<210> SEQ ID NO 6
<211> LENGTH: 201
<212> TYPE: PRT
<213> ORGANISM: Artificial
<220> FEATURE:
<223> OTHER INFORMATION: MSP1 without His tag

<400> SEQUENCE: 6

```
Met Ala Lys Leu Leu Asp Asn Trp Asp Ser Val Thr Ser Thr Phe Ser
1               5                   10                  15

Lys Leu Arg Glu Gln Leu Gly Pro Val Thr Gln Glu Phe Trp Asp Asn
            20                  25                  30

Leu Glu Lys Glu Thr Glu Gly Leu Arg Gln Glu Met Ser Lys Asp Leu
        35                  40                  45

Glu Glu Val Lys Ala Lys Val Gln Pro Tyr Leu Asp Asp Phe Gln Lys
    50                  55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140
```

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
            165                 170                 175

Leu Pro Val Leu Glu Ser Phe Lys Val Ser Phe Leu Ser Ala Leu Glu
        180                 185                 190

Glu Tyr Thr Lys Lys Leu Asn Thr Gln
        195                 200

<210> SEQ ID NO 7
<211> LENGTH: 1260
<212> TYPE: DNA
<213> ORGANISM: Artificial
<220> FEATURE:
<223> OTHER INFORMATION: Nucleotide sequence encoding MSP2 with short
      linker

<400> SEQUENCE: 7
tataccatgg gccatcatca tcatcatcat atagaaggaa gactaaagct ccttgacaac      60
tgggacagcg tgacctccac cttcagcaag ctgcgcgaac agctcggccc tgtgacccag     120
gagttctggg ataacctgga aaaggagaca gagggcctga ggcaggagat gagcaaggat     180
ctggaggagt gaaggccaa ggtgcagccc tacctggacg acttccagaa gaagtggcag      240
gaggagatgg agctctaccg ccagaaggtg agccgctgc gcgcagagct ccaagagggc      300
gcgcgccaga gctgcacga gctgcaagag aagctgagcc cactgggcga ggagatgcgc     360
gaccgcgcgc gcgcccatgt ggacgcgctg cgcacgcatc tggccccta cagcgacgag      420 ctgcgccagc gcttggccgc gcgccttgag gctctcaagg agaacggcgg cgccagactg     480
gccgagtacc acgccaaggc caccgagcat ctgagcacgc tcagcgagaa ggccaagccc     540
gcgctcgagg acctccgcca aggcctgctg cccgtgctgg agagcttcaa ggtcagcttc     600
ctgagcgctc tcgaggagta cactaagaag ctcaacaccc agggtaccct aaagctcctt     660
gacaactggg acagcgtgac ctccaccttc agcaagctgc gcgaacagct cggccctgtg     720
acccaggagt tctgggataa cctggaaaag gagacagagg gcctgaggca ggagatgagc     780
aaggatctgg aggaggtgaa ggccaaggtg cagccctacc tggacgactt ccagaagaag     840
tggcaggagg agatggagct ctaccgccag aaggtggagc cgctgcgcgc agagctccaa     900
gagggcgcgc gccagaagct gcacgagctg aagagaagc tgagcccact gggcgaggag      960
atgcgcgacc gcgcgcgcgc ccatgtggac gcgctgcgca cgcatctggc ccctacagc     1020 gacgagctgc gccagcgctt ggccgcgcgc cttgaggctc tcaaggagaa cggcggcgcc    1080
agactggccg agtaccacgc caaggccacc gagcatctga gcacgctcag cgagaaggcc    1140
aagcccgcgc tcgaggacct ccgccaaggc ctgctgcccg tgctggagag cttcaaggtc    1200
agcttcctga gcgctctcga ggagtacact aagaagctca cacccagta ataagcttgc    1260

<210> SEQ ID NO 8
<211> LENGTH: 414
<212> TYPE: PRT
<213> ORGANISM: Artificial
<220> FEATURE:
<223> OTHER INFORMATION: MSP2 with short linker

<400> SEQUENCE: 8

Met Gly His His His His His His Ile Glu Gly Arg Leu Lys Leu Leu
1               5                   10                  15

-continued

```
Asp Asn Trp Asp Ser Val Thr Ser Thr Phe Ser Lys Leu Arg Glu Gln
         20                  25                  30

Leu Gly Pro Val Thr Gln Glu Phe Trp Asp Asn Leu Glu Lys Glu Thr
         35                  40                  45

Glu Gly Leu Arg Gln Glu Met Ser Lys Asp Leu Glu Glu Val Lys Ala
 50                  55                  60

Lys Val Gln Pro Tyr Leu Asp Asp Phe Gln Lys Lys Trp Gln Glu Glu
 65                  70                  75                  80

Met Glu Leu Tyr Arg Gln Lys Val Glu Pro Leu Arg Ala Glu Leu Gln
                 85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln Gly Thr Leu Lys Leu Leu Asp Asn Trp Asp Ser Val
210                 215                 220

Thr Ser Thr Phe Ser Lys Leu Arg Glu Gln Leu Gly Pro Val Thr Gln
225                 230                 235                 240

Glu Phe Trp Asp Asn Leu Glu Lys Glu Thr Glu Gly Leu Arg Gln Glu
                245                 250                 255

Met Ser Lys Asp Leu Glu Glu Val Lys Ala Lys Val Gln Pro Tyr Leu
            260                 265                 270

Asp Asp Phe Gln Lys Lys Trp Gln Glu Glu Met Glu Leu Tyr Arg Gln
        275                 280                 285

Lys Val Glu Pro Leu Arg Ala Glu Leu Gln Glu Gly Ala Arg Gln Lys
290                 295                 300

Leu His Glu Leu Gln Glu Lys Leu Ser Pro Leu Gly Glu Glu Met Arg
305                 310                 315                 320

Asp Arg Ala Arg Ala His Val Asp Ala Leu Arg Thr His Leu Ala Pro
                325                 330                 335

Tyr Ser Asp Glu Leu Arg Gln Arg Leu Ala Ala Arg Leu Glu Ala Leu
            340                 345                 350

Lys Glu Asn Gly Gly Ala Arg Leu Ala Glu Tyr His Ala Lys Ala Thr
        355                 360                 365

Glu His Leu Ser Thr Leu Ser Glu Lys Ala Lys Pro Ala Leu Glu Asp
370                 375                 380

Leu Arg Gln Gly Leu Leu Pro Val Leu Glu Ser Phe Lys Val Ser Phe
385                 390                 395                 400

Leu Ser Ala Leu Glu Glu Tyr Thr Lys Lys Leu Asn Thr Gln
                405                 410
```

<210> SEQ ID NO 9
<211> LENGTH: 1282
<212> TYPE: DNA

<213> ORGANISM: Artificial
<220> FEATURE:
<223> OTHER INFORMATION: Nucleotide sequence encoding MSP2L (with long linker)

<400> SEQUENCE: 9

```
taccatgggc catcatcatc atcatcatat agaaggaaga ctaaagctcc ttgacaactg      60
ggacagcgtg acctccacct tcagcaagct gcgcgaacag ctcggccctg tgacccagga     120
gttctgggat aacctggaaa aggagacaga gggcctgagg caggagatga gcaaggatct     180
ggaggaggtg aaggccaagg tgcagcccta cctggacgac ttccagaaga agtggcagga     240
ggagatggag ctctaccgcc agaaggtgga gccgctgcgc gcagagctcc aagagggcgc     300
gcgccagaag ctgcacgagc tgcaagagaa gctgagccca ctgggcgagg agatgcgcga     360
ccgcgcgcgc gcccatgtgg acgcgctgcg cacgcatctg gcccctaca gcgacgagct     420
gcgccagcgc ttggccgcgc gccttgaggc tctcaaggag aacggcggcg ccagactggc     480
cgagtaccac gccaaggcca ccgagcatct gagcacgctc agcgagaagg ccaagcccgc     540
gctcgaggac ctccgccaag gcctgctgcc cgtgctggag agcttcaagg tcagcttcct     600
gagcgctctc gaggagtaca ctaagaagct caacacccag ggtaccggtg aggtagtgg      660
aggtggtacc ctaaagctcc ttgacaactg ggacagcgtg acctccacct tcagcaagct     720
gcgcgaacag ctcggccctg tgacccagga gttctgggat aacctggaaa aggagacaga     780
gggcctgagg caggagatga gcaaggatct ggaggaggtg aaggccaagg tgcagcccta     840
cctggacgac ttccagaaga agtggcagga ggagatggag ctctaccgcc agaaggtgga     900
gccgctgcgc gcagagctcc aagagggcgc gcgccagaag ctgcacgagc tgcaagagaa     960
gctgagccca ctgggcgagg agatgcgcga ccgcgcgcgc gcccatgtgg acgcgctgcg    1020
cacgcatctg gcccctaca gcgacgagct gcgccagcgc ttggccgcgc gccttgaggc    1080
tctcaaggag aacggcggcg ccagactggc cgagtaccac gccaaggcca ccgagcatct    1140
gagcacgctc agcgagaagg ccaagcccgc gctcgaggac ctccgccaag gcctgctgcc    1200
cgtgctggag agcttcaagg tcagcttcct gagcgctctc gaggagtaca ctaagaagct    1260
caacacccag taataagctt gc                                            1282
```

<210> SEQ ID NO 10
<211> LENGTH: 422
<212> TYPE: PRT
<213> ORGANISM: Artificial
<220> FEATURE:
<223> OTHER INFORMATION: MSP2L (with long linker)

<400> SEQUENCE: 10

```
Met Gly His His His His His His Ile Glu Gly Arg Leu Lys Leu Leu
1               5                   10                  15
Asp Asn Trp Asp Ser Val Thr Ser Thr Phe Ser Lys Leu Arg Glu Gln
            20                  25                  30
Leu Gly Pro Val Thr Gln Glu Phe Trp Asp Asn Leu Glu Lys Glu Thr
        35                  40                  45
Glu Gly Leu Arg Gln Glu Met Ser Lys Asp Leu Glu Glu Val Lys Ala
    50                  55                  60
Lys Val Gln Pro Tyr Leu Asp Asp Phe Gln Lys Lys Trp Gln Glu Glu
65                  70                  75                  80
Met Glu Leu Tyr Arg Gln Lys Val Glu Pro Leu Arg Ala Glu Leu Gln
                85                  90                  95
```

```
Glu Gly Ala Arg Gln Lys Leu His Glu Leu Gln Glu Lys Leu Ser Pro
                100                 105                 110
Leu Gly Glu Glu Met Arg Asp Arg Ala Arg Ala His Val Asp Ala Leu
            115                 120                 125
Arg Thr His Leu Ala Pro Tyr Ser Asp Glu Leu Arg Gln Arg Leu Ala
        130                 135                 140
Ala Arg Leu Glu Ala Leu Lys Glu Asn Gly Gly Ala Arg Leu Ala Glu
145                 150                 155                 160
Tyr His Ala Lys Ala Thr Glu His Leu Ser Thr Leu Ser Glu Lys Ala
                165                 170                 175
Lys Pro Ala Leu Glu Asp Leu Arg Gln Gly Leu Leu Pro Val Leu Glu
            180                 185                 190
Ser Phe Lys Val Ser Phe Leu Ser Ala Leu Glu Glu Tyr Thr Lys Lys
        195                 200                 205
Leu Asn Thr Gln Gly Thr Gly Gly Ser Gly Gly Gly Thr Leu Lys
    210                 215                 220
Leu Leu Asp Asn Trp Asp Ser Val Thr Ser Thr Phe Ser Lys Leu Arg
225                 230                 235                 240
Glu Gln Leu Gly Pro Val Thr Gln Glu Phe Trp Asp Asn Leu Glu Lys
                245                 250                 255
Glu Thr Glu Gly Leu Arg Gln Glu Met Ser Lys Asp Leu Glu Glu Val
            260                 265                 270
Lys Ala Lys Val Gln Pro Tyr Leu Asp Asp Phe Gln Lys Lys Trp Gln
        275                 280                 285
Glu Glu Met Glu Leu Tyr Arg Gln Lys Val Glu Pro Leu Arg Ala Glu
    290                 295                 300
Leu Gln Glu Gly Ala Arg Gln Lys Leu His Glu Leu Gln Glu Lys Leu
305                 310                 315                 320
Ser Pro Leu Gly Glu Glu Met Arg Asp Arg Ala Arg Ala His Val Asp
                325                 330                 335
Ala Leu Arg Thr His Leu Ala Pro Tyr Ser Asp Glu Leu Arg Gln Arg
            340                 345                 350
Leu Ala Ala Arg Leu Glu Ala Leu Lys Glu Asn Gly Gly Ala Arg Leu
        355                 360                 365
Ala Glu Tyr His Ala Lys Ala Thr Glu His Leu Ser Thr Leu Ser Glu
    370                 375                 380
Lys Ala Lys Pro Ala Leu Glu Asp Leu Arg Gln Gly Leu Leu Pro Val
385                 390                 395                 400
Leu Glu Ser Phe Lys Val Ser Phe Leu Ser Ala Leu Glu Glu Tyr Thr
                405                 410                 415
Lys Lys Leu Asn Thr Gln
            420

<210> SEQ ID NO 11
<211> LENGTH: 522
<212> TYPE: DNA
<213> ORGANISM: Artificial
<220> FEATURE:
<223> OTHER INFORMATION: Nucleotide sequence encoding MSP1D5D6

<400> SEQUENCE: 11
tataccatgg gccatcatca tcatcatcat atagaaggaa gactaaagct ccttgacaac      60
tgggacagcg tgacctccac cttcagcaag ctgcgcgaac agctcggccc tgtgacccag     120
gagttctggg ataacctgga aaaggagaca gagggcctga ggcaggagat gagcaaggat     180
```

```
ctggaggagg tgaaggccaa ggtgcagccc tacctggacg acttccagaa gaagtggcag    240
gaggagatgg agctctaccg ccagaaggtg gagccctaca gcgacgagct gcgccagcgc    300
ttggccgcgc gccttgaggc tctcaaggag aacggcggcg ccagactggc cgagtaccac    360
gccaaggcca ccgagcatct gagcacgctc agcgagaagg ccaaacccgc gctcgaggac    420
ctccgccaag gcctgctgcc cgtgctggag agcttcaagg tcagcttcct gagcgctctc    480
gaggagtaca ctaagaagct caacacccag taataagctt gc                      522

<210> SEQ ID NO 12
<211> LENGTH: 168
<212> TYPE: PRT
<213> ORGANISM: Artificial
<220> FEATURE:
<223> OTHER INFORMATION: MSP1D5D6

<400> SEQUENCE: 12

Met Gly His His His His His His Ile Glu Gly Arg Leu Lys Leu Leu
  1               5                  10                  15

Asp Asn Trp Asp Ser Val Thr Ser Thr Phe Ser Lys Leu Arg Glu Gln
             20                  25                  30

Leu Gly Pro Val Thr Gln Glu Phe Trp Asp Asn Leu Glu Lys Glu Thr
         35                  40                  45

Glu Gly Leu Arg Gln Glu Met Ser Lys Asp Leu Glu Glu Val Lys Ala
     50                  55                  60

Lys Val Gln Pro Tyr Leu Asp Asp Phe Gln Lys Lys Trp Gln Glu Glu
 65                  70                  75                  80

Met Glu Leu Tyr Arg Gln Lys Val Glu Pro Tyr Ser Asp Glu Leu Arg
                 85                  90                  95

Gln Arg Leu Ala Ala Arg Leu Glu Ala Leu Lys Glu Asn Gly Gly Ala
            100                 105                 110

Arg Leu Ala Glu Tyr His Ala Lys Ala Thr Glu His Leu Ser Thr Leu
        115                 120                 125

Ser Glu Lys Ala Lys Pro Ala Leu Glu Asp Leu Arg Gln Gly Leu Leu
    130                 135                 140

Pro Val Leu Glu Ser Phe Lys Val Ser Phe Leu Ser Ala Leu Glu Glu
145                 150                 155                 160

Tyr Thr Lys Lys Leu Asn Thr Gln
                165

<210> SEQ ID NO 13
<211> LENGTH: 522
<212> TYPE: DNA
<213> ORGANISM: Artificial
<220> FEATURE:
<223> OTHER INFORMATION: Nucleotide sequence encoding MSP1D6D7

<400> SEQUENCE: 13
tataccatgg gccatcatca tcatcatcat atagaaggaa gactaaagct ccttgacaac     60
tgggacagcg tgacctccac cttcagcaag ctgcgcgaac agctcggccc tgtgacccag    120
gagttctggg ataacctgga aaaggagaca gagggcctga ggcaggagat gagcaaggat    180
ctggaggagg tgaaggccaa ggtgcagccc tacctggacg acttccagaa gaagtggcag    240
gaggagatgg agctctaccg ccagaaggtg gagccgctgc gcgcagagct ccagagggc     300 gcgcgccaga gctgcacga gctgcaagag aagttgagcg ccaggctagc cgagtaccac    360
gccaaggcca ccgagcatct gagcacgctc agcgagaagg ccaaacccgc gctcgaggac    420
```

```
ctccgccaag gcctgctgcc cgtgctggag agcttcaagg tcagcttcct gagcgctctc    480
gaggagtaca ctaagaagct caacacccag taataagctt gc                       522
```

<210> SEQ ID NO 14
<211> LENGTH: 168
<212> TYPE: PRT
<213> ORGANISM: Artificial
<220> FEATURE:
<223> OTHER INFORMATION: MSP1D6D7

<400> SEQUENCE: 14

```
Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Ala
            100                 105                 110

Arg Leu Ala Glu Tyr His Ala Lys Ala Thr Glu His Leu Ser Thr Leu
        115                 120                 125

Ser Glu Lys Ala Lys Pro Ala Leu Glu Asp Leu Arg Gln Gly Leu Leu
130                 135                 140

Pro Val Leu Glu Ser Phe Lys Val Ser Phe Leu Ser Ala Leu Glu Glu
145                 150                 155                 160

Tyr Thr Lys Lys Leu Asn Thr Gln
                165
```

<210> SEQ ID NO 15
<211> LENGTH: 651
<212> TYPE: DNA
<213> ORGANISM: Artificial
<220> FEATURE:
<223> OTHER INFORMATION: Fully synthetic sequence encoding MSP1

<400> SEQUENCE: 15

```
accatgggtc atcatcatca tcatcacatt gagggacgtc tgaagctgtt ggacaattgg    60
gactctgtta cgtctacctt cagtaaactt cgcgaacaac tgggccccgt gacgcaggaa   120
ttctgggaca acctggaaaa agaaaccgag ggactgcgtc aggaaatgtc caaagattta   180
gaagaggtga aggccaaggt tcagccatat ctagatgact tcagaaaaaa atggcaggaa   240
gagatggaat tatatcgtca aaaggtggaa ccgctgcgtg cggaactgca gaggggggca   300
cgccaaaaac tccatgagct ccaagagaag ctcagcccat taggcgaaga aatgcgcgat   360
cgcgcccgtg cacatgttga tgcactccgg actcatttgg cgccgtattc ggatgaactt   420
cgccagcgtt tggccgcacg tctcgaggcg ctgaaagaaa acgggggtgc ccgcttggct   480
gagtaccacg cgaaagcgac agaacacctg agcaccttga gcgaaaaagc gaaaccggcg   540
ctggaagatc tacgccaggg cttattgcct gttcttgaga gctttaaagt cagttttctg   600
tcagctctgg aagaatatac taaaaagctg aatacccagt aataagcttg g            651
```

<210> SEQ ID NO 16
<211> LENGTH: 201
<212> TYPE: PRT
<213> ORGANISM: Artificial
<220> FEATURE:
<223> OTHER INFORMATION: MSP1D3

<400> SEQUENCE: 16

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Pro Tyr Leu Asp Asp Phe Gln Lys
    50                  55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln
        195                 200

<210> SEQ ID NO 17
<211> LENGTH: 201
<212> TYPE: PRT
<213> ORGANISM: Artificial
<220> FEATURE:
<223> OTHER INFORMATION: MSP1D9

<400> SEQUENCE: 17

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

```
Leu Gly Glu Glu Met Arg Asp Arg Ala Arg Ala His Val Asp Ala Leu
            115                 120                 125

Arg Thr His Leu Ala Pro Tyr Ser Asp Glu Leu Arg Gln Arg Leu Ala
        130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Val Leu Glu Ser Phe Lys Val Ser Phe Leu Ser Ala Leu Glu
            180                 185                 190

Glu Tyr Thr Lys Lys Leu Asn Thr Gln
        195                 200

<210> SEQ ID NO 18
<211> LENGTH: 392
<212> TYPE: PRT
<213> ORGANISM: Artificial
<220> FEATURE:
<223> OTHER INFORMATION: MSP2delta1

<400> SEQUENCE: 18

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Pro Tyr Leu Asp Asp Phe Gln Lys
    50                  55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln Gly Thr Leu Lys Leu Leu Asp
        195                 200                 205

Asn Trp Asp Ser Val Thr Ser Thr Phe Ser Lys Leu Arg Glu Gln Leu
    210                 215                 220

Gly Pro Val Thr Gln Glu Phe Trp Asp Asn Leu Glu Lys Glu Thr Glu
225                 230                 235                 240

Gly Leu Arg Gln Glu Met Ser Pro Tyr Leu Asp Asp Phe Gln Lys Lys
                245                 250                 255

Trp Gln Glu Glu Met Glu Leu Tyr Arg Gln Lys Val Glu Pro Leu Arg
            260                 265                 270
```

```
Ala Glu Leu Gln Glu Gly Ala Arg Gln Lys Leu His Glu Leu Gln Glu
        275                 280                 285

Lys Leu Ser Pro Leu Gly Glu Glu Met Arg Asp Arg Ala Arg Ala His
        290                 295                 300

Val Asp Ala Leu Arg Thr His Leu Ala Pro Tyr Ser Asp Glu Leu Arg
305                 310                 315                 320

Gln Arg Leu Ala Ala Arg Leu Glu Ala Leu Lys Glu Asn Gly Gly Ala
                325                 330                 335

Arg Leu Ala Glu Tyr His Ala Lys Ala Thr Glu His Leu Ser Thr Leu
            340                 345                 350

Ser Glu Lys Ala Lys Pro Ala Leu Glu Asp Leu Arg Gln Gly Leu Leu
        355                 360                 365

Pro Val Leu Glu Ser Phe Lys Val Ser Phe Leu Ser Ala Leu Glu Glu
    370                 375                 380

Tyr Thr Lys Lys Leu Asn Thr Gln
385                 390

<210> SEQ ID NO 19
<211> LENGTH: 43
<212> TYPE: PRT
<213> ORGANISM: Artificial
<220> FEATURE:
<223> OTHER INFORMATION: globular domain of apolipoprotein A1

<400> SEQUENCE: 19

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn
        35                  40

<210> SEQ ID NO 20
<211> LENGTH: 12
<212> TYPE: PRT
<213> ORGANISM: Artificial
<220> FEATURE:
<223> OTHER INFORMATION: His tag

<400> SEQUENCE: 20

Met Gly His His His His His His Ile Glu Gly Arg
1               5                   10

<210> SEQ ID NO 21
<211> LENGTH: 23
<212> TYPE: PRT
<213> ORGANISM: Artificial
<220> FEATURE:
<223> OTHER INFORMATION: HisTEV sequence

<400> SEQUENCE: 21

Met Gly His His His His His His Asp Tyr Asp Ile Pro Thr Thr
1               5                   10                  15

Glu Asn Leu Tyr Phe Gln Gly
            20

<210> SEQ ID NO 22
<211> LENGTH: 22
<212> TYPE: PRT
<213> ORGANISM: Artificial
<220> FEATURE:
```

```
<223> OTHER INFORMATION: Helix 1

<400> SEQUENCE: 22

Leu Lys Leu Leu Asp Asn Trp Asp Ser Val Thr Ser Thr Phe Ser Lys
1               5                   10                  15

Leu Arg Glu Gln Leu Gly
            20

<210> SEQ ID NO 23
<211> LENGTH: 22
<212> TYPE: PRT
<213> ORGANISM: Artificial
<220> FEATURE:
<223> OTHER INFORMATION: Helix 2

<400> SEQUENCE: 23

Pro Val Thr Gln Glu Phe Trp Asp Asn Leu Glu Lys Glu Thr Glu Gly
1               5                   10                  15

Leu Arg Gln Glu Met Ser
            20

<210> SEQ ID NO 24
<211> LENGTH: 11
<212> TYPE: PRT
<213> ORGANISM: Artificial
<220> FEATURE:
<223> OTHER INFORMATION: Helix 3

<400> SEQUENCE: 24

Lys Asp Leu Glu Glu Val Lys Ala Lys Val Gln
1               5                   10

<210> SEQ ID NO 25
<211> LENGTH: 22
<212> TYPE: PRT
<213> ORGANISM: Artificial
<220> FEATURE:
<223> OTHER INFORMATION: Helix 4

<400> SEQUENCE: 25

Pro Tyr Leu Asp Asp Phe Gln Lys Lys Trp Gln Glu Glu Met Glu Leu
1               5                   10                  15

Tyr Arg Gln Lys Val Glu
            20

<210> SEQ ID NO 26
<211> LENGTH: 22
<212> TYPE: PRT
<213> ORGANISM: Artificial
<220> FEATURE:
<223> OTHER INFORMATION: Helix 5

<400> SEQUENCE: 26

Pro Leu Arg Ala Glu Leu Gln Glu Gly Ala Arg Gln Lys Leu His Glu
1               5                   10                  15

Leu Gln Glu Lys Leu Ser
            20

<210> SEQ ID NO 27
<211> LENGTH: 22
<212> TYPE: PRT
<213> ORGANISM: Artificial
<220> FEATURE:
<223> OTHER INFORMATION: Helix 6
```

-continued

```
<400> SEQUENCE: 27

Pro Leu Gly Glu Glu Met Arg Asp Arg Ala Arg Ala His Val Asp Ala
1               5                   10                  15

Leu Arg Thr His Leu Ala
            20

<210> SEQ ID NO 28
<211> LENGTH: 22
<212> TYPE: PRT
<213> ORGANISM: Artificial
<220> FEATURE:
<223> OTHER INFORMATION: Helix 7

<400> SEQUENCE: 28

Pro Tyr Ser Asp Glu Leu Arg Gln Arg Leu Ala Ala Arg Leu Glu Ala
1               5                   10                  15

Leu Lys Glu Asn Gly Gly
            20

<210> SEQ ID NO 29
<211> LENGTH: 22
<212> TYPE: PRT
<213> ORGANISM: Artificial
<220> FEATURE:
<223> OTHER INFORMATION: Helix 8

<400> SEQUENCE: 29

Ala Arg Leu Ala Glu Tyr His Ala Lys Ala Thr Glu His Leu Ser Thr
1               5                   10                  15

Leu Ser Glu Lys Ala Lys
            20

<210> SEQ ID NO 30
<211> LENGTH: 11
<212> TYPE: PRT
<213> ORGANISM: Artificial
<220> FEATURE:
<223> OTHER INFORMATION: Helix 9

<400> SEQUENCE: 30

Pro Ala Leu Glu Asp Leu Arg Gln Gly Leu Leu
1               5                   10

<210> SEQ ID NO 31
<211> LENGTH: 24
<212> TYPE: PRT
<213> ORGANISM: Artificial
<220> FEATURE:
<223> OTHER INFORMATION: Helix 10

<400> SEQUENCE: 31

Pro Val Leu Glu Ser Phe Lys Val Ser Phe Leu Ser Ala Leu Glu Glu
1               5                   10                  15

Tyr Thr Lys Lys Leu Asn Thr Gln
            20

<210> SEQ ID NO 32
<211> LENGTH: 11
<212> TYPE: PRT
<213> ORGANISM: Artificial
<220> FEATURE:
<223> OTHER INFORMATION: Helix 0.5

<400> SEQUENCE: 32
```

-continued

```
Ser Thr Phe Ser Lys Leu Arg Glu Gln Leu Gly
1               5                   10
```

<210> SEQ ID NO 33
<211> LENGTH: 13
<212> TYPE: PRT
<213> ORGANISM: Artificial
<220> FEATURE:
<223> OTHER INFORMATION: Helix 10.5

<400> SEQUENCE: 33

```
Ser Ala Leu Glu Glu Tyr Thr Lys Lys Leu Asn Thr Gln
1               5                   10
```

<210> SEQ ID NO 34
<211> LENGTH: 22
<212> TYPE: PRT
<213> ORGANISM: Artificial
<220> FEATURE:
<223> OTHER INFORMATION: Helix 2S

<400> SEQUENCE: 34

```
Pro Val Thr Gln Glu Phe Trp Asp Asn Leu Glu Lys Glu Thr Glu Gly
1               5                   10                  15

Leu Arg Gln Glu Met Ser
            20
```

<210> SEQ ID NO 35
<211> LENGTH: 36
<212> TYPE: DNA
<213> ORGANISM: Artificial
<220> FEATURE:
<223> OTHER INFORMATION: Nucleotide sequence encoding His tag

<400> SEQUENCE: 35
atgggtcatc atcatcatca tcacattgag ggacgt                36

<210> SEQ ID NO 36
<211> LENGTH: 69
<212> TYPE: DNA
<213> ORGANISM: Artificial
<220> FEATURE:
<223> OTHER INFORMATION: Nucleotide sequence encoding HisTEV

<400> SEQUENCE: 36
atgggtcatc atcatcatca tcatcacgat tatgatattc ctactactga gaatttgtat    60
tttcagggt                                                            69

<210> SEQ ID NO 37
<211> LENGTH: 66
<212> TYPE: DNA
<213> ORGANISM: Artificial
<220> FEATURE:
<223> OTHER INFORMATION: Nucleotide sequence encoding Helix 1

<400> SEQUENCE: 37
ctgaagctgt tggacaattg ggactctgtt acgtctacct tcagtaaact tcgcgaacaa    60
ctgggc                                                               66

<210> SEQ ID NO 38
<211> LENGTH: 66
<212> TYPE: DNA
<213> ORGANISM: Artificial
<220> FEATURE:
<223> OTHER INFORMATION: Nucleotide sequence encoding Helix 2

-continued

<400> SEQUENCE: 38
cccgtgacgc aggaattctg ggacaacctg gaaaagaaa ccgagggact gcgtcaggaa    60
atgtcc    66

<210> SEQ ID NO 39
<211> LENGTH: 33
<212> TYPE: DNA
<213> ORGANISM: Artificial
<220> FEATURE:
<223> OTHER INFORMATION: Nucleotide sequence encoding Helix 3

<400> SEQUENCE: 39
aaagatttag aagaggtgaa ggccaaggtt cag    33

<210> SEQ ID NO 40
<211> LENGTH: 66
<212> TYPE: DNA
<213> ORGANISM: Artificial
<220> FEATURE:
<223> OTHER INFORMATION: Nucleotide sequence encoding Helix 4

<400> SEQUENCE: 40
ccatatctcg atgactttca gaaaaaatgg caggaagaga tggaattata tcgtcaaaag    60
gtggaa    66

<210> SEQ ID NO 41
<211> LENGTH: 66
<212> TYPE: DNA
<213> ORGANISM: Artificial
<220> FEATURE:
<223> OTHER INFORMATION: Nucleotide sequence encoding Helix 5

<400> SEQUENCE: 41
ccgctgcgtg cggaactgca gagggggca cgccaaaaac tccatgagct ccaagagaag    60
ctcagc    66

<210> SEQ ID NO 42
<211> LENGTH: 66
<212> TYPE: DNA
<213> ORGANISM: Artificial
<220> FEATURE:
<223> OTHER INFORMATION: Nucleotide sequence encoding Helix 6

<400> SEQUENCE: 42
ccattaggcg aagaaatgcg cgatcgcgcc cgtgcacatg ttgatgcact ccggactcat    60
ttggcg    66

<210> SEQ ID NO 43
<211> LENGTH: 66
<212> TYPE: DNA
<213> ORGANISM: Artificial
<220> FEATURE:
<223> OTHER INFORMATION: Nucleotide sequence encoding Helix 7

<400> SEQUENCE: 43
ccgtattcgg atgaacttcg ccagcgtttg gccgcacgtc tcgaggcgct gaaagaaaac    60
gggggt    66

<210> SEQ ID NO 44
<211> LENGTH: 66
<212> TYPE: DNA

-continued

```
<213> ORGANISM: Artificial
<220> FEATURE:
<223> OTHER INFORMATION: Nucleotide sequence encoding Helix 8

<400> SEQUENCE: 44
gcccgcttgg ctgagtacca cgcgaaagcg acagaacacc tgagcacctt gagcgaaaaa    60
gcgaaa                                                               66

<210> SEQ ID NO 45
<211> LENGTH: 33
<212> TYPE: DNA
<213> ORGANISM: Artificial
<220> FEATURE:
<223> OTHER INFORMATION: Nucleotide sequence encoding Helix 9

<400> SEQUENCE: 45
ccggcgctgg aagatctacg ccagggctta ttg                                 33

<210> SEQ ID NO 46
<211> LENGTH: 72
<212> TYPE: DNA
<213> ORGANISM: Artificial
<220> FEATURE:
<223> OTHER INFORMATION: Nucleotide sequence encoding Helix 10

<400> SEQUENCE: 46
cctgttcttg agagctttaa agtcagtttt ctgtcagctc tggaagaata tactaaaaag    60
ctgaataccc ag                                                        72

<210> SEQ ID NO 47
<211> LENGTH: 33
<212> TYPE: DNA
<213> ORGANISM: Artificial
<220> FEATURE:
<223> OTHER INFORMATION: Nucleotide sequence encoding Helix 0.5

<400> SEQUENCE: 47
tctaccttca gtaaacttcg cgaacaactg ggc                                 33

<210> SEQ ID NO 48
<211> LENGTH: 49
<212> TYPE: DNA
<213> ORGANISM: Artificial
<220> FEATURE:
<223> OTHER INFORMATION: Nucleotide sequence encoding Helix 10.5

<400> SEQUENCE: 48
cagttttctg tcagctctgg aagaatatac taaaaagctg aatacccag                49

<210> SEQ ID NO 49
<211> LENGTH: 66
<212> TYPE: DNA
<213> ORGANISM: Artificial
<220> FEATURE:
<223> OTHER INFORMATION: Nucleotide sequence encoding Helix 2S

<400> SEQUENCE: 49
tccgtgacgc aggaattctg ggacaacctg gaaaagaaa ccgagggact gcgtcaggaa     60
atgtcc                                                               66

<210> SEQ ID NO 50
<211> LENGTH: 234
<212> TYPE: PRT
<213> ORGANISM: Artificial
```

```
<220> FEATURE:
<223> OTHER INFORMATION: MSP1E1

<400> SEQUENCE: 50

Met Gly His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
                35                  40                  45

Glu Gly Leu Arg Gln Glu Met Ser Lys Asp Leu Glu Glu Val Lys Ala
50                      55                  60

Lys Val Gln Pro Tyr Leu Asp Asp Phe Gln Lys Lys Trp Gln Gln Glu
65                  70                  75                  80

Met Glu Leu Tyr Arg Gln Cys Val Glu Pro Tyr Leu Asp Asp Phe Gln
                85                  90                  95

Lys Lys Trp Gln Glu Glu Met Glu Leu Tyr Arg Gln Lys Val Glu Pro
                100                 105                 110

Leu Arg Ala Glu Leu Gln Glu Gly Ala Arg Gln Lys Leu His Glu Leu
            115                 120                 125

Gln Glu Lys Leu Ser Pro Leu Gly Glu Glu Met Arg Asp Arg Ala Arg
130                 135                 140

Ala His Val Asp Ala Leu Arg Thr His Leu Ala Pro Tyr Ser Asp Glu
145                 150                 155                 160

Leu Arg Gln Arg Leu Ala Ala Arg Leu Glu Ala Leu Lys Glu Asn Gly
                165                 170                 175

Gly Ala Arg Leu Ala Glu Tyr His Ala Lys Ala Thr Glu His Leu Ser
            180                 185                 190

Thr Leu Ser Glu Lys Ala Lys Pro Ala Leu Glu Asp Leu Arg Gln Gly
        195                 200                 205

Leu Leu Pro Val Leu Glu Ser Phe Lys Val Ser Phe Leu Ser Ala Leu
210                 215                 220

Glu Glu Tyr Thr Lys Lys Leu Asn Thr Gln
225                 230

<210> SEQ ID NO 51
<211> LENGTH: 256
<212> TYPE: PRT
<213> ORGANISM: Artificial
<220> FEATURE:
<223> OTHER INFORMATION: MSP1E2

<400> SEQUENCE: 51

Met Gly His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
                35                  40                  45

Glu Gly Leu Arg Gln Glu Met Ser Lys Asp Leu Glu Glu Val Lys Ala
50                      55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Tyr Leu Cys Cys Phe Gln
                85                  90                  95

Lys Lys Trp Gln Glu Glu Met Glu Leu Tyr Arg Gln Lys Val Glu Pro
```

```
                    100                 105                 110
Leu Arg Ala Glu Leu Gln Glu Gly Ala Arg Gln Lys Leu His Glu Leu
            115                 120                 125

Gln Glu Lys Leu Ser Pro Leu Arg Ala Glu Leu Gln Glu Gly Ala Arg
130                 135                 140

Gln Lys Leu His Glu Leu Gln Glu Lys Leu Ser Pro Leu Gly Glu Glu
145                 150                 155                 160

Met Arg Asp Arg Ala Arg Ala His Val Asp Ala Leu Arg Thr His Leu
                165                 170                 175

Ala Pro Tyr Ser Asp Glu Leu Arg Gln Arg Leu Ala Ala Arg Leu Glu
            180                 185                 190

Ala Leu Lys Glu Asn Gly Gly Ala Arg Leu Ala Glu Tyr His Ala Lys
            195                 200                 205

Ala Thr Glu His Leu Ser Thr Leu Ser Glu Lys Ala Lys Pro Ala Leu
            210                 215                 220

Glu Asp Leu Arg Gln Gly Leu Leu Pro Val Leu Glu Ser Phe Lys Val
225                 230                 235                 240

Ser Phe Leu Ser Ala Leu Glu Glu Tyr Thr Lys Lys Leu Asn Thr Gln
            245                 250                 255

<210> SEQ ID NO 52
<211> LENGTH: 278
<212> TYPE: PRT
<213> ORGANISM: Artificial
<220> FEATURE:
<223> OTHER INFORMATION: MSP1E3

<400> SEQUENCE: 52

Met Gly His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
            35                  40                  45

Glu Gly Leu Arg Gln Glu Met Ser Lys Asp Leu Glu Glu Val Lys Ala
            50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Tyr Leu Asp Asp Phe Gln
                85                  90                  95

Lys Lys Trp Gln Glu Glu Met Glu Leu Tyr Arg Gln Lys Val Glu Pro
            100                 105                 110

Leu Arg Ala Glu Leu Gln Glu Gly Ala Arg Gln Lys Leu His Glu Leu
            115                 120                 125

Gln Glu Lys Leu Ser Pro Leu Gly Glu Glu Met Arg Asp Arg Ala Arg
130                 135                 140

Ala His Val Asp Ala Leu Arg Thr His Leu Ala Pro Leu Arg Ala Glu
145                 150                 155                 160

Leu Gln Glu Gly Ala Arg Gln Lys Leu His Glu Leu Gln Glu Lys Leu
                165                 170                 175

Ser Pro Leu Gly Glu Glu Met Arg Asp Arg Ala Arg Ala His Val Asp
            180                 185                 190

Ala Leu Arg Thr His Leu Ala Pro Tyr Ser Asp Glu Leu Arg Gln Arg
            195                 200                 205

Leu Ala Ala Arg Leu Glu Ala Leu Lys Glu Asn Gly Gly Ala Arg Leu
```

```
                    210                 215                 220
Ala Glu Tyr His Ala Lys Ala Thr Glu His Leu Ser Thr Leu Ser Glu
225                 230                 235                 240

Lys Ala Lys Pro Ala Leu Glu Asp Leu Arg Gln Gly Leu Leu Pro Val
                245                 250                 255

Leu Glu Ser Phe Lys Val Ser Phe Leu Ser Ala Leu Glu Glu Tyr Thr
                260                 265                 270

Lys Lys Leu Asn Thr Gln
        275
```

<210> SEQ ID NO 53
<211> LENGTH: 223
<212> TYPE: PRT
<213> ORGANISM: Artificial
<220> FEATURE:
<223> OTHER INFORMATION: MSP1TEV

<400> SEQUENCE: 53

```
Met Gly His His His His His His Asp Tyr Asp Ile Pro Thr Thr
1               5                   10                  15

Glu Asn Leu Tyr Phe Gln Gly Leu Lys Leu Leu Asp Asn Trp Asp Ser
                20                  25                  30

Val Thr Ser Thr Phe Ser Lys Leu Arg Glu Gln Leu Gly Pro Val Thr
            35                  40                  45

Gln Glu Phe Trp Asp Asn Leu Glu Lys Glu Thr Glu Gly Leu Arg Gln
        50                  55                  60

Glu Met Ser Lys Asp Leu Glu Glu Val Lys Ala Lys Val Gln Pro Tyr
65                  70                  75                  80

Leu Asp Asp Phe Gln Lys Lys Trp Gln Glu Glu Met Glu Leu Tyr Arg
                85                  90                  95

Gln Lys Val Glu Pro Leu Arg Ala Glu Leu Gln Glu Gly Ala Arg Gln
            100                 105                 110

Lys Leu His Glu Leu Gln Glu Lys Leu Ser Pro Leu Gly Glu Glu Met
        115                 120                 125

Arg Asp Arg Ala Arg Ala His Val Asp Ala Leu Arg Thr His Leu Ala
130                 135                 140

Pro Tyr Ser Asp Glu Leu Arg Gln Arg Leu Ala Ala Arg Leu Glu Ala
145                 150                 155                 160

Leu Lys Glu Asn Gly Gly Ala Arg Leu Ala Glu Tyr His Ala Lys Ala
                165                 170                 175

Thr Glu His Leu Ser Thr Leu Ser Glu Lys Ala Lys Pro Ala Leu Glu
            180                 185                 190

Asp Leu Arg Gln Gly Leu Leu Pro Val Leu Glu Ser Phe Lys Val Ser
        195                 200                 205

Phe Leu Ser Ala Leu Glu Glu Tyr Thr Lys Lys Leu Asn Thr Gln
    210                 215                 220
```

<210> SEQ ID NO 54
<211> LENGTH: 200
<212> TYPE: PRT
<213> ORGANISM: Artificial
<220> FEATURE:
<223> OTHER INFORMATION: MSP1NH

<400> SEQUENCE: 54

```
Leu Lys Leu Leu Asp Asn Trp Asp Ser Val Thr Ser Thr Phe Ser Lys
1               5                   10                  15
```

```
Leu Arg Glu Gln Leu Gly Pro Val Thr Gln Glu Phe Trp Asp Asn Leu
            20                  25                  30

Glu Lys Glu Thr Glu Gly Leu Arg Gln Glu Met Ser Lys Asp Leu Glu
        35                  40                  45

Glu Val Lys Ala Lys Val Gln Pro Tyr Leu Asp Asp Phe Gln Lys Lys
 50                  55                  60

Trp Gln Glu Glu Met Glu Leu Tyr Arg Gln Lys Val Glu Pro Leu Arg
 65                  70                  75                  80

Ala Glu Leu Gln Glu Gly Ala Arg Gln Lys Leu His Glu Leu Gln Glu
                85                  90                  95

Lys Leu Ser Pro Leu Gly Glu Glu Met Arg Asp Arg Ala Arg Ala His
            100                 105                 110

Val Asp Ala Leu Arg Thr His Leu Ala Pro Tyr Ser Asp Glu Leu Arg
        115                 120                 125

Gln Arg Leu Ala Ala Arg Leu Glu Ala Leu Lys Glu Asn Gly Gly Ala
130                 135                 140

Arg Leu Ala Glu Tyr His Ala Lys Ala Thr Glu His Leu Ser Thr Leu
145                 150                 155                 160

Ser Glu Lys Ala Lys Pro Ala Leu Glu Asp Leu Arg Gln Gly Leu Leu
                165                 170                 175

Pro Val Leu Glu Ser Phe Lys Val Ser Phe Leu Ser Ala Leu Glu Glu
            180                 185                 190

Tyr Thr Lys Lys Leu Ser Thr Gln
        195                 200

<210> SEQ ID NO 55
<211> LENGTH: 212
<212> TYPE: PRT
<213> ORGANISM: Artificial
<220> FEATURE:
<223> OTHER INFORMATION: MSP1T2

<400> SEQUENCE: 55

Met Gly His His His His His His Asp Tyr Asp Ile Pro Thr Thr
 1               5                  10                  15

Glu Asn Leu Tyr Phe Gln Gly Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
 50                  55                  60

Lys Val Gln Pro Tyr Leu Asp Asp Phe Gln Lys Lys Trp Gln Glu Glu
 65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175
```

```
Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
            195                 200                 205

Leu Asn Thr Gln
    210

<210> SEQ ID NO 56
<211> LENGTH: 189
<212> TYPE: PRT
<213> ORGANISM: Artificial
<220> FEATURE:
<223> OTHER INFORMATION: MSP1T2NH

<400> SEQUENCE: 56

Ser Thr Phe Ser Lys Leu Arg Glu Gln Leu Gly Pro Val Thr Gln Glu
1               5                   10                  15

Phe Trp Asp Asn Leu Glu Lys Glu Thr Glu Gly Leu Arg Gln Glu Met
            20                  25                  30

Ser Lys Asp Leu Glu Glu Val Lys Ala Lys Val Gln Pro Tyr Leu Asp
            35                  40                  45

Asp Phe Gln Lys Lys Trp Gln Glu Glu Met Glu Leu Tyr Arg Gln Lys
        50                  55                  60

Val Glu Pro Leu Arg Ala Glu Leu Gln Glu Gly Ala Arg Gln Lys Leu
65                  70                  75                  80

His Glu Leu Gln Glu Lys Leu Ser Pro Leu Gly Glu Glu Met Arg Asp
                85                  90                  95

Arg Ala Arg Ala His Val Asp Ala Leu Arg Thr His Leu Ala Pro Tyr
            100                 105                 110

Ser Asp Glu Leu Arg Gln Arg Leu Ala Ala Arg Leu Glu Ala Leu Lys
            115                 120                 125

Glu Asn Gly Gly Ala Arg Leu Ala Glu Tyr His Ala Lys Ala Thr Glu
        130                 135                 140

His Leu Ser Thr Leu Ser Glu Lys Ala Lys Pro Ala Leu Glu Asp Leu
145                 150                 155                 160

Arg Gln Gly Leu Leu Pro Val Leu Glu Ser Phe Lys Val Ser Phe Leu
                165                 170                 175

Ser Ala Leu Glu Glu Tyr Thr Lys Lys Leu Asn Thr Gln
            180                 185

<210> SEQ ID NO 57
<211> LENGTH: 201
<212> TYPE: PRT
<213> ORGANISM: Artificial
<220> FEATURE:
<223> OTHER INFORMATION: MSP1T3

<400> SEQUENCE: 57

Met Gly His His His His His His Asp Tyr Asp Ile Pro Thr Thr
1               5                   10                  15

Glu Asn Leu Tyr Phe Gln Gly Pro Val Thr Gln Glu Phe Trp Asp Asn
            20                  25                  30

Leu Glu Lys Glu Thr Glu Gly Leu Arg Gln Glu Met Ser Lys Asp Leu
            35                  40                  45

Glu Glu Val Lys Ala Lys Val Gln Pro Tyr Leu Asp Asp Phe Gln Lys
        50                  55                  60

Lys Trp Gln Glu Glu Met Glu Leu Tyr Arg Gln Lys Val Glu Pro Leu
65                  70                  75                  80
```

Arg Ala Glu Leu Gln Glu Gly Ala Arg Gln Lys Leu His Glu Leu Gln
                    85                  90                  95

Glu Lys Leu Ser Pro Leu Gly Glu Glu Met Arg Asp Arg Ala Arg Ala
                100                 105                 110

His Val Asp Ala Leu Arg Thr His Leu Ala Pro Tyr Ser Asp Glu Leu
            115                 120                 125

Arg Gln Arg Leu Ala Ala Arg Leu Glu Ala Leu Lys Glu Ser Gly Gly
        130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
                180                 185                 190

Glu Tyr Thr Lys Lys Leu Asn Thr Gln
            195                 200

<210> SEQ ID NO 58
<211> LENGTH: 190
<212> TYPE: PRT
<213> ORGANISM: Artificial
<220> FEATURE:
<223> OTHER INFORMATION: MSP1D3D9

<400> SEQUENCE: 58

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Pro Tyr Leu Asp Asp Phe Gln Lys
    50                  55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
                100                 105                 110

His Val Asp Ala Leu Arg Thr His Leu Ala Pro Tyr Ser Asp Glu Leu
            115                 120                 125

Arg Gln Arg Leu Ala Ala Arg Leu Glu Ala Leu Lys Glu Asn Gly Gly
        130                 135                 140

Ala Arg Leu Ala Glu Tyr His Ala Lys Ala Thr Glu His Leu Ser Thr
145                 150                 155                 160

Leu Ser Glu Lys Ala Lys Pro Val Leu Glu Ser Phe Lys Val Ser Phe
                165                 170                 175

Leu Ser Ala Leu Glu Glu Tyr Thr Lys Lys Leu Asn Thr Gln
            180                 185                 190

<210> SEQ ID NO 59
<211> LENGTH: 201
<212> TYPE: PRT
<213> ORGANISM: Artificial
<220> FEATURE:
<223> OTHER INFORMATION: MSP1D10.5

```
<400> SEQUENCE: 59

Met Gly His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
            35                  40                  45

Glu Gly Leu Arg Gln Glu Met Ser Lys Asp Leu Glu Glu Val Lys Ala
        50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Ser Ala Leu Glu
            180                 185                 190

Glu Tyr Thr Lys Lys Leu Asn Thr Gln
        195                 200

<210> SEQ ID NO 60
<211> LENGTH: 190
<212> TYPE: PRT
<213> ORGANISM: Artificial
<220> FEATURE:
<223> OTHER INFORMATION: MSP1D3D10.5

<400> SEQUENCE: 60

Met Gly His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
            35                  40                  45

Glu Gly Leu Arg Gln Glu Met Ser Pro Tyr Leu Asp Asp Phe Gln Lys
        50                  55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
130                 135                 140

Ala Arg Leu Ala Glu Tyr His Ala Lys Ala Thr Glu His Leu Ser Thr
```

```
                145                 150                 155                 160
Leu Ser Glu Lys Ala Lys Pro Ala Leu Glu Asp Leu Arg Gln Gly Leu
                    165                 170                 175
Leu Ser Ala Leu Glu Glu Tyr Thr Lys Lys Leu Asn Thr Gln
                180                 185                 190

<210> SEQ ID NO 61
<211> LENGTH: 201
<212> TYPE: PRT
<213> ORGANISM: Artificial
<220> FEATURE:
<223> OTHER INFORMATION: MSP1T4

<400> SEQUENCE: 61

Met Gly His His His His His His Asp Tyr Asp Ile Pro Thr Thr
1               5                   10                  15

Glu Asn Leu Tyr Phe Gln Gly Ser Val Thr Gln Glu Phe Trp Asp Asn
                20                  25                  30

Leu Glu Lys Glu Thr Glu Gly Leu Arg Gln Glu Met Ser Lys Asp Leu
            35                  40                  45

Glu Glu Val Lys Ala Lys Val Gln Pro Tyr Leu Asp Asp Phe Gln Lys
        50                  55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
                100                 105                 110

His Val Asp Ala Leu Arg Thr His Leu Ala Pro Tyr Ser Asp Glu Leu
            115                 120                 125

Arg Gln Arg Leu Ala Ala Arg Leu Glu Ala Leu Lys Glu Asn Gly Gly
        130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
                180                 185                 190

Glu Tyr Thr Lys Lys Leu Asn Thr Gln
            195                 200

<210> SEQ ID NO 62
<211> LENGTH: 190
<212> TYPE: PRT
<213> ORGANISM: Artificial
<220> FEATURE:
<223> OTHER INFORMATION: MSP1T5

<400> SEQUENCE: 62

Met Gly His His His His His His Asp Tyr Asp Ile Pro Thr Thr
1               5                   10                  15

Glu Asn Leu Tyr Phe Gln Gly Lys Glu Thr Glu Gly Leu Arg Gln Glu
                20                  25                  30

Met Ser Lys Asp Leu Glu Glu Val Lys Ala Lys Val Gln Pro Tyr Leu
            35                  40                  45

Asp Asp Phe Gln Lys Lys Trp Gln Glu Glu Met Glu Leu Tyr Arg Gln
        50                  55                  60
```

```
Lys Val Glu Pro Leu Arg Ala Glu Leu Gln Glu Gly Ala Arg Gln Lys
 65                  70                  75                  80

Leu His Glu Leu Gln Glu Lys Leu Ser Pro Leu Gly Glu Glu Met Arg
                 85                  90                  95

Asp Arg Ala Arg Ala His Val Asp Ala Leu Arg Thr His Leu Ala Pro
            100                 105                 110

Tyr Ser Asp Glu Leu Arg Gln Arg Leu Ala Ala Arg Leu Glu Ala Leu
        115                 120                 125

Lys Glu Asn Gly Gly Ala Arg Leu Ala Glu Tyr His Ala Lys Ala Thr
    130                 135                 140

Glu His Leu Ser Thr Leu Ser Glu Lys Ala Lys Pro Ala Leu Glu Asp
145                 150                 155                 160

Leu Arg Gln Gly Leu Leu Pro Val Leu Glu Ser Phe Lys Val Ser Phe
                165                 170                 175

Leu Ser Ala Leu Glu Glu Tyr Thr Lys Lys Leu Asn Thr Gln
            180                 185                 190
```

<210> SEQ ID NO 63
<211> LENGTH: 179
<212> TYPE: PRT
<213> ORGANISM: Artificial
<220> FEATURE:
<223> OTHER INFORMATION: MSP1T6

<400> SEQUENCE: 63

```
Met Gly His His His His His His Asp Tyr Asp Ile Pro Thr Thr
  1               5                  10                  15

Glu Asn Leu Tyr Phe Gln Gly Lys Asp Leu Glu Glu Val Lys Ala Lys
                 20                  25                  30

Val Gln Pro Tyr Leu Asp Asp Phe Gln Lys Lys Trp Gln Glu Glu Met
             35                  40                  45

Glu Leu Tyr Arg Gln Lys Val Glu Pro Leu Arg Ala Glu Leu Gln Glu
         50                  55                  60

Gly Ala Arg Gln Lys Leu His Glu Leu Gln Glu Lys Leu Ser Pro Leu
 65                  70                  75                  80

Gly Glu Glu Met Arg Asp Arg Ala Arg Ala His Val Asp Ala Leu Arg
                 85                  90                  95

Thr His Leu Ala Pro Tyr Ser Asp Glu Leu Arg Gln Arg Leu Ala Ala
            100                 105                 110

Arg Leu Glu Ala Leu Lys Glu Asn Gly Gly Ala Arg Leu Ala Glu Tyr
        115                 120                 125

His Ala Lys Ala Thr Glu His Leu Ser Thr Leu Ser Glu Lys Ala Lys
    130                 135                 140

Pro Ala Leu Glu Asp Leu Arg Gln Gly Leu Leu Pro Val Leu Glu Ser
145                 150                 155                 160

Phe Lys Val Ser Phe Leu Ser Ala Leu Glu Glu Tyr Thr Lys Lys Leu
                165                 170                 175

Asn Thr Gln
```

<210> SEQ ID NO 64
<211> LENGTH: 289
<212> TYPE: PRT
<213> ORGANISM: Artificial
<220> FEATURE:
<223> OTHER INFORMATION: MSP1E3TEV

<400> SEQUENCE: 64

```
Met Gly His His His His His His Asp Tyr Asp Ile Pro Thr Thr
1               5                   10                  15

Glu Asn Leu Tyr Phe Gln Gly Leu Lys Leu Leu Asp Asn Trp Asp Ser
                20                  25                  30

Val Thr Ser Thr Phe Ser Lys Leu Arg Glu Gln Leu Gly Pro Val Thr
            35                  40                  45

Gln Glu Phe Trp Asp Asn Leu Glu Lys Glu Thr Glu Gly Leu Arg Gln
50                  55                  60

Glu Met Ser Lys Asp Leu Glu Glu Val Lys Ala Lys Val Gln Pro Tyr
65                  70                  75                  80

Leu Asp Asp Phe Gln Lys Lys Trp Gln Glu Met Glu Leu Tyr Arg
                85                  90                  95

Gln Lys Val Glu Pro Leu Arg Ala Glu Leu Gln Glu Gly Ala Arg Gln
                100                 105                 110

Lys Leu His Glu Leu Gln Glu Lys Leu Ser Pro Leu Gly Glu Glu Met
            115                 120                 125

Arg Asp Arg Ala Arg Ala His Val Asp Ala Leu Arg Thr His Leu Ala
130                 135                 140

Pro Tyr Leu Asp Asp Phe Gln Lys Lys Trp Gln Glu Glu Met Glu Leu
145                 150                 155                 160

Tyr Arg Gln Lys Val Glu Pro Leu Arg Ala Glu Leu Gln Glu Gly Ala
                165                 170                 175

Arg Gln Lys Leu His Glu Leu Gln Glu Lys Leu Ser Pro Leu Gly Glu
                180                 185                 190

Glu Met Arg Asp Arg Ala Arg Ala His Val Asp Ala Leu Arg Thr His
            195                 200                 205

Leu Ala Pro Tyr Ser Asp Glu Leu Arg Gln Arg Leu Ala Ala Arg Leu
210                 215                 220

Glu Ala Leu Lys Glu Asn Gly Gly Ala Arg Leu Ala Glu Tyr His Ala
225                 230                 235                 240

Lys Ala Thr Glu His Leu Ser Thr Leu Ser Glu Lys Ala Lys Pro Ala
                245                 250                 255

Leu Glu Asp Leu Arg Gln Gly Leu Leu Pro Val Leu Glu Ser Phe Lys
                260                 265                 270

Val Ser Phe Leu Ser Ala Leu Glu Glu Tyr Thr Lys Lys Leu Asn Thr
            275                 280                 285

Gln

<210> SEQ ID NO 65
<211> LENGTH: 278
<212> TYPE: PRT
<213> ORGANISM: Artificial
<220> FEATURE:
<223> OTHER INFORMATION: MSP1E3D1

<400> SEQUENCE: 65

Met Gly His His His His His His Asp Tyr Asp Ile Pro Thr Thr
1               5                   10                  15

Glu Asn Leu Tyr Phe Gln Gly Ser Thr Phe Ser Lys Leu Arg Glu Gln
                20                  25                  30

Leu Gly Pro Val Thr Gln Glu Phe Trp Asp Asn Leu Glu Lys Glu Thr
            35                  40                  45

Glu Gly Leu Arg Gln Glu Met Ser Lys Asp Leu Glu Glu Val Lys Ala
50                  55                  60

Lys Val Gln Pro Tyr Leu Asp Asp Phe Gln Lys Lys Trp Gln Glu Glu
```

```
                 65                  70                  75                  80
Met Glu Leu Tyr Arg Gln Lys Val Glu Pro Leu Arg Ala Glu Leu Gln
                    85                  90                  95

Glu Gly Ala Arg Gln Lys Leu His Glu Leu Gln Glu Lys Leu Ser Pro
                100                 105                 110

Leu Gly Glu Glu Met Arg Asp Arg Ala Arg Ala His Val Asp Ala Leu
                115                 120                 125

Arg Thr His Leu Ala Pro Tyr Leu Asp Asp Phe Gln Lys Lys Trp Gln
        130                 135                 140

Glu Glu Met Glu Leu Tyr Arg Gln Lys Val Glu Pro Leu Arg Ala Glu
145                 150                 155                 160

Leu Gln Glu Gly Ala Arg Gln Lys Leu His Glu Leu Gln Glu Lys Leu
                    165                 170                 175

Ser Pro Leu Gly Glu Glu Met Arg Asp Arg Ala Arg Ala His Val Asp
                180                 185                 190

Ala Leu Arg Thr His Leu Ala Pro Tyr Ser Asp Glu Leu Arg Gln Arg
            195                 200                 205

Leu Ala Ala Arg Leu Glu Ala Leu Lys Glu Asn Gly Gly Ala Arg Leu
    210                 215                 220

Ala Glu Tyr His Ala Lys Ala Thr Glu His Leu Ser Thr Leu Ser Glu
225                 230                 235                 240

Lys Ala Lys Pro Ala Leu Glu Asp Leu Arg Gln Gly Leu Leu Pro Val
                    245                 250                 255

Leu Glu Ser Phe Lys Val Ser Phe Leu Ser Ala Leu Glu Glu Tyr Thr
                260                 265                 270

Lys Lys Leu Asn Thr Gln
        275

<210> SEQ ID NO 66
<211> LENGTH: 423
<212> TYPE: PRT
<213> ORGANISM: Artificial
<220> FEATURE:
<223> OTHER INFORMATION: MSP2TEV

<400> SEQUENCE: 66

Met Gly His His His His His His Asp Tyr Asp Ile Pro Thr Thr
1               5                   10                  15

Glu Asn Leu Tyr Phe Gln Gly Leu Lys Leu Leu Asp Asn Trp Asp Ser
                20                  25                  30

Val Thr Ser Thr Phe Ser Lys Leu Arg Glu Gln Leu Gly Pro Val Thr
            35                  40                  45

Gln Glu Phe Trp Asp Asn Leu Glu Lys Glu Thr Glu Gly Leu Arg Gln
        50                  55                  60

Glu Met Ser Lys Asp Leu Glu Glu Val Lys Ala Lys Val Gln Pro Tyr
65                  70                  75                  80

Leu Asp Asp Phe Gln Lys Lys Trp Gln Glu Glu Met Glu Leu Tyr Arg
                    85                  90                  95

Gln Lys Val Glu Pro Leu Arg Ala Glu Leu Gln Glu Gly Ala Arg Gln
                100                 105                 110

Lys Leu His Glu Leu Gln Glu Lys Leu Ser Pro Leu Gly Glu Glu Met
            115                 120                 125

Arg Asp Arg Ala Arg Ala His Val Asp Ala Leu Arg Thr His Leu Ala
        130                 135                 140

Pro Tyr Ser Asp Glu Leu Arg Gln Arg Leu Ala Ala Arg Leu Glu Ala
```

```
                    145                 150                 155                 160
Leu Lys Glu Asn Gly Gly Ala Arg Leu Ala Glu Tyr His Ala Lys Ala
                165                 170                 175

Thr Glu His Leu Ser Thr Leu Ser Glu Lys Ala Lys Pro Ala Leu Glu
            180                 185                 190

Asp Leu Arg Gln Gly Leu Leu Pro Val Leu Glu Ser Phe Lys Val Ser
        195                 200                 205

Phe Leu Ser Ala Leu Glu Tyr Thr Lys Lys Leu Asn Thr Gln Gly Thr
    210                 215                 220

Leu Lys Leu Leu Asp Asn Trp Asp Ser Val Thr Ser Thr Phe Ser Lys
225                 230                 235                 240

Leu Arg Glu Gln Leu Gly Pro Val Thr Gln Glu Phe Trp Asp Asn Leu
                245                 250                 255

Glu Lys Glu Thr Glu Gly Leu Arg Gln Glu Met Lys Asp Leu Glu Glu
            260                 265                 270

Val Lys Ala Lys Val Gln Pro Tyr Leu Asp Asp Phe Gln Lys Lys Trp
        275                 280                 285

Gln Glu Glu Met Glu Leu Tyr Arg Gln Lys Val Glu Pro Leu Arg Ala
    290                 295                 300

Glu Leu Gln Glu Gly Ala Arg Gln Lys Leu His Glu Leu Gln Glu Lys
305                 310                 315                 320

Leu Ser Pro Leu Gly Glu Glu Met Arg Asp Arg Ala Arg Ala His Val
                325                 330                 335

Asp Ala Leu Arg Thr His Leu Ala Pro Tyr Ser Asp Glu Leu Arg Gln
            340                 345                 350

Arg Leu Ala Ala Arg Leu Glu Ala Leu Lys Glu Asn Gly Gly Ala Arg
        355                 360                 365

Leu Ala Glu Tyr His Ala Lys Ala Thr Glu His Leu Ser Thr Leu Ser
    370                 375                 380

Glu Lys Ala Lys Pro Ala Leu Glu Asp Leu Arg Gln Gly Leu Leu Pro
385                 390                 395                 400

Val Leu Glu Ser Phe Lys Val Ser Phe Leu Ser Ala Leu Glu Glu Tyr
                405                 410                 415

Thr Lys Lys Leu Asn Thr Gln
            420

<210> SEQ ID NO 67
<211> LENGTH: 199
<212> TYPE: PRT
<213> ORGANISM: Artificial
<220> FEATURE:
<223> OTHER INFORMATION: MSP1N1

<400> SEQUENCE: 67

Met Gly His His His His His His Asp Tyr Asp Ile Pro Thr Thr
1               5                   10                  15

Glu Asn Leu Tyr Phe Gln Gly Ser Val Thr Gln Glu Phe Trp Asp Asn
                20                  25                  30

Leu Glu Lys Glu Thr Glu Gly Leu Arg Gln Glu Met Ser Lys Asp Leu
            35                  40                  45

Glu Glu Val Lys Ala Lys Val Gln Pro Tyr Leu Asp Asp Phe Gln Lys
        50                  55                  60

Lys Trp Gln Glu Glu Met Glu Leu Tyr Arg Gln Lys Val Glu Pro Tyr
65                  70                  75                  80

Leu Asp Asp Phe Gln Lys Lys Trp Gln Glu Glu Met Glu Leu Tyr Arg
```

```
                     85                  90                  95
Gln Lys Val Glu Pro Leu Arg Ala Glu Leu Gln Glu Gly Ala Arg Gln
                100                 105                 110

Lys Leu His Glu Leu Gln Glu Lys Leu Ser Pro Leu Gly Glu Glu Met
            115                 120                 125

Arg Asp Arg Ala Arg Ala His Val Asp Ala Leu Arg Thr His Leu Ala
        130                 135                 140

Pro Tyr Ser Asp Glu Leu Arg Gln Arg Leu Ala Ala Arg Leu Glu Ala
145                 150                 155                 160

Leu Lys Glu Asn Gly Gly Ala Arg Leu Ala Glu Tyr His Ala Lys Ala
                165                 170                 175

Thr Glu His Leu Ser Thr Leu Ser Glu Lys Ala Lys Pro Ala Leu Glu
            180                 185                 190

Asp Leu Arg Gln Gly Leu Leu
            195

<210> SEQ ID NO 68
<211> LENGTH: 401
<212> TYPE: PRT
<213> ORGANISM: Artificial
<220> FEATURE:
<223> OTHER INFORMATION: MSP2N1

<400> SEQUENCE: 68

Met Gly His His His His His His Asp Tyr Asp Ile Pro Thr Thr
1               5                   10                  15

Glu Asn Leu Tyr Phe Gln Gly Ser Thr Phe Ser Lys Leu Arg Glu Gln
                20                  25                  30

Leu Gly Pro Val Thr Gln Glu Phe Trp Asp Asn Leu Glu Lys Glu Thr
            35                  40                  45

Glu Gly Leu Arg Gln Glu Met Ser Lys Asp Leu Glu Glu Val Lys Ala
        50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
                100                 105                 110

Leu Gly Glu Glu Met Arg Asp Arg Ala Arg Ala His Val Asp Ala Leu
            115                 120                 125

Arg Thr His Leu Ala Pro Tyr Ser Asp Glu Leu Arg Gln Arg Leu Ala
        130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln Gly Thr Phe Ser Lys Leu Arg Glu Gln Leu Gly Pro
        210                 215                 220

Val Thr Gln Glu Phe Trp Asp Asn Leu Glu Lys Glu Thr Glu Gly Leu
225                 230                 235                 240

Arg Gln Glu Met Ser Lys Asp Leu Glu Glu Val Lys Ala Lys Val Gln
```

-continued

```
                      245                 250                 255
Pro Tyr Leu Asp Asp Phe Gln Lys Lys Trp Gln Glu Glu Met Glu Leu
            260                 265                 270
Tyr Arg Gln Lys Val Glu Pro Leu Arg Ala Glu Leu Gln Glu Gly Ala
        275                 280                 285
Arg Gln Lys Leu His Glu Leu Gln Glu Lys Leu Ser Pro Leu Gly Glu
    290                 295                 300
Glu Met Arg Asp Arg Ala Arg Ala His Val Asp Ala Leu Arg Thr His
305                 310                 315                 320
Leu Ala Pro Tyr Ser Asp Glu Leu Arg Gln Arg Leu Ala Ala Arg Leu
                325                 330                 335
Glu Ala Leu Lys Glu Asn Gly Gly Ala Arg Leu Ala Glu Tyr His Ala
            340                 345                 350
Lys Ala Thr Glu His Leu Ser Thr Leu Ser Glu Lys Ala Lys Pro Ala
        355                 360                 365
Leu Glu Asp Leu Arg Gln Gly Leu Leu Pro Val Leu Glu Ser Phe Lys
    370                 375                 380
Val Ser Phe Leu Ser Ala Leu Glu Glu Tyr Thr Lys Lys Leu Asn Thr
385                 390                 395                 400
Gln

<210> SEQ ID NO 69
<211> LENGTH: 392
<212> TYPE: PRT
<213> ORGANISM: Artificial
<220> FEATURE:
<223> OTHER INFORMATION: MSP2N2

<400> SEQUENCE: 69

Met Gly His His His His His His Asp Tyr Asp Ile Pro Thr Thr
1               5                   10                  15
Glu Asn Leu Tyr Phe Gln Gly Ser Thr Phe Ser Lys Leu Arg Glu Gln
                20                  25                  30
Leu Gly Pro Val Thr Gln Glu Phe Trp Asp Asn Leu Glu Lys Glu Thr
            35                  40                  45
Glu Gly Leu Arg Gln Glu Met Ser Lys Asp Leu Glu Glu Val Lys Ala
        50                  55                  60
Lys Val Gln Pro Tyr Leu Asp Asp Phe Gln Lys Lys Trp Gln Glu Glu
65                  70                  75                  80
Met Glu Leu Tyr Arg Gln Lys Val Glu Pro Leu Arg Ala Glu Leu Gln
                85                  90                  95
Glu Gly Ala Arg Gln Lys Leu His Glu Leu Gln Glu Lys Leu Ser Pro
            100                 105                 110
Leu Gly Glu Glu Met Arg Asp Arg Ala Arg Ala His Val Asp Ala Leu
        115                 120                 125
Arg Thr His Leu Ala Pro Tyr Ser Asp Glu Leu Arg Gln Arg Leu Ala
    130                 135                 140
Ala Arg Leu Glu Ala Leu Lys Glu Asn Gly Gly Ala Arg Leu Ala Glu
145                 150                 155                 160
Tyr His Ala Lys Ala Thr Glu His Leu Ser Thr Leu Ser Glu Lys Ala
                165                 170                 175
Lys Pro Ala Leu Glu Asp Leu Arg Gln Gly Leu Leu Pro Val Leu Glu
            180                 185                 190
Ser Phe Lys Val Ser Phe Leu Ser Ala Leu Glu Glu Tyr Thr Lys Lys
        195                 200                 205
```

```
Leu Asn Thr Gln Gly Thr Pro Val Thr Gln Glu Phe Trp Asp Asn Leu
    210                 215                 220

Glu Lys Glu Thr Glu Gly Leu Arg Gln Glu Met Ser Lys Asp Leu Glu
225                 230                 235                 240

Glu Val Lys Ala Lys Val Gln Pro Tyr Leu Asp Asp Phe Gln Lys Lys
                245                 250                 255

Trp Gln Glu Glu Met Glu Leu Tyr Arg Gln Lys Val Glu Pro Leu Arg
                260                 265                 270

Ala Glu Leu Gln Glu Gly Ala Arg Gln Lys Leu His Glu Leu Gln Glu
                275                 280                 285

Lys Leu Ser Pro Leu Gly Glu Glu Met Arg Asp Arg Ala Arg Ala His
    290                 295                 300

Val Asp Ala Leu Arg Thr His Leu Ala Pro Tyr Ser Asp Glu Leu Arg
305                 310                 315                 320

Gln Arg Leu Ala Ala Arg Leu Glu Ala Leu Lys Glu Asn Gly Gly Ala
                325                 330                 335

Arg Leu Ala Glu Tyr His Ala Lys Ala Thr Glu His Leu Ser Thr Leu
                340                 345                 350

Ser Glu Lys Ala Lys Pro Ala Leu Glu Asp Leu Arg Gln Gly Leu Leu
    355                 360                 365

Pro Val Leu Glu Ser Phe Lys Val Ser Phe Leu Ser Ala Leu Glu Glu
    370                 375                 380

Tyr Thr Lys Lys Leu Asn Thr Gln
385                 390

<210> SEQ ID NO 70
<211> LENGTH: 381
<212> TYPE: PRT
<213> ORGANISM: Artificial
<220> FEATURE:
<223> OTHER INFORMATION: MSP2D1D1

<400> SEQUENCE: 70

Met Gly His His His His His His Asp Tyr Asp Ile Pro Thr Thr
1               5                   10                  15

Glu Asn Leu Tyr Phe Gln Gly Pro Val Thr Gln Glu Phe Trp Asp Asn
                20                  25                  30

Leu Glu Lys Glu Thr Glu Gly Leu Arg Gln Glu Met Ser Lys Asp Leu
            35                  40                  45

Glu Glu Val Lys Ala Lys Val Gln Pro Tyr Leu Asp Asp Phe Gln Lys
        50                  55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175
```

```
Leu Pro Val Leu Glu Ser Phe Lys Val Ser Phe Leu Ser Ala Leu Glu
            180                 185                 190

Glu Tyr Thr Lys Lys Leu Asn Thr Gln Gly Thr Pro Val Thr Gln Glu
        195                 200                 205

Phe Trp Asp Asn Leu Glu Lys Glu Thr Glu Gly Leu Arg Gln Glu Met
    210                 215                 220

Ser Lys Asp Leu Glu Glu Val Lys Ala Lys Val Gln Pro Tyr Leu Asp
225                 230                 235                 240

Asp Phe Gln Lys Lys Trp Gln Glu Glu Met Glu Leu Tyr Arg Gln Lys
                245                 250                 255

Val Glu Pro Leu Arg Ala Glu Leu Gln Glu Gly Ala Arg Gln Lys Leu
            260                 265                 270

His Glu Leu Gln Glu Lys Leu Ser Pro Leu Gly Glu Glu Met Arg Asp
        275                 280                 285

Arg Ala Arg Ala His Val Asp Ala Leu Arg Thr His Leu Ala Pro Tyr
    290                 295                 300

Ser Asp Glu Leu Arg Gln Arg Leu Ala Ala Arg Leu Glu Ala Leu Lys
305                 310                 315                 320

Glu Asn Gly Gly Ala Arg Leu Ala Glu Tyr His Ala Lys Ala Thr Glu
                325                 330                 335

His Leu Ser Thr Leu Ser Glu Lys Ala Lys Pro Ala Leu Glu Asp Leu
            340                 345                 350

Arg Gln Gly Leu Leu Pro Val Leu Glu Ser Phe Lys Val Ser Phe Leu
        355                 360                 365

Ser Ala Leu Glu Glu Tyr Thr Lys Lys Leu Asn Thr Gln
    370                 375                 380

<210> SEQ ID NO 71
<211> LENGTH: 603
<212> TYPE: DNA
<213> ORGANISM: Artificial
<220> FEATURE:
<223> OTHER INFORMATION: Nucleotide sequence encoding MSP1T4

<400> SEQUENCE: 71
atgggtcatc atcatcatca tcatcacgat tatgatattc ctactactga gaatttgtat    60
tttcagggtt ccgtgacgca ggaattctgg gacaacctgg aaaaagaaac cgagggactg   120
cgtcaggaaa tgtccaaaga tttagaagag gtgaaggcca aggttcagcc atatctcgat   180
gactttcaga aaaaatggca ggaagagatg gaattatatc gtcaaaaggt ggaaccgctg   240
cgtgcggaac tgcaagaggg ggcacgccaa aaactccatg agctccaaga gaagctcagc   300
ccattaggcg aagaaatgcg cgatcgcgcc cgtgcacatg ttgatgcact ccggactcat   360
ttggcgccgt attcggatga acttcgccag cgtttggccg cacgtctcga ggcgctgaaa   420
gaaaacgggg gtgcccgctt ggctgagtac acgcgaaaag cgacagaaca cctgagcacc   480
ttgagcgaaa aagcgaaacc ggcgctggaa gatctacgcc agggcttatt gcctgttctt   540
gagagcttta aagtcagttt tctgtcagct ctggaagaat atactaaaaa gctgaatacc   600
cag                                                                  603

<210> SEQ ID NO 72
<211> LENGTH: 570
<212> TYPE: DNA
<213> ORGANISM: Artificial
<220> FEATURE:
<223> OTHER INFORMATION: Nucleotide sequence encoding MSP1T5
```

```
<400> SEQUENCE: 72
atgggtcatc atcatcatca tcatcacgat tatgatattc ctactactga gaatttgtat    60
tttcagggta agaaaccga  gggactgcgt caggaaatgt ccaaagattt agaagaggtg   120
aaggccaagg ttcagccata tctcgatgac tttcagaaaa aatggcagga agagatggaa   180
ttatatcgtc aaaaggtgga accgctgcgt gcggaactgc aagaggggc  acgccaaaaa   240 ctccatgagc tccaagagaa gctcagccca ttaggcgaag aaatgcgcga tcgcgcccgt   300
gcacatgttg atgcactccg gactcatttg gcgccgtatt cggatgaact cgcgcagcgt   360
ttggccgcac gtctcgaggc gctgaaagaa acgggggtg  cccgcttggc tgagtaccac   420
gcgaaagcga cagaacacct gagcaccttg agcgaaaaag cgaaaccggc gctggaagat   480
ctacgccagg gcttattgcc tgttcttgag agctttaaag tcagttttct gtcagctctg   540
gaagaatata ctaaaaagct gaatacccag                                    570

<210> SEQ ID NO 73
<211> LENGTH: 603
<212> TYPE: DNA
<213> ORGANISM: Artificial
<220> FEATURE:
<223> OTHER INFORMATION: Nucleotide sequence encoding MSP1T6

<400> SEQUENCE: 73
atgggtcatc atcatcatca tcatcacgat tatgatattc ctactactga gaatttgtat    60
tttcagggtt ccgtgacgca ggaattctgg gacaacctgg aaaaagaaac cgagggactg   120
cgtcaggaaa tgtccaaaga tttagaagag gtgaaggcca aggttcagcc atatctcgat   180
gactttcaga aaaatggca  ggaagagatg gaattatatc gtcaaaaggt ggaaccgctg   240
cgtgcggaac tgcaagaggg ggcacgccaa aaactccatg agctccaaga agctcagc    300 ccattaggcg aagaaatgcg cgatcgcgcc cgtgcacatg ttgatgcact ccggactcat   360
ttggcgccgt attcggatga acttcgccag cgtttggccg cacgtctcga ggcgctgaaa   420
gaaaacgggg gtgcccgctt ggctgagtac cacgcgaaag cgacagaaca cctgagcacc   480
ttgagcgaaa aagcgaaacc ggcgctggaa gatctacgcc agggcttatt gcctgttctt   540
gagagcttta aagtcagttt tctgtcagct ctggaagaat atactaaaaa gctgaatacc   600
cag                                                                 603

<210> SEQ ID NO 74
<211> LENGTH: 597
<212> TYPE: DNA
<213> ORGANISM: Artificial
<220> FEATURE:
<223> OTHER INFORMATION: Nucleotide sequence encoding MSP1N1

<400> SEQUENCE: 74
atgggtcatc atcatcatca tcatcacgat tatgatattc ctactactga gaatttgtat    60
tttcagggtt ccgtgacgca ggaattctgg gacaacctgg aaaaagaaac cgagggactg   120
cgtcaggaaa tgtccaaaga tttagaagag gtgaaggcca aggttcagcc atatctcgat   180
gactttcaga aaaatggca  ggaagagatg gaattatatc gtcaaaaggt ggaaccatat   240
ctcgatgact tcagaaaaa  atggcaggaa gagatggaat tatatcgtca aaaggtggaa   300
ccgctgcgtg cggaactgca agaggggca  cgccaaaaac tccatgagct ccaagagaag   360
ctcagcccat taggcgaaga aatgcgcgat cgcgcccgtg cacatgttga tgcactccgg   420
```

```
actcatttgg cgccgtattc ggatgaactt cgccagcgtt tggccgcacg tctcgaggcg      480
ctgaaagaaa acggggtgc ccgcttggct gagtaccacg cgaaagcgac agaacacctg      540
agcaccttga gcgaaaaagc gaaaccggcg ctggaagatc tacgccaggg cttattg       597

<210> SEQ ID NO 75
<211> LENGTH: 867
<212> TYPE: DNA
<213> ORGANISM: Artificial
<220> FEATURE:
<223> OTHER INFORMATION: Nucleotide sequence encoding MSP1E3TEV

<400> SEQUENCE: 75
atgggtcatc atcatcatca tcatcacgat tatgatattc ctactactga gaatttgtat      60
tttcagggtc tgaagctgtt ggacaattgg gactctgtta cgtctacctt cagtaaactt     120
cgcgaacaac tgggccccgt gacgcaggaa ttctgggaca acctggaaaa agaaaccgag     180
ggactgcgtc aggaaatgtc aaagattta agaggtga aggccaaggt tcagccatat      240
ctcgatgact ttcagaaaaa atggcaggaa gagatggaat tatatcgtca aaaggtggaa     300
ccgctgcgtg cggaactgca gaggggca cgccaaaaac tccatgagct ccaagagaag     360
ctcagcccat taggcgaaga aatgcgcgat cgcgcccgtg cacatgttga tgcactccgg     420
actcatttgg cgccatatct cgatgacttt cagaaaaaat ggcaggaaga gatgaatta      480 tatcgtcaaa aggtggaacc gctgcgtgcg gaactgcaag aggggcacg ccaaaaactc     540 catgagctcc aagagaagct cagcccatta ggcgaagaaa tgcgcgatcg cgcccgtgca     600
catgttgatg cactccggac tcatttggcg ccgtattcgg atgaacttcg ccagcgtttg     660
gccgcacgtc tcgaggcgct gaaagaaaac ggggtgccc gcttggctga gtaccacgcg     720
aaagcgacag aacacctgag caccttgagc gaaaaagcga aaccggcgct ggaagatcta     780
cgccagggct tattgcctgt tcttgagagc tttaaagtca gttttctgtc agctctggaa     840
gaatatacta aaaagctgaa tacccag                                       867

<210> SEQ ID NO 76
<211> LENGTH: 834
<212> TYPE: DNA
<213> ORGANISM: Artificial
<220> FEATURE:
<223> OTHER INFORMATION: Nucleotide sequence encoding MSP1E3D1

<400> SEQUENCE: 76
atgggtcatc atcatcatca tcatcacgat tatgatattc ctactactga gaatttgtat      60
tttcagggtt ctaccttcag taaacttcgc gaacaactgg ccccgtgac gcaggaattc     120 tgggacaacc tggaaaaaga aaccgaggga ctgcgtcaga aatgtccaa agatttagaa     180 gaggtgaagg ccaaggttca gccatatctc gatgactttc agaaaaatg caggaagag      240 atggaattat atcgtcaaaa ggtggaaccg ctgcgtgcgg aactgcaaga gggggcacgc    300
caaaaactcc atgagctcca agagaagctc agcccattag gcgaagaaat gcgcgatcgc    360
gcccgtgcac atgttgatgc actccggact catttggcgc catatctcga tgactttcag    420
aaaaaatggc aggaagagat ggaattatat cgtcaaaagg tggaaccgct gcgtgcggaa    480
ctgcaagagg ggcacgcca aaaactccat gagctccaag agaagctcag cccattaggc    540
gaagaaatgc gcgatcgcgc ccgtgcacat gttgatgcac tccggactca tttggcgccg   600
tattcggatg aacttcgcca gcgtttggcc gcacgtctcg aggcgctgaa agaaaacggg   660
ggtgcccgct tggctgagta ccacgcgaaa gcgacagaac acctgagcac cttgagcgaa   720
```

```
aaagcgaaac cggcgctgga agatctacgc cagggcttat tgcctgttct tgagagcttt      780
aaagtcagtt ttctgtcagc tctggaagaa tatactaaaa agctgaatac ccag            834
```

<210> SEQ ID NO 77
<211> LENGTH: 1275
<212> TYPE: DNA
<213> ORGANISM: Artificial
<220> FEATURE:
<223> OTHER INFORMATION: Nucleotide sequence encoding MSP2TEV

<400> SEQUENCE: 77

```
atgggtcatc atcatcatca tcatcacgat tatgatattc ctactactga aatttgtat       60 tttcagggtc taaagctcct tgacaactgg gacagcgtga cctccacctt cagcaagctg     120
cgcgaacagc tcggccctgt gacccaggag ttctgggata acctggaaaa ggagacagag     180
ggcctgaggc aggagatgag caaggatctg gaggaggtga aggccaaggt gcagccctac     240
ctggacgact tccagaagaa gtggcaggag gagatggagc tctaccgcca gaaggtggag     300
ccgctgcgcg cagagctcca agagggcgcg cgccagaagc tgcacgagct gcaagagaag     360
ctgagcccac tgggcgagga gatgcgcgac cgcgcgcgcg cccatgtgga cgcgctgcgc     420
acgcatctgg cccctacag cgacgagctg cgccagcgct tggccgcgcg ccttgaggct      480
ctcaaggaga acggcggcgc cagactggcc gagtaccacg ccaaggccac cgagcatctg     540
agcacgctca gcgagaaggc caagcccgcg ctcgaggacc tccgccaagg cctgctgccc     600
gtgctggaga gcttcaaggt cagcttcctg agcgctctcg aggagtacac taagaagctc     660
aacacccagg gtaccctaaa gctccttgac aactgggaca gcgtgacctc caccttcagc     720
aagctgcgcg aacagctcgg ccctgtgacc caggagttct gggataacct ggaaaaggag     780
acagagggcc tgaggcagga gatgagcaag gatctggagg aggtgaaggc caaggtgcag     840
ccctacctgg acgacttcca gaagaagtgg caggaggaga tggagctcta ccgccagaag     900
gtggagccgc tgcgcgcaga gctccaagag ggcgcgcgcc agaagctgca cgagctgcaa     960
gagaagctga gcccactggg cgaggagatg cgcgaccgcg cgcgcgccca tgtggacgcg    1020
ctgcgcacgc atctggcccc ctacagcgac gagctgcgcc agcgcttggc cgcgcgcctt    1080
gaggctctca aggagaacgg cggcgccaga ctggccgagt accacgccaa ggccaccgag    1140
catctgagca cgctcagcga gaaggccaag cccgcgctcg aggacctccg ccaaggcctg    1200
ctgcccgtgc tggagagctt caaggtcagc ttcctgagcg ctctcgagga gtacactaag    1260
aagctcaaca cccag                                                     1275
```

<210> SEQ ID NO 78
<211> LENGTH: 1203
<212> TYPE: DNA
<213> ORGANISM: Artificial
<220> FEATURE:
<223> OTHER INFORMATION: Nucleotide sequence encoding MSP2N1

<400> SEQUENCE: 78

```
atgggtcatc atcatcatca tcatcacgat tatgatattc ctactactga aatttgtat       60 tttcagggtt ctaccttcag taaacttcgc gaacaactgg gccccgtgac gcaggaattc     120
tgggacaacc tggaaaaaga aaccgaggga ctgcgtcagg aaatgtccaa agatttagaa     180
gaggtgaagg ccaaggttca gccatatctc gatgactttc agaaaaaatg gcaggaagag     240
atggaattat atcgtcaaaa ggtggaaccg ctgcgtgcgg aactgcaaga gggggcacgc     300
```

```
caaaaactcc atgagctcca agagaagctc agcccattag gcgaagaaat gcgcgatcgc    360
gcccgtgcac atgttgatgc actccggact catttggcgc cgtattcgga tgaacttcgc    420
cagcgtttgg ccgcacgtct cgaggcgctg aaagaaaacg ggggtgcccg cttggctgag    480
taccacgcga aagcgacaga acacctgagc accttgagcg aaaaagcgaa accggcgctg    540
gaagatctac gccagggctt attgcctgtt cttgagagct ttaaagtcag ttttctgtca    600
gctctggaag aatatactaa aaagctgaat acccagggta ccttcagtaa acttcgcgaa    660
caactgggcc ccgtgacgca ggaattctgg gacaacctgg aaaaagaaac cgagggactg    720
cgtcaggaaa tgtccaaaga tttagaagag gtgaaggcca aggttcagcc atatctcgat    780
gactttcaga aaaatggcag gaagagatgg aattatatc gtcaaaaggt ggaaccgctg    840
cgtgcgaac tgcaagaggg ggcacgccaa aaactccatg agctccaaga aagctcagc    900
ccattaggcg aagaaatgcg cgatcgcgcc cgtgcacatg ttgatgcact ccggactcat    960
ttggcgccgt attcgatga acttcgccag cgtttggccg cacgtctcga ggcgctgaaa   1020
gaaaacgggg gtgcccgctt ggctgagtac cacgcgaaag cgacagaaca cctgagcacc   1080
ttgagcgaaa aagcgaaacc ggcgctggaa gatctacgcc agggcttatt gcctgttctt   1140
gagagcttta agtcagtttt ctgtcagct ctggaagaat atactaaaaa gctgaatacc   1200
cag                                                                 1203

<210> SEQ ID NO 79
<211> LENGTH: 1176
<212> TYPE: DNA
<213> ORGANISM: Artificial
<220> FEATURE:
<223> OTHER INFORMATION: Nucleotide sequence encoding MSP2N2

<400> SEQUENCE: 79
atgggtcatc atcatcatca tcatcacgat tatgatattc ctactactga gaatttgtat     60
tttcagggtt ctaccttcag taaacttcgc gaacaactgg gccccgtgac gcaggaattc    120
tgggacaacc tggaaaaaga aaccgaggga ctgcgtcagg aaatgtccaa agatttagaa    180
gaggtgaagg ccaaggttca gccatatctc gatgactttc agaaaaatgg caggaagag    240
atggaattat atcgtcaaaa ggtggaaccg ctgcgtgcgg aactgcaaga ggggggcacgc    300
caaaaactcc atgagctcca agagaagctc agcccattag gcgaagaaat gcgcgatcgc    360
gcccgtgcac atgttgatgc actccggact catttggcgc cgtattcgga tgaacttcgc    420
cagcgtttgg ccgcacgtct cgaggcgctg aaagaaaacg ggggtgcccg cttggctgag    480
taccacgcga aagcgacaga acacctgagc accttgagcg aaaaagcgaa accggcgctg    540
gaagatctac gccagggctt attgcctgtt cttgagagct ttaaagtcag ttttctgtca    600
gctctggaag aatatactaa aaagctgaat acccagggta cccccgtgac gcaggaattc    660
tgggacaacc tggaaaaaga aaccgaggga ctgcgtcagg aaatgtccaa agatttagaa    720
gaggtgaagg ccaaggttca gccatatctc gatgactttc agaaaaatgg caggaagag    780
atggaattat atcgtcaaaa ggtggaaccg ctgcgtgcgg aactgcaaga ggggggcacgc    840
caaaaactcc atgagctcca agagaagctc agcccattag gcgaagaaat gcgcgatcgc    900
gcccgtgcac atgttgatgc actccggact catttggcgc cgtattcgga tgaacttcgc    960
cagcgtttgg ccgcacgtct cgaggcgctg aaagaaaacg ggggtgcccg cttggctgag   1020
taccacgcga aagcgacaga acacctgagc accttgagcg aaaaagcgaa accggcgctg   1080
gaagatctac gccagggctt attgcctgtt cttgagagct ttaaagtcag ttttctgtca   1140
```

```
gctctggaag aatatactaa aaagctgaat acccag                              1176
```

<210> SEQ ID NO 80
<211> LENGTH: 1198
<212> TYPE: DNA
<213> ORGANISM: Artificial
<220> FEATURE:
<223> OTHER INFORMATION: Nucleotide sequence encoding MSP2N3

<400> SEQUENCE: 80

```
atgggtcatc atcatcatca tcatcacgat tatgatattc ctactactga gaatttgtat      60
tttcagggtt ctaccttcag taaacttcgc gaacaactgg gccccgtgac gcaggaattc     120
tgggacaacc tggaaaaaga aaccgaggga ctgcgtcagg aaatgtccaa agatttagaa     180
gaggtgaagg ccaaggttca gccatatctc gatgactttc agaaaaaatg gcaggaagag     240
atggaattat atcgtcaaaa ggtggaaccg ctgcgtgcgg aactgcaaga gggggcacgc     300
caaaaactcc atgagctcca agagaagctc agcccattag gcgaagaaat gcgcgatcgc     360
gcccgtgcac atgttgatgc actccggact catttggcgc cgtattcgga tgaacttcgc     420
cagcgtttgg ccgcacgtct cgaggcgctg aaagaaaacg ggggtgcccg cttggctgag     480
taccacgcga aagcgacaga cacctgagc accttgagcg aaaaagcgaa accggcgctg     540
gaagatctac gccagggctt attgcctgtt cttgagagct ttaaagtcag ttttctgtca     600
gctctggaag aatatactaa aaagctgaat acccaggta cccgcgaaca actgggcccc     660
gtgacgcagg aattctggga caacctggaa aaagaaaccg agggactgcg tcaggaaatg     720
tccaaagatt tagaagaggt gaaggccaag gttcagccat atctcgatga ctttcagaaa     780
aaatggcagg aagagatgga attatatcgt caaaaggtgg aaccgctgcg tgcggaactg     840
caagaggggg cacgccaaaa actccatgag ctccaagaga agctcagccc attaggcgaa     900
gaaatgcgcg atcgcgcccg tgcacatgtt gatgcactcc ggactcattt ggcgccgtat     960
tcggatgaac ttcgccagcg tttggccgca cgtctcgagg cgctgaaaga aaacgggggt    1020
gcccgcttgg ctgagtacca cgcgaaagcg acagaacacc tgagcacctt gagcgaaaaa    1080
gcgaaaccgg cgctggaaga tctacgccag ggcttattgc ctgttcttga gctttaaa    1140
gtcagttttc tgtcagctct ggaagaatat actaaaaagc tgaatacccc gtaagctt     1198
```

<210> SEQ ID NO 81
<211> LENGTH: 397
<212> TYPE: PRT
<213> ORGANISM: Artificial
<220> FEATURE:
<223> OTHER INFORMATION: MSP2N3

<400> SEQUENCE: 81

```
Met Gly His His His His His His Asp Tyr Asp Ile Pro Thr Thr
1               5                   10                  15

Glu Asn Leu Tyr Phe Gln Gly Ser Thr Phe Ser Lys Leu Arg Glu Gln
                20                  25                  30

Leu Gly Pro Val Thr Gln Glu Phe Trp Asp Asn Leu Glu Lys Glu Thr
            35                  40                  45

Glu Gly Leu Arg Gln Glu Met Ser Lys Asp Leu Glu Glu Val Lys Ala
        50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
```

```
                85                  90                  95
Glu Gly Ala Arg Gln Lys Leu His Glu Leu Gln Glu Lys Leu Ser Pro
            100                 105                 110
Leu Gly Glu Glu Met Arg Asp Arg Ala Arg Ala His Val Asp Ala Leu
            115                 120                 125
Arg Thr His Leu Ala Pro Tyr Ser Asp Glu Leu Arg Gln Arg Leu Ala
            130                 135                 140
Ala Arg Leu Glu Ala Leu Lys Glu Asn Gly Gly Ala Arg Leu Ala Glu
145                 150                 155                 160
Tyr His Ala Lys Ala Thr Glu His Leu Ser Thr Leu Ser Glu Lys Ala
                165                 170                 175
Lys Pro Ala Leu Glu Asp Leu Arg Gln Gly Leu Leu Pro Val Leu Glu
            180                 185                 190
Ser Phe Lys Val Ser Phe Leu Ser Ala Leu Glu Glu Tyr Thr Lys Lys
            195                 200                 205
Leu Asn Thr Gln Gly Thr Arg Glu Gln Leu Gly Pro Val Thr Gln Glu
            210                 215                 220
Phe Trp Asp Asn Leu Glu Lys Glu Thr Glu Gly Leu Arg Gln Glu Met
225                 230                 235                 240
Ser Lys Asp Leu Glu Glu Val Lys Ala Lys Val Gln Pro Tyr Leu Asp
                245                 250                 255
Asp Phe Gln Lys Lys Trp Gln Glu Glu Met Glu Leu Tyr Arg Gln Lys
            260                 265                 270
Val Glu Pro Leu Arg Ala Glu Leu Gln Glu Gly Ala Arg Gln Lys Leu
            275                 280                 285
His Glu Leu Gln Glu Lys Leu Ser Pro Leu Gly Glu Glu Met Arg Asp
            290                 295                 300
Arg Ala Arg Ala His Val Asp Ala Leu Arg Thr His Leu Ala Pro Tyr
305                 310                 315                 320
Ser Asp Glu Leu Arg Gln Arg Leu Ala Ala Arg Leu Glu Ala Leu Lys
                325                 330                 335
Glu Asn Gly Gly Ala Arg Leu Ala Glu Tyr His Ala Lys Ala Thr Glu
            340                 345                 350
His Leu Ser Thr Leu Ser Glu Lys Ala Lys Pro Ala Leu Glu Asp Leu
            355                 360                 365
Arg Gln Gly Leu Leu Pro Val Leu Glu Ser Phe Lys Val Ser Phe Leu
            370                 375                 380
Ser Ala Leu Glu Glu Tyr Thr Lys Lys Leu Asn Thr Gln
385                 390                 395

<210> SEQ ID NO 82
<211> LENGTH: 1149
<212> TYPE: DNA
<213> ORGANISM: Artificial
<220> FEATURE:
<223> OTHER INFORMATION: Nucleotide sequence encoding MSP2N4

<400> SEQUENCE: 82
atgggtcatc atcatcatca tcatcacgat tatgatattc ctactactga gaatttgtat      60
tttcagggtt ccgtgacgca ggaattctgg gacaacctgg aaaaagaaac cgagggactg     120
cgtcaggaaa tgtccaaaga tttagaagag gtgaaggcca aggttcagcc atatctcgat     180
gactttcaga aaaaatggca ggaagagatg gaattatatc gtcaaaaggt ggaaccgctg     240
cgtgcggaac tgcaagaggg ggcacgccaa aaactccatg agctccaaga gaagctcagc     300
```

-continued

```
ccattaggcg aagaaatgcg cgatcgcgcc cgtgcacatg ttgatgcact ccggactcat    360
ttggcgccgt attcggatga acttcgccag cgtttggccg cacgtctcga ggcgctgaaa    420
gaaaacgggg gtgcccgctt ggctgagtac cacgcgaaag cgacagaaca cctgagcacc    480
ttgagcgaaa aagcgaaacc ggcgctggaa gatctacgcc agggcttatt gcctgttctt    540
gagagcttta aagtcagttt tctgtcagct ctggaagaat atactaaaaa gctgaatacc    600
cagaatccag gtaccccgt gacgcaggaa ttctgggaca acctgaaaa agaaaccgag      660
ggactgcgtc aggaaatgtc caaagattta gagaggtga aggccaaggt tcagccatat     720
ctcgatgact ttcagaaaaa atggcaggaa gagatgaat tatatcgtca aaaggtggaa      780
ccgctgcgtg cggaactgca gagggggca cgccaaaaac tccatgagct ccaagagaag     840
ctcagcccat taggcgaaga aatgcgcgat cgcgcccgtg cacatgttga tgcactccgg    900
actcatttgg cgccgtattc ggatgaactt cgccagcgtt tggccgcacg tctcgaggcg    960
ctgaaagaaa acggggtgc cgcttggct gagtaccacg cgaaagcgac agaacacctg     1020
agcaccttga gcgaaaaagc gaaaccggcg ctggaagatc tacgccaggg cttattgcct   1080
gttcttgaga gctttaaagt cagttttctg tcagctctgg aagaatatac taaaaagctg   1140
aatacccag                                                           1149
```

<210> SEQ ID NO 83
<211> LENGTH: 383
<212> TYPE: PRT
<213> ORGANISM: Artificial
<220> FEATURE:
<223> OTHER INFORMATION: MSP2N4

<400> SEQUENCE: 83

```
Met Gly His His His His His His Asp Tyr Asp Ile Pro Thr Thr
1               5                   10                  15

Glu Asn Leu Tyr Phe Gln Gly Ser Val Thr Gln Glu Phe Trp Asp Asn
            20                  25                  30

Leu Glu Lys Glu Thr Glu Gly Leu Arg Gln Glu Met Ser Lys Asp Leu
        35                  40                  45

Glu Glu Val Lys Ala Lys Val Gln Pro Tyr Leu Asp Asp Phe Gln Lys
    50                  55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln Asn Pro Gly Thr Pro Val Thr
        195                 200                 205
```

```
Gln Glu Phe Trp Asp Asn Leu Glu Lys Glu Thr Gly Leu Arg Gln
    210                 215                 220

Glu Met Ser Lys Asp Leu Glu Glu Val Lys Ala Lys Val Gln Pro Tyr
225                 230                 235                 240

Leu Asp Asp Phe Gln Lys Lys Trp Gln Glu Glu Met Glu Leu Tyr Arg
                245                 250                 255

Gln Lys Val Glu Pro Leu Arg Ala Glu Leu Gln Glu Gly Ala Arg Gln
                260                 265                 270

Lys Leu His Glu Leu Gln Glu Lys Leu Ser Pro Leu Gly Glu Glu Met
            275                 280                 285

Arg Asp Arg Ala Arg Ala His Val Asp Ala Leu Arg Thr His Leu Ala
    290                 295                 300

Pro Tyr Ser Asp Glu Leu Arg Gln Arg Leu Ala Ala Arg Leu Glu Ala
305                 310                 315                 320

Leu Lys Glu Asn Gly Gly Ala Arg Leu Ala Glu Tyr His Ala Lys Ala
                325                 330                 335

Thr Glu His Leu Ser Thr Leu Ser Glu Lys Ala Lys Pro Ala Leu Glu
            340                 345                 350

Asp Leu Arg Gln Gly Leu Leu Pro Val Leu Glu Ser Phe Lys Val Ser
    355                 360                 365

Phe Leu Ser Ala Leu Glu Glu Tyr Thr Lys Lys Leu Asn Thr Gln
370                 375                 380

<210> SEQ ID NO 84
<211> LENGTH: 1137
<212> TYPE: DNA
<213> ORGANISM: Artificial
<220> FEATURE:
<223> OTHER INFORMATION: Nucleotide sequence encoding MSP2N5

<400> SEQUENCE: 84
atgggtcatc atcatcatca tcatcacgat tatgatattc ctactactga gaatttgtat      60
tttcagggtt ccgtgacgca ggaattctgg gacaacctgg aaaagaaaac cgagggactg     120
cgtcaggaaa tgtccaaaga tttagaagag gtgaaggcca aggttcagcc atatctcgat     180
gactttcaga aaaaatggca ggaagagatg gaattatatc gtcaaaaggt ggaaccatat     240
ctcgatgact tcagaaaaaa tggcaggaa gagatggaat tatatcgtca aaaggtggaa     300
ccgctgcgtg cggaactgca gagggggca cgccaaaaac tccatgagct ccaagagaag     360
ctcagcccat taggcgaaga atgcgcgat cgcgcccgtg cacatgttga tgcactccgg     420
actcatttgg cgccgtattc ggatgaactt cgccagcgtt tggccgcacg tctcgaggcg     480
ctgaaagaaa acggggtgc cgcttggct gagtaccacg cgaaagcgac agaacacctg     540
agcaccttga gcgaaaaagc gaaaccggcg ctggaagatc tacgccaggg cttattgaat     600
ccaggtacca agatttaga agaggtgaag gccaaggttc agccatatct cgatgacttt     660
cagaaaaaat ggcaggaaga gatggaatta tatcgtcaaa aggtggaacc atatctcgat     720
gactttcaga aaaaatggca ggaagagatg gaattatatc gtcaaaaggt ggaaccgctg     780
cgtgcggaac tgcaagaggg ggcacgccaa aaactccatg agctccaaga gaagctcagc     840
ccattaggcg aagaatgcg cgatcgcgcc cgtgcacatg ttgatgcact ccggactcat     900
ttggcgccgt attcggatga acttcgccag cgtttggccg cacgtctcga ggcgctgaaa     960
gaaaacgggg gtgcccgctt ggctgagtac acgcgaaag cgacagaaca cctgagcacc    1020
ttgagcgaaa aagcgaaacc ggcgctggaa gatctacgcc agggcttatt gcccgtgacg    1080
```
caggaattct gggacaacct ggaaaaagaa accgagggac tgcgtcagga aatgtcc    1137

<210> SEQ ID NO 85
<211> LENGTH: 379
<212> TYPE: PRT
<213> ORGANISM: Artificial
<220> FEATURE:
<223> OTHER INFORMATION: MSP2N5

<400> SEQUENCE: 85

Met Gly His His His His His His Asp Tyr Asp Ile Pro Thr Thr
1               5                   10                  15

Glu Asn Leu Tyr Phe Gln Gly Ser Val Thr Gln Glu Phe Trp Asp Asn
                20                  25                  30

Leu Glu Lys Glu Thr Glu Gly Leu Arg Gln Glu Met Ser Lys Asp Leu
            35                  40                  45

Glu Glu Val Lys Ala Lys Val Gln Pro Tyr Leu Asp Asp Phe Gln Lys
        50                  55                  60

Lys Trp Gln Glu Glu Met Glu Leu Tyr Arg Gln Lys Val Glu Pro Tyr
65                  70                  75                  80

Leu Asp Asp Phe Gln Lys Lys Trp Gln Glu Glu Met Glu Leu Tyr Arg
                85                  90                  95

Gln Lys Val Glu Pro Leu Arg Ala Glu Leu Gln Glu Gly Ala Arg Gln
            100                 105                 110

Lys Leu His Glu Leu Gln Glu Lys Leu Ser Pro Leu Gly Glu Glu Met
        115                 120                 125

Arg Asp Arg Ala Arg Ala His Val Asp Ala Leu Arg Thr His Leu Ala
130                 135                 140

Pro Tyr Ser Asp Glu Leu Arg Gln Arg Leu Ala Ala Arg Leu Glu Ala
145                 150                 155                 160

Leu Lys Glu Asn Gly Gly Ala Arg Leu Ala Glu Tyr His Ala Lys Ala
                165                 170                 175

Thr Glu His Leu Ser Thr Leu Ser Glu Lys Ala Lys Pro Ala Leu Glu
            180                 185                 190

Asp Leu Arg Gln Gly Leu Leu Asn Pro Gly Thr Lys Asp Leu Glu Glu
        195                 200                 205

Val Lys Ala Lys Val Gln Pro Tyr Leu Asp Asp Phe Gln Lys Lys Trp
    210                 215                 220

Gln Glu Glu Met Glu Leu Tyr Arg Gln Lys Val Glu Pro Tyr Leu Asp
225                 230                 235                 240

Asp Phe Gln Lys Lys Trp Gln Glu Glu Met Glu Leu Tyr Arg Gln Lys
                245                 250                 255

Val Glu Pro Leu Arg Ala Glu Leu Gln Glu Gly Ala Arg Gln Lys Leu
            260                 265                 270

His Glu Leu Gln Glu Lys Leu Ser Pro Leu Gly Glu Glu Met Arg Asp
        275                 280                 285

Arg Ala Arg Ala His Val Asp Ala Leu Arg Thr His Leu Ala Pro Tyr
    290                 295                 300

Ser Asp Glu Leu Arg Gln Arg Leu Ala Ala Arg Leu Glu Ala Leu Lys
305                 310                 315                 320

Glu Asn Gly Gly Ala Arg Leu Ala Glu Tyr His Ala Lys Ala Thr Glu
                325                 330                 335

His Leu Ser Thr Leu Ser Glu Lys Ala Lys Pro Ala Leu Glu Asp Leu
            340                 345                 350

Arg Gln Gly Leu Leu Pro Val Thr Gln Glu Phe Trp Asp Asn Leu Glu

```
                    355                 360                 365
Lys Glu Thr Glu Gly Leu Arg Gln Glu Met Ser
    370                 375

<210> SEQ ID NO 86
<211> LENGTH: 1143
<212> TYPE: DNA
<213> ORGANISM: Artificial
<220> FEATURE:
<223> OTHER INFORMATION: Nucleotide sequence encoding MSP2N6

<400> SEQUENCE: 86
atgggtcatc atcatcatca tcatcacgat tatgatattc ctactactga gaatttgtat      60
tttcagggtt ccgtgacgca ggaattctgg gacaacctgg aaaaagaaac cgagggactg     120
cgtcaggaaa tgtccaaaga tttagaagag gtgaaggcca aggttcagcc atatctcgat     180
gactttcaga aaaaatggca ggaagagatg gaattatatc gtcaaaaggt ggaaccatat     240
ctcgatgact tcagaaaaa atggcaggaa gagatggaat tatatcgtca aaaggtggaa     300
ccgctgcgtg cggaactgca gaggggca cgccaaaaac tccatgagct ccaagagaag     360
ctcagcccat taggcgaaga aatgcgcgat cgcgcccgtg cacatgttga tgcactccgg     420
actcatttgg cgccgtattc ggatgaactt cgccagcgtt tggccgcacg tctcgaggcg     480
ctgaaagaaa cgggggtgc ccgcttggct gagtaccacg cgaaagcgac agaacacctg     540
agcaccttga cgaaaaagc gaaaccggcg ctggaagatc tacgccaggg cttattgtcc     600
aatccaggta cccaaaaaga tttagaagag gtgaaggcca aggttcagcc atatctcgat     660
gactttcaga aaaaatggca ggaagagatg gaattatatc gtcaaaaggt ggaaccatat     720
ctcgatgact tcagaaaaa atggcaggaa gagatggaat tatatcgtca aaaggtggaa     780
ccgctgcgtg cggaactgca gaggggca cgccaaaaac tccatgagct ccaagagaag     840
ctcagcccat taggcgaaga aatgcgcgat cgcgcccgtg cacatgttga tgcactccgg     900
actcatttgg cgccgtattc ggatgaactt cgccagcgtt tggccgcacg tctcgaggcg     960
ctgaaagaaa cgggggtgc ccgcttggct gagtaccacg cgaaagcgac agaacacctg    1020
agcaccttga gcgaaaaagc gaaaccggcg ctggaagatc tacgccaggg cttattgccc    1080
gtgacgcagg aattctggga caacctggaa aagaaaccg agggactgcg tcaggaaatg    1140
tcc                                                                  1143

<210> SEQ ID NO 87
<211> LENGTH: 381
<212> TYPE: PRT
<213> ORGANISM: Artificial
<220> FEATURE:
<223> OTHER INFORMATION: MSP2N6

<400> SEQUENCE: 87

Met Gly His His His His His His Asp Tyr Asp Ile Pro Thr Thr
1               5                   10                  15

Glu Asn Leu Tyr Phe Gln Gly Ser Val Thr Gln Glu Phe Trp Asp Asn
            20                  25                  30

Leu Glu Lys Glu Thr Glu Gly Leu Arg Gln Glu Met Ser Lys Asp Leu
        35                  40                  45

Glu Glu Val Lys Ala Lys Val Gln Pro Tyr Leu Asp Asp Phe Gln Lys
    50                  55                  60

Lys Trp Gln Glu Glu Met Glu Leu Tyr Arg Gln Lys Val Glu Pro Tyr
65                  70                  75                  80
```

Leu Asp Asp Phe Gln Lys Lys Trp Gln Glu Glu Met Glu Leu Tyr Arg
                85                  90                  95
Gln Lys Val Glu Pro Leu Arg Ala Glu Leu Gln Glu Gly Ala Arg Gln
            100                 105                 110
Lys Leu His Glu Leu Gln Glu Lys Leu Ser Pro Leu Gly Glu Glu Met
        115                 120                 125
Arg Asp Arg Ala Arg Ala His Val Asp Ala Leu Arg Thr His Leu Ala
    130                 135                 140
Pro Tyr Ser Asp Glu Leu Arg Gln Arg Leu Ala Ala Arg Leu Glu Ala
145                 150                 155                 160
Leu Lys Glu Asn Gly Gly Ala Arg Leu Ala Glu Tyr His Ala Lys Ala
                165                 170                 175
Thr Glu His Leu Ser Thr Leu Ser Glu Lys Ala Lys Pro Ala Leu Glu
            180                 185                 190
Asp Leu Arg Gln Gly Leu Leu Ser Asn Pro Gly Thr Gln Lys Asp Leu
        195                 200                 205
Glu Glu Val Lys Ala Lys Val Gln Pro Tyr Leu Asp Asp Phe Gln Lys
    210                 215                 220
Lys Trp Gln Glu Glu Met Glu Leu Tyr Arg Gln Lys Val Glu Pro Tyr
225                 230                 235                 240
Leu Asp Asp Phe Gln Lys Lys Trp Gln Glu Glu Met Glu Leu Tyr Arg
                245                 250                 255
Gln Lys Val Glu Pro Leu Arg Ala Glu Leu Gln Glu Gly Ala Arg Gln
            260                 265                 270
Lys Leu His Glu Leu Gln Glu Lys Leu Ser Pro Leu Gly Glu Glu Met
        275                 280                 285
Arg Asp Arg Ala Arg Ala His Val Asp Ala Leu Arg Thr His Leu Ala
    290                 295                 300
Pro Tyr Ser Asp Glu Leu Arg Gln Arg Leu Ala Ala Arg Leu Glu Ala
305                 310                 315                 320
Leu Lys Glu Asn Gly Gly Ala Arg Leu Ala Glu Tyr His Ala Lys Ala
                325                 330                 335
Thr Glu His Leu Ser Thr Leu Ser Glu Lys Ala Lys Pro Ala Leu Glu
            340                 345                 350
Asp Leu Arg Gln Gly Leu Leu Pro Val Thr Gln Glu Phe Trp Asp Asn
        355                 360                 365
Leu Glu Lys Glu Thr Glu Gly Leu Arg Gln Glu Met Ser
    370                 375                 380

<210> SEQ ID NO 88
<211> LENGTH: 636
<212> TYPE: DNA
<213> ORGANISM: Artificial
<220> FEATURE:
<223> OTHER INFORMATION: Nucleotide sequence encoding MSP1RC12'

<400> SEQUENCE: 88
atgggtcatc atcatcatca tcacattgag ggatgtctga agctgttgga caattgggac      60
tctgttacgt ctaccttcag taaacttcgc gaacaactgg ccccgtgac gcaggaattc      120 tgggacaacc tggaaaaaga aaccgaggga ctgcgtcagg aaatgtccaa agatttagaa      180
gaggtgaagg ccaaggttca gccatatctc gatgactttc agaaaaaatg gcaggaagag      240
atggaattat atcgtcaaaa ggtggaaccg ctgcgtgcgg aactgcaaga gggggcacgc      300
caaaaactcc atgagctcca agagaagctc agcccattag gcgaagaaat gcgcgatcgc      360

```
gcccgtgcac atgttgatgc actccggact catttggcgc cgtattcgga tgaacttcgc    420
cagcgtttgg ccgcacgtct cgaggcgctg aaagaaaacg ggggtgcccg cttggctgag    480
taccacgcga aagcgacaga cacctgagcc accttgagcg aaaaagcgaa accggcgctg    540
gaagatctac gccagggctt attgcctgtt cttgagagct ttaaagtcag tttctgtca     600 gctctggaag aatatactaa aaagctgaat acccag                              636
```

<210> SEQ ID NO 89
<211> LENGTH: 212
<212> TYPE: PRT
<213> ORGANISM: Artificial
<220> FEATURE:
<223> OTHER INFORMATION: MSP1RC12'

<400> SEQUENCE: 89

```
Met Gly His His His His His His Ile Glu Gly Cys Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln
    210
```

<210> SEQ ID NO 90
<211> LENGTH: 636
<212> TYPE: DNA
<213> ORGANISM: Artificial
<220> FEATURE:
<223> OTHER INFORMATION: Nucleotide sequence encoding MSP1K90C

<400> SEQUENCE: 90

```
atgggtcatc atcatcatca tcacattgag gacgtctga agctgttgga caattgggac     60
tctgttacgt ctaccttcag taaacttcgc gaacaactgg ccccgtgac gcaggaattc    120 tgggacaacc tggaaaaaga aaccgaggga ctgcgtcagg aaatgtccaa agatttagaa   180
```

```
gaggtgaagg ccaaggttca gccatatctc gatgactttc agaaaaaatg gcaggaagag    240
atggaattat atcgtcaaaa ggtggaaccg ctgcgtgcgg aactgcaaga gggggcacgc    300
caatgtctcc atgagctcca agagaagctc agcccattag gcgaagaaat gcgcgatcgc    360
gcccgtgcac atgttgatgc actccggact catttggcgc cgtattcgga tgaacttcgc    420
cagcgtttgg ccgcacgtct cgaggcgctg aaagaaaacg ggggtgcccg cttggctgag    480
taccacgcga aagcgacaga acacctgagc accttgagcg aaaaagcgaa accggcgctg    540
gaagatctac gccagggctt attgcctgtt cttgagagct ttaaagtcag ttttctgtca    600
gctctggaag aatatactaa aaagctgaat acccag                              636
```

<210> SEQ ID NO 91
<211> LENGTH: 212
<212> TYPE: PRT
<213> ORGANISM: Artificial
<220> FEATURE:
<223> OTHER INFORMATION: MSP1K90C

<400> SEQUENCE: 91

```
Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Cys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln
    210
```

<210> SEQ ID NO 92
<211> LENGTH: 636
<212> TYPE: DNA
<213> ORGANISM: Artificial
<220> FEATURE:
<223> OTHER INFORMATION: Nucleotide sequence encoding MSP1K152C

<400> SEQUENCE: 92

```
atgggtcatc atcatcatca tcacattgag gacgtctga agctgttgga caattgggac    60
```

-continued

```
tctgttacgt ctaccttcag taaacttcgc gaacaactgg gccccgtgac gcaggaattc    120
tgggacaacc tggaaaaaga aaccgaggga ctgcgtcagg aaatgtccaa agatttagaa    180
gaggtgaagg ccaaggttca gccatatctc gatgactttc agaaaaaatg cagggaagag    240
atggaattat atcgtcaaaa ggtggaaccg ctgcgtgcgg aactgcaaga gggggcacgc    300
caaaaactcc atgagctcca agagaagctc agcccattag gcgaagaaat gcgcgatcgc    360
gcccgtgcac atgttgatgc actccggact catttggcgc cgtattcgga tgaacttcgc    420
cagcgtttgg ccgcacgtct cgaggcgctg aaagaaaacg ggggtgcccg cttggctgag    480
taccacgcat gcgcgacaga cacctgagc accttgagcg aaaaagcgaa accggcgctg    540
gaagatctac gccagggctt attgcctgtt cttgagagct ttaaagtcag ttttctgtca    600
gctctggaag aatatactaa aaagctgaat acccag    636
```

<210> SEQ ID NO 93
<211> LENGTH: 212
<212> TYPE: PRT
<213> ORGANISM: Artificial
<220> FEATURE:
<223> OTHER INFORMATION: MSP1K152C

<400> SEQUENCE: 93

```
Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Cys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln
    210
```

<210> SEQ ID NO 94
<211> LENGTH: 6
<212> TYPE: PRT
<213> ORGANISM: Artificial
<220> FEATURE:

```
<223> OTHER INFORMATION: peptide segment

<400> SEQUENCE: 94

Ser Asn Pro Gly Thr Gln
1               5

<210> SEQ ID NO 95
<211> LENGTH: 279
<212> TYPE: PRT
<213> ORGANISM: Artificial
<220> FEATURE:
<223> OTHER INFORMATION: Recombinant Tissue Factor with truncated
      cytoplasmic domain

<400> SEQUENCE: 95

Met Lys Tyr Leu Leu Pro Thr Ala Ala Ala Gly Leu Leu Leu Leu Ala
1               5                   10                  15

Ala Gln Pro Ala Met Ala Ala Glu Asp Gln Val Asp Pro Arg Leu Ile
                20                  25                  30

Asp Gly Lys Ser Gly Thr Thr Asn Thr Val Ala Ala Tyr Asn Leu Thr
            35                  40                  45

Trp Lys Ser Thr Asn Phe Lys Thr Ile Leu Glu Trp Glu Pro Lys Pro
50                  55                  60

Val Asn Gln Val Tyr Thr Val Gln Ile Ser Thr Lys Ser Gly Asp Trp
65                  70                  75                  80

Lys Ser Lys Cys Phe Tyr Thr Thr Asp Thr Glu Cys Asp Leu Thr Asp
                85                  90                  95

Glu Ile Val Lys Asp Val Lys Gln Thr Tyr Leu Ala Arg Val Phe Ser
            100                 105                 110

Tyr Pro Ala Gly Asn Val Glu Ser Thr Gly Ser Ala Gly Glu Pro Leu
        115                 120                 125

Tyr Glu Asn Ser Pro Glu Phe Thr Pro Tyr Leu Glu Thr Asn Leu Gly
130                 135                 140

Gln Pro Thr Ile Gln Ser Phe Glu Gln Val Gly Thr Lys Val Asn Val
145                 150                 155                 160

Thr Val Glu Asp Glu Arg Thr Leu Val Arg Arg Asn Asn Thr Phe Leu
                165                 170                 175

Ser Leu Arg Asp Val Phe Gly Lys Asp Leu Ile Tyr Thr Leu Tyr Tyr
            180                 185                 190

Trp Lys Ser Ser Ser Ser Gly Lys Lys Thr Ala Lys Thr Asn Thr Asn
        195                 200                 205

Glu Phe Leu Ile Asp Val Asp Lys Gly Glu Asn Tyr Cys Phe Ser Val
210                 215                 220

Gln Ala Val Ile Pro Ser Arg Thr Val Asn Arg Lys Ser Thr Asp Ser
225                 230                 235                 240

Pro Val Glu Cys Met Gly Gln Glu Lys Gly Glu Phe Arg Glu Ile Phe
                245                 250                 255

Tyr Ile Ile Gly Ala Val Val Phe Val Val Ile Ile Leu Val Ile Ile
            260                 265                 270

Leu Ala Ile Ser Leu His Lys
        275

<210> SEQ ID NO 96
<211> LENGTH: 4
<212> TYPE: PRT
<213> ORGANISM: Artificial
<220> FEATURE:
<223> OTHER INFORMATION: linker peptide segment
```

```
<400> SEQUENCE: 96

Asn Pro Gly Thr
1
```

What is claimed is:

1. A method for controlling bleeding in a human or animal patient, said method comprising the step of administering, in an amount effective to control bleeding in said patient a composition comprising nanoscale particles comprising tissue factor or recombinant tissue factor, a membrane scaffold protein and phospholipid, wherein the phospholipid comprises a net-negatively charged phospholipid, and wherein said nanoscale particles are attached to a solid support, whereby bleeding in said patient is controlled.

2. The method of claim 1, wherein the phospholipid comprises from 1 to 50% on a molar basis of net-negative charged phospholipid and from 50 to 99% net-neutral phospholipid.

3. The method of claim 1, wherein the phospholipid consists essentially of phosphatidylserine and phosphatidylcholine or phosphatidylserine and phosphatidylethanolamine in a molar ratio of 20:80 or consists essentially of phosphatidylserine, phosphatidylcholine and phosphatidylethanolamine in a molar ratio of 20:40:40.

4. The method of claim 1, wherein the human or animal patient has hemophilia, a thrombocytopenia or other bleeding diathesis.

5. The method of claim 1, wherein the patient has a surgical, wound or soft tissue trauma resulting in bleeding.

6. The method of claim 1, wherein the solid support is a collagen containing material.

7. The method of claim 1, wherein the membrane scaffold protein comprises an amino acid sequence selected from the group consisting of SEQ ID NO:2, SEQ ID NO: 4, SEQ ID NO:6, SEQ ID NO:8, amino acids 13-414 of SEQ ID NO:8, SEQ ID NO:10, amino acids 13-422 of SEQ ID NO:10, SEQ ID NO:12, amino acids 13-168 of SEQ ID NO:12, SEQ ID NO:14, amino acids 13-168 of SEQ ID NO:14, SEQ ID NO:16, amino acids 13-201 of SEQ ID NO:16, SEQ ID NO:17, amino acids 13-201 of SEQ ID NO:17, SEQ ID NO:18, amino acids 13-392 of SEQ ID NO:18, SEQ ID NO:50, amino acids 13-234 of SEQ ID NO:50, SEQ ID NO:51, amino acids 13-256 of SEQ ID NO:51, SEQ ID NO:52, amino acids 13-278 of SEQ ID NO:52, SEQ ID NO:53, amino acids 24-223 of SEQ ID NO:53, SEQ ID NO:54, SEQ ID NO:55, amino acids 24-212 of SEQ ID NO:55, SEQ ID NO:56, SEQ ID NO:57, amino acids 24-201 of SEQ ID NO:57, SEQ ID NO:58, amino acids 13-190 of SEQ ID NO:58, SEQ ID NO:59, amino acids 13-201 of SEQ ID NO:59, SEQ ID NO:60, amino acids 13-190 of SEQ ID NO:60, SEQ ID NO:61, amino acids 24-201 of SEQ ID NO:61, SEQ ID NO:62, amino acids 24-190 of SEQ ID NO:62, SEQ ID NO:63, amino acids 24-179 of SEQ ID NO:63, SEQ ID NO:64, amino acids 24-289 of SEQ ID NO:64, SEQ ID NO:65, amino acids 24-289 of SEQ ID NO:64, SEQ ID NO:65, amino acids 24-278 of SEQ ID NO:65, SEQ ID NO:66, amino acids 24-423 of SEQ ID NO:66, SEQ ID NO:67, amino acids 24-199 of SEQ ID NO:67, SEQ ID NO:68, amino acids 24-401 of SEQ ID NO:68, SEQ ID NO:69, amino acids 24-392 of SEQ ID NO:69, SEQ ID NO:81, amino acids 24-397 of SEQ ID NO:81, SEQ ID NO:83, amino acids 24-383 of SEQ ID NO:83, SEQ ID NO:85, amino acids 24-379 of SEQ ID NO:85, SEQ ID NO:87, amino acids 24-381 of SEQ ID NO:87, SEQ ID NO:89, amino acids 25-212 of SEQ ID NO:89, SEQ ID NO:91, amino acids 25-212 of SEQ ID NO:91, SEQ ID NO:93 and amino acids 13-212 of SEQ ID NO:93.

8. The method of claim 1, wherein the tissue factor is a recombinant tissue factor consisting of amino acids 23 to 277 of SEQ ID NO:95.

\* \* \* \* \*